US007384949B2

(12) United States Patent
Gillespie et al.

(10) Patent No.: US 7,384,949 B2
(45) Date of Patent: Jun. 10, 2008

(54) THIENO(3,2-D)PYRIMIDINES AND FURANO(3,2-D)PYRIMIDINES AND THEIR USE AS PURINERGIC RECEPTOR ANTAGONISTS

(75) Inventors: Roger John Gillespie, Winnersh (GB); Joanne Lerpiniere, Winnersh (GB); Claire Elizabeth Dawson, Winnersh (GB); Suneel Gaur, Winnersh (GB); Robert Mark Pratt, Winnersh (GB)

(73) Assignee: Vernalis Research Limited, Wokingham (GB)

( * ) Notice: Subject to any disclaimer, the term of this patent is extended or adjusted under 35 U.S.C. 154(b) by 312 days.

(21) Appl. No.: 10/250,938

(22) PCT Filed: Jan. 10, 2002

(86) PCT No.: PCT/GB02/00084

§ 371 (c)(1),
(2), (4) Date: Nov. 4, 2003

(87) PCT Pub. No.: WO02/055524

PCT Pub. Date: Jul. 18, 2002

(65) Prior Publication Data
US 2004/0097524 A1    May 20, 2004

(30) Foreign Application Priority Data
Jan. 10, 2001   (GB)  .................. 0100620.4

(51) Int. Cl.
C07D 491/04    (2006.01)
C07D 495/04    (2006.01)
A61K 31/519    (2006.01)
A61P 25/24     (2006.01)
A61P 25/04     (2006.01)
A61P 25/28     (2006.01)
A61P 25/16     (2006.01)
A61P 25/14     (2006.01)

(52) U.S. Cl. .................. 514/260.1; 544/278
(58) Field of Classification Search ............ 544/278; 514/260.1
See application file for complete search history.

(56) References Cited

U.S. PATENT DOCUMENTS

| 6,197,788 | B1 | 3/2001 | Fletcher et al. |
| 6,583,156 | B1 | 6/2003 | Gillespie et al. |
| 6,608,085 | B1 | 8/2003 | Gillespie et al. |
| 6,787,541 | B1 | 9/2004 | Gillespie et al. |

FOREIGN PATENT DOCUMENTS

| EP | 1 221 444 A1 | 7/2002 |
| EP | 1 300 147 A1 | 4/2003 |
| JP | 04-36284 * | 2/1992 |
| WO | WO 99/21617 A | 5/1999 |
| WO | WO 99/40091 | 8/1999 |
| WO | WO 01/02409 A | 1/2001 |
| WO | WO 01/62233 A | 8/2001 |

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
Kulisevsky, Jaime; Barbanoj, Manel; Gironell, Alexandre; Antonijoan, Rosa; Casas, Miquel; Pascual-Sedano, Berta, Clinical Neuropharmacology. 25(1):25-31, Jan./Feb. 2002, abstract only.*
Morelli, Micaela, Experimental Neurology, 184, 20-23, 2003.*
Tuite, Paul et al, Expert. Opin. Investig. Drugs, 12, 1335-1352, 2003.*

(Continued)

Primary Examiner—Brenda L. Coleman
Assistant Examiner—Susanna Moore
(74) Attorney, Agent, or Firm—Foley & Lardner LLP

(57) ABSTRACT

A compound of formula (I), wherein X is S or O; $R_1$ is selected from H, alkyl, aryl, hydroxy, alkoxy, aryloxy, thioalkyl, thioaryl, halogen, CN, $COR_5$, $CO_2R_5$, $CONR_6R_7$, $CONR_5NR_6R_7$, $NR_6R_7$, $NR_5CONR_6R_7$, $NR_5COR_6$, $NR_5CO_2R_8$, and $NR_5SO_2R_8$; $R_2$ is selected from aryl attached via an unsaturated carbon atom; $R_3$ is selected from H, alkyl, hydroxy, alkoxy, halogen, CN and $NO_2$; $R_4$ is selected from H, alkyl, aryl, hydroxy, alkoxy, aryloxy, thioalkyl, thioaryl, halogen, CN, $NO_2$, $COR_5$, $CO_2R_5$, $CONR_6R_7$, $CONR_5NR_6R_7$, $NR_6R_7$, $NR_5CONR_6R_7$, $NR_5COR_6$, $NR_5CO_2R_8$ and $NR_5SO_2R_8$; $R_5$, $R_6$ and $R_7$ are independently selected from H, alkyl and aryl or where $R_6$ and $R_7$ are in an $(NR_6R_7)$ group, $R_6$ and $R_7$ may be linked to form a heterocyclic group, or where $R_5$, $R_6$ and $R_7$ are in a $(CONR_5NR_6R_7)$ group, $R_5$ and $R_6$ may be linked to form a heterocyclic group; and $R_8$ is selected from alkyl and aryl, or a pharmaceutically acceptable salt thereof or prodrug thereof, and the use thereof in therapy and in the treatment or prevention of a disorder in which the blocking of purine receptors, particularly adenosine receptors and more particularly $A_{2A}$ receptors, may be beneficial, particularly wherein said disorder is a movement disorder such a Parkinson's disease or said disorder is depression, cognitive or memory impairment, acute or chronic pain, ADHD or narcolepsy, or wherein said medicament is for neuroprotection in a subject

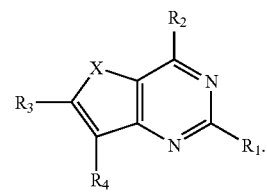

(1)

30 Claims, No Drawings

OTHER PUBLICATIONS

Bibbiani, F. et al, Experimental Neurology, 184, 285-294, 2003.*
Spiros Konitsiotis, Expert. Opin. Investig. Drugs, 14, 377-392 2005.*
Anonymous, Drug and Therapeutic Bulletin, 35, pp. 36-40, 1999.*
LeWitt, Peter A., Pharmacotherapy, 20, pp. 26S-32S, 2000.*
Loscher W.,.Epilepsy Res. Jun. 2002;50(1-2):105-23.*
Jennifer L. Hellier, Peter R. Patrylo, Ping Dou, Michelle Nett, Gregory M. Rose, and F. Edward Dudek, J. Neurosci. 1999, 19(22):10053-10064.*
Wenning GK, Granata R, Puschban Z, Scherfler C, Poewe W., .J Neural Transm Suppl. 1999;55:103-13, Medline abstract PMID: 10335497.*
Rebecca J. Carter et al ,The Journal of Neuroscience, Apr. 15, 1999, 19(8):3248-3257.*
Yanamoto H, Nagata I, Niitsu Y, Xue JH, Zhang Z, Kikuchi H., Evaluation of MCAO stroke models in normotensive rats: standardized neocortical infarction by the 3VO technique, Exp Neurol. Aug. 2003;182(2):261-74.*
Osborne NN, Chidlow G, Layton CJ, Wood JP, Casson RJ ,Melena J., Optic nerve and neuroprotection strategies.Eye. Nov. 2004;18(11):1075-84.*
Jenner, Peter, Expert Opin. Investig. Drugs, 14(6), 2005, pp. 729-738.*
Bailey et al., "Changes in spinalσ- and κopioid systems in mice deficient in the A2A receptor gene", Journal of Neuroscience, vol. 22, No. 21, 2002, abstract only.
Bara-Jimenez et al., "Adenosine A2A receptor antagonist treatment of Parkinson's disease", *Neurology* vol. 61, No. 3, 2003, abstract only.
Bastia et al., *Neurosci*, vol. 328, No. 3, Lett. 2002 (pp. 241-244).
Behan et al., Br. J. Pharmacology, vol. 135, 2002 (pp. 1435-1442).
Bertorelli et al., "Effects of selective agonists and antagonists for A1 or A2a adenosine receptor on sleep-walking patterns in rats", *Drug Development Research*, Wiley-Liss, Inc., Research Articles, vol. 37, 1996 (pp. 65-72).
Chase et al., "Translating $A_{2a}$ antagonist KW6002 from animal models to parkinsonian patients", *Neurology*, vol. 61, No. 11, Suppl. 6, abstract only, (2003).
Dall'lgna et al., *Br. J. Pharmacology*, vol. 138, 2003 (pp. 1207-1209).
Ei Yacoubi et al., *Br. J. Pharmacology*, vol. 134, No. 1, 2001 (pp. 68-77).
Fredholm, B.B. et al., "Actions of caffeine in the brain with special reference to factors that contribute to its widespread use", *Pharmacol. Rev.*, vol. 51, 1999 (pp. 83-133).
Garfinkel, B.D. et al., "Responses to methylphenidate and varied doses of caffeine in children with attention deficit disorder", *Can. J. Psychiatry*, vol. 26, 1981 (pp. 395-401).
Gonzalez-Benitez, European Journal of Pharmacology, vol. 437, Elsevier, 2002 (pp. 105-111).
Hauser et al., "Randomized trial of the adenosine A2A receptor antagonist istradefylline in advanced PD", *Neurology*, vol. 61, No. 3, 2003, abstract only.
Hess, "Recent advances in Adenosine Receptor Antagonist Research, Review, Monthly Focus: Central and Peripheral Nervous Systems", *Ashley Publications Ltd.*, 2001 (pp. 1533-1561).
Ikeda et al., "Neuroprotection by adenosine A2A receptor blockade in experimental models of Parkinson's disease", *Journal of Neurochemistry*, vol. 80, No. 2, 2002 (pp. 262-270).
Kase, "New aspects of physiological and pathophysiological functions of adenosine A2A receptor in basal ganglia", *Bioscience, Biotechnology, and Biochemistry*, vol. 65, No. 7, abstract only, (2001).

Kopf et al., "Adenosine and memory storage: effect of A1 and A2 receptor antagonists", *Psychopharmacology (Berlin)*, vol. 146, No. 2, 1999 (pp. 214-219).
Ledent et al., "Aggressiveness, hypoalgesia and high blood pressure in mice lacking the adenosine A2a receptor", *Nature*, vol. 388, No. 6643, Aug. 14, 1997 (pp. 674-678).
Li et al., *Exp. Eye Res.*, vol. 68, Academic Press, 1999 (pp. 9-17).
Mally and Stone, *CNS Drugs*, vol. 19, No. 5, 1998 (pp. 311-320).
Monopoli et al., *Journal of Pharmacology and Experimental Therapeutics*, vol. 255, No., 1, The American Society for Pharmacology and Experimental Therapeutics, 1998 (pp. 9-15).
Monopoli et al., *NeuroReport 9*, 1998 (pp. 3955-3959).
Ongini et al., "Dual actions of A2A adenosine receptor antagonists on motor dysfunction and neurodegenerative processes", *Drug Development Research*, vol. 52, No. 1/2, 2001 (pp. 379-386).
Popoli et al., "Blockade of striatal adenosine A2A receptor reduces, through a presynaptic mechanism, quinolinic acid-induced excitotoxicity: possible relevance to neuroprotective interventions in neurodegenerative diseases of the striatum", *Journal of Neuroscience*, vol. 22, No. 5, 2002 (pp. 1967-1975).
Satoh et al., "Involvement of adenosine A2A rreceptor in sleep promotion", *European Journal of Pharmacology*, vol. 351, Elsevier, 1998 (pp. 152-162).
Scammel et al., "An adenosine A2a agonist increases sleep and induces fos in ventrolateral preoptic neurons", *Neuroscience*, vol. 107 No. 4, Pergamon, 2001 (pp. 653-663).
Schechter, M.D. et al., "Objectively measured hyperactivity—II. Caffeine and amphetamine effects", *J. Clin. Pharmacol.*, vol. 25, 1985 (pp. 276-280).
Stone et al., *Drug Dev. Res.*, vol. 52 No. 1/2, 2001 (pp. 323-330).
Svenningsson, P. et al., "Distribution, biochemistry and function of striatal adenosine $A_{2A}$ receptors", *Prog. Neurobiol.*, vol. 59, 1999 (pp. 355-3596).
Urade et al., "Sleep regulation in adenosine $A_{2A}$ receptor-deficient mice", *Neurology*, vol. 61, No. 11, Suppl. 6, 2003 (pp. S94-S96).
Varani et al., "Aberrant $A_{2A}$ receptor function in peripheral blood cells in Huntington's disease", *FASEB Journal*, vol. 17, No. 14, 2003 (pp. 2148-2150).
Varani et al., *Colloque Scientifique sur le Café*, 2001, 19$^{th}$ (pp. 51-58).
Patent Abstracts of Japan, vol. 016, No. 207 (C-0941), May 18, 1992 & JP 04 036284 A (Sumitomo Chem. Co. Ltd.), Feb. 6, 1992, abstract.
Bara-Jimenez et al., Adenosine $A_{2A}$receptor antagonist treatment of Parkinson's disease. Neurology, 61:293-296, Aug. 2003.
Bailey et al., Changes in Spinal σand κopioid systems in mice deficient in the $A_{2A}$ receptor gene. The Journal of Neuroscience, 22(21):9210-9220, Nov. 1, 2002.
Chase et al., Translating $A_{2A}$ antagonist KW6002 from animal models to parkinsonian patients. Neurology, 61(Supp. 6): S107-S111, Dec. 2003.
Hauser et al., Ramdomized trial of the adenosine $A_{2A}$ receptor antagonist istradefylline in advanced PD. Neurology, 61:297-303, Aug. 2003.
Hiroshi Kase, New aspects of physiological and pathophysiological functions of adenosine $A_{2A}$ receptor in basal ganglia. Biosci. Biotechnol. Biochem., 65(7): 1447-1457, 2001.

* cited by examiner

THIENO(3,2-D)PYRIMIDINES AND FURANO(3,2-D)PYRIMIDINES AND THEIR USE AS PURINERGIC RECEPTOR ANTAGONISTS

This application is a national phase entry of PCT Application No. PCT/GB02/00084, filed on Jan. 10, 2002, which claims priority to British Patent Application No. GB 0100620.4, filed Jan. 10, 2001.

The present invention relates to thieno(3,2-d)pyrimidines and furano(3,2-d)pyrimidines and their use in therapy. In particular, the present invention relates to the treatment of disorders in which the reduction of purinergic neurotransmission could be beneficial. The invention relates in particular to blockade of adenosine receptors and particularly adenosine $A_{2A}$ receptors, and to the treatment of movement disorders such as Parkinson's disease.

Movement disorders constitute a serious health problem, especially amongst the elderly sector of the population. These movement disorders are often the result of brain lesions. Disorders involving the basal ganglia which result in movement disorders include Parkinson's disease, Huntington's chorea and Wilson's disease. Furthermore, dyskinesias often arise as sequelae of cerebral ischaemia and other neurological disorders.

There are four classic symptoms of Parkinson's disease: tremor, rigidity, akinesia and postural changes. The disease is also commonly associated with depression, dementia and overall cognitive decline. Parkinson's disease has a prevalence of 1 per 1,000 of the total population. The incidence increases to 1 per 100 for those aged over 60 years. Degeneration of dopaminergic neurones in the substantia nigra and the subsequent reductions in interstitial concentrations of dopamine in the striatum are critical to the development of Parkinson's disease. Some 80% of cells from the substantia nigra need to be destroyed before the clinical symptoms of Parkinson's disease are manifested.

Current strategies for the treatment of Parkinson's disease are based on transmitter replacement therapy (L-dihydroxyphenylacetic acid (L-DOPA)), inhibition of monoamine oxidase (e.g. Deprenyl®), dopamine receptor agonists (e.g. bromocriptine and apomorphine) and anticholinergics (e.g. benztrophine, orphenadrine). Transmitter replacement therapy in particular does not provide consistent clinical benefit, especially after prolonged treatment when "on-off" symptoms develop, and this treatment has also been associated with involuntary movements of athetosis and chorea, nausea and vomiting. Additionally current therapies do not treat the underlying neurodegenerative disorder resulting in a continuing cognitive decline in patients. Despite new drug approvals, there is still a medical need in terms of improved therapies for movement disorders, especially Parkinson's disease. In particular, effective treatments requiring less frequent dosing, effective treatments which are associated with less severe side-effects, and effective treatments which control or reverse the underlying neurodegenerative disorder, are required.

Blockade of $A_2$ adenosine receptors has recently been implicated in the treatment of movement disorders such as Parkinson's disease (Richardson, P. J. et al., *Trends Pharmacol. Sci.* 1997, 18, 338-344) and in the treatment of cerebral ischaemia (Gao, Y. and Phillis, J. W., *Life Sci.* 1994, 55, 61-65). The potential utility of adenosine $A_{2A}$ receptor antagonists in the treatment of movement disorders such as Parkinson's Disease has recently been reviewed (Mally, J. and Stone, T. W., *CNS Drugs*, 1998, 10, 311-320).

Adenosine is a naturally occurring purine nucleoside which has a wide variety of well-documented regulatory functions and physiological effects. The central nervous system (CNS) effects of this endogenous nucleoside have attracted particular attention in drug discovery, owing to the therapeutic potential of purinergic agents in CNS disorders (Jacobson, K. A. et al., *J. Med. Chem.* 1992, 35, 407-422). This therapeutic potential has resulted in considerable recent research endeavour within the field of adenosine receptor agonists and antagonists (Bhagwhat, S. S.; Williams, M. *Exp. Opin. Ther. Patents* 1995, 5,547-558).

Adenosine receptors represent a subclass ($P_1$) of the group of purine nucleotide and nucleoside receptors known as purinoreceptors. The main pharmacologically distinct adenosine receptor subtypes are known as $A_1$, $A_{2A}$, $A_{2B}$ (of high and low affinity) and $A_3$ (Fredholm, B. B., et al., *Pharmacol. Rev.* 1994, 46, 143-156). The adenosine receptors are present in the CNS (Fredholm, B. B., *News Physiol. Sci.*, 1995, 10, 122-128).

The design of $P_1$ receptor-mediated agents has been reviewed (Jacobson, K. A., Suzuki, F., *Drug Dev. Res.*, 1997, 39, 289-300; Baraldi, P. G. et al., *Curr. Med. Chem.* 1995, 2, 707-722), and such compounds are claimed to be useful in the treatment of cerebral ischemia or neurodegenerative disorders, such as Parkinson's disease (Williams, M. and Burnstock, G. *Purinergic Approachies Exp. Ther.* (1997), 3-26. Editor: Jacobson, Kenneth A.; Jarvis, Michael F. Publisher: Wiley-Liss, New York, N.Y.)

It has been speculated that xanthine derivatives such as caffeine may offer a form of treatment for attention-deficit hyperactivity disorder (ADHD). A number of studies have demonstrated a beneficial effect of caffeine on controlling the symptoms of ADHD (Garfinkel, B. D. et al., *Psychiatry*, 1981, 26, 395-401). Antagonism of adenosine receptors is thought to account for the majority of the behavioural effects of caffeine in humans and thus blockade of adenosine $A_{2A}$ receptors may account for the observed effects of caffeine in ADHD patients. Therefore a selective $A_{2A}$ receptor antagonist may provide an effective treatment for ADHD but without the unwanted side-effects associated with current therapy.

Adenosine receptors have been recognised to play an important role in regulation of sleep patterns, and indeed adenosine antagonists such as caffeine exert potent stimulant effects and can be used to prolong wakefulness (Porkka-Heiskanen, T. et al., *Science*, 1997, 276, 1265-1268). Recent evidence suggests that a substantial part of the actions of adenosine in regulating sleep is mediated through the adenosine $A_{2A}$ receptor (Satoh, S., et al., *Proc. Natl. Acad. Sci.*, USA, 1996). Thus, a selective $A_{2A}$ receptor antagonist may be of benefit in counteracting excessive sleepiness in sleep disorders such as hypersomnia or narcolepsy.

It has recently been observed that patients with major depression demonstrate a blunted response to adenosine agonist-induced stimulation in platelets, suggesting that a dysregulation of $A_{2A}$ receptor function may occur during depression (Berk, M. et al, 2001, *Eur. Neuropsychopharmacol.* 11, 183-186). Experimental evidence in animal models has shown that blockade of $A_{2A}$ receptor function confers antidepressant activity (El Yacoubi, M et al. *Br. J. Pharmacol.* 2001, 134, 68-77). Thus, $A_{2A}$ receptor antagonists may offer a novel therapy for the treatment of major depression and other affective disorders in patients.

The pharmacology of adenosine $A_{2A}$ receptors has been reviewed (Ongini, E.; Fredholm, B. B. *Trends Pharmacol. Sci.* 1996, 17(10), 364-372). One potential underlying mechanism in the aforementioned treatment of movement disorders by the blockade of $A_2$ adenosine receptors is the evidence of a functional link between adenosine $A_{2A}$ receptors to dopamine $D_2$ receptors in the CNS. Some of the early studies (e.g. Ferre, S. et al., Stimulation of high-affinity adenosine $A_2$ receptors decreases the affinity of dopamine $D_2$ receptors in rat striatal membranes. *Proc. Natl. Acad. Sci U.S.A.* 1991, 88, 723841) have been summarised in two more recent articles (Fuxe, K. et al., *Adenosine Adenine Nucleotides Mol. Biol. Integr. Physiol.*, [Proc. Int. Symp.], 5th (1995), 499-507. Editors: Belardinelli, Luiz; Pelleg, Amir. Publisher: Kluwer, Boston, Mass.; Ferre, S. et al., *Trends Neurosci.* 1997,20,482-487).

As a result of these investigations into the functional role of adenosine $A_{2A}$ receptors in the CNS, especially in vivo studies linking $A_2$ receptors with catalepsy (Ferre et al., *Neurosci. Lett.* 1991, 130, 162-4; Mandhane, S. N. et al., *Eur. J. Pharmacol.* 1997, 328, 135-141) investigations have been made into agents which selectively bind to adenosine $A_{2A}$ receptors as potentially effective treatments for Parkinson's disease.

While many of the potential drugs for treatment of Parkinson's disease have shown benefit in the treatment of movement disorders, an advantage of adenosine $A_{2A}$ antagonist therapy is that the underlying neurodegenerative disorder may also be treated. The neuroprotective effect of adenosine $A_{2A}$ antagonists has been reviewed (Ongini, E.; Adami, M.; Ferri, C.; Bertorelli, R., *Ann. N.Y. Acad. Sci.* 1997, 825(Neuroprotective Agents), 30-48). In particular, compelling recent evidence suggests that blockade of $A_{2A}$ receptor function confers neuroprotection against MTP-induced neurotoxicity in mice (Chen, J-F., *J. Neurosci.* 2001, 21, RC143). In addition, several recent studies have shown that consumption of dietary caffeine, a known adenosine $A_{2A}$ receptor antagonist, is associated with a reduced risk of Parkinson's disease in man (Ascherio, A. et al, *Ann Neurol.*, 2001, 50, 56-63; Ross G W, et al., *JAMA*, 2000, 283, 2674-9). Thus, $A_{2A}$ receptor antagonists may offer a novel treatment for conferring neuroprotection in neurodegenerative diseases such as Parkinson's disease.

Xanthine derivatives have been disclosed as adenosine $A_2$ receptor antagonists as useful for treating various diseases caused by hyperfunctioning of adenosine $A_2$ receptors, such as Parkinson's disease (see, for example, EP-A-565377).

One prominent xanthine-derived adenosine $A_{2A}$ selective antagonist is CSC [8-(3-chlorostyryl)caffeine] (Jacobson et al., *FEBS Lett.*, 1993, 323, 141-144).

Theophylline (1,3-dimethylxanthine), a bronchodilator drug which is a mixed antagonist at adenosine $A_1$ and $A_{2A}$ receptors, has been studied clinically. To determine whether a formulation of this adenosine receptor antagonist would be of value in Parkinson's disease an open trial was conducted on 15 Parkinsonian patients, treated for up to 12 weeks with a slow release oral theophylline preparation (150 mg/day), yielding serum theophylline levels of 4.44 mg/L after one week. The patients exhibited significant improvements in mean objective disability scores and 11 reported moderate or marked subjective improvement (Mally, J., Stone, T-.W. *J. Pharm. Pharmacol.* 1994, 46, 515-517).

KF 17837 [(E)-8-(3,4-dimethoxystyryl)-1,3-dipropyl-7-methylxanthine] is a selective adenosine $A_{2A}$ receptor antagonist which on oral administration significantly ameliorated the cataleptic responses induced by intracerebroventricular administration of an adenosine $A_{2A}$ receptor agonist, CGS 21680. KF 17837 also reduced the catalepsy induced by haloperidol and reserpine. Moreover, KF 17837 potentiated the anticataleptic effects of a subthreshold dose of L-DOPA plus benserazide, suggesting that KE 17837 is a centrally active adenosine $A_{2A}$ receptor antagonist and that the dopaminergic function of the nigrostriatal pathway is potentiated by adenosine $A_{2A}$ receptor antagonists (Kanda, T. et al., *Eur. J. Pharmacol.* 1994, 256, 263-268). The structure activity relationship (SAR) of KF 17837 has been published (Shimada, J. et al., *Bioorg. Med Chem. Lett.* 1997, 7, 2349-2352). Recent data has also been provided on the $A_{2A}$ receptor antagonist KW-6002 (Kuwana, Y et al., *Soc. Neurosci. Abstr.* 1997, 23, 119.14; and Kanda, T. et al., *Ann. Neurol.* 1998, 43(4), 507-513).

New non-xanthine structures sharing these pharmacological properties include SCH 58261 and its derivatives (Baraldi, P. G. et al., Pyrazolo[4,3-e]-1,2,4-triazolo[1,5-c] pyrimidine Derivatives: Potent and Selective $A_{2A}$ Adenosine Antagonists. *J. Med. Chem.* 1996, 39, 1164-71). SCH 58261 (7-(2-phenylethyl)-5-amino-2-(2-furyl)-pyrazolo-[4,3-e]-1, 2,4-triazolo[1,5-c]pyriridine) is reported as effective in the treatment of movement disorders (Ongini, E. *Drug Dev. Res.* 1997, 42(2), 63-70) and has been followed up by a later series of compounds (Baraldi, P. G. et al., *J. Med. Chem.* 1998, 41(12), 2126-2133).

The foregoing discussion indicates that a potentially effective treatment for movement disorders in humans would comprise agents which act as antagonists at adenosine $A_{2A}$ receptors.

It has now been found that thieno(3,2-d)pyrimidines and furano(3,2-d)pyrimidines, which are structurally unrelated to known adenosine receptor antagonists, exhibit unexpected antagonist binding affinity at adenosine ($P_1$) receptors, and in particular at the adenosine $A_{2A}$ receptor. Such compounds may therefore be useful for the treatment of disorders in which the blocking of purine receptors, particularly adenosine receptors and more particularly adenosine $A_{2A}$ receptors, may be beneficial. In particular such compounds may be suitable for the treatment of movement disorders, such as disorders of the basal ganglia which result in dyskinesias. Disorders of particular interest include Parkinson's disease, Alzheimer's disease, spasticity, Huntington's chorea and Wilson's disease.

Such compounds may also be particularly suitable for the treatment of depression, cognitive or memory impairment including Alzheimer's disease, acute or chronic pain, ADHD, narcolepsy or for neuroprotection.

According to the present invention there is provided a compound of formula (I):

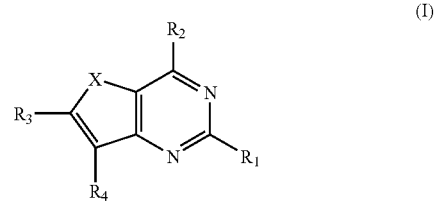

wherein

X is S or O;

$R_1$ is selected from H, alkyl, aryl, hydroxy, alkoxy, aryloxy, thioalkyl, thioaryl, halogen, CN, $COR_5$, $CO_2R_5$, $CONR_6R_7$, $CONR_5NR_6R_7$, $NR_6R_7$, $NR_5CONR_6R_7$, $NR_5COR_6$, $NR_5CO_2R_8$, and $NR_5SO_2R_8$;

$R_2$ is selected from aryl attached via an unsaturated carbon atom;

$R_3$ is selected from H, alkyl, hydroxy, alkoxy, halogen, CN and $NO_2$;

$R_4$ is selected from H, alkyl, aryl, hydroxy, alkoxy, aryloxy, thioalkyl, thioaryl, halogen, CN, $NO_2$, $COR_5$, $CO_2R_5$, $CONR_6R_7$, $CONR_5NR_6R_7$, $NR_6R_7$, $NR_5CONR_6R_7$, $NR_5COR_6$, $NR_5CO_2R_8$ and $NR_5SO_2R_8$;

$R_5$, $R_6$ and $R_7$ are independently selected from H, alkyl and aryl, or where $R_6$ and $R_7$ are in an ($NR_6R_7$) group, $R_6$ and $R_7$ may be linked to form a heterocyclic group, or where $R_5$, $R_6$ and $R_7$ are in a ($CONR_5NR_6R_7$) group, $R_5$ and $R_6$ may be linked to form a heterocyclic group; and $R_8$ is selected from alkyl and aryl, or a pharmaceutically acceptable salt thereof or prodrug thereof.

As used herein, the term "alkyl" means a branched or unbranched, cyclic or acyclic, saturated or unsaturated (e.g. alkenyl or alkynyl) hydrocarbyl radical which may be substituted or unsubstituted. Where cyclic, the alkyl group is preferably $C_3$ to $C_{12}$, more preferably $C_5$ to $C_{10}$, more preferably $C_5$, $C_6$ or $C_7$. Where acyclic, the alkyl group is preferably $C_1$ to $C_{10}$, more preferably $C_1$ to $C_6$, more preferably methyl, ethyl, propyl (n-propyl or isopropyl), butyl (n-butyl, isobutyl or tertiary-butyl) or pentyl (including n-pentyl and iso-pentyl), more preferably methyl. It will be appreciated therefore that the term "alkyl" as used herein includes alkyl (branched or unbranched), alkenyl (branched or unbranched), alkynyl (branched or unbranched), cycloalkyl, cycloalkenyl and cycloalkynyl.

As used herein, the term "lower alkyl" means methyl, ethyl, propyl (n-propyl or isopropyl) or butyl (n-butyl, isobutyl or tertiary-butyl).

As used herein, the term "aryl" means an aromatic group, such as phenyl or naphthyl (preferably phenyl), or a heteroaromatic group containing one or more heteroatom(s) preferably selected from N, O and S, such as pyridyl, pyrrolyl, quinolinyl, furanyl, thienyl, oxadiazolyl, thiadiazolyl, thiazolyl, oxazolyl, isoxazolyl, pyrazolyl, triazolyl, imidazolyl or pyrimidinyl.

As used herein, the term "heteroaryl" means an aromatic group containing one or more heteroatom(s) preferably selected from N, O and S, such as pyridyl, pyrrolyl, quinolinyl, furanyl, thienyl, oxadiazolyl, thiadiazolyl, thiazolyl, oxazolyl, isoxazolyl, pyrazolyl, triazolyl, imidazolyl or pyrimidinyl.

As used herein, the term "alkoxy" means alkyl-O—. As used herein, the term "aryloxy" means aryl-O—.

As used herein, the term "halogen" means a fluorine, chlorine, bromine or iodine radical.

As used herein, the term "ortho,ortho-disubstituted aryl groups" refers to aryl groups which are substituted in both ortho positions of the aryl group relative to the point of attachment of the aryl group to the pyrimidine ring.

As used herein, the term "prodrug" means any pharmaceutically acceptable prodrug of a compound of the present invention.

Where any of $R_1$ to $R_{13}$ is selected from alkyl, alkoxy and thioalkyl, in accordance with formula (I) as defined above, then that alkyl group, or the alkyl group of the alkoxy or thioalkyl group, may be substituted or unsubstituted. Where any of $R_1$ to $R_{13}$ are selected from aryl, aryloxy and thioaryl, in accordance with formula (I) as defined above, then said aryl group, or the aryl group of the aryloxy or thioaryl group, may be substituted or unsubstituted. Where $R_5$ and $R_6$, or $R_6$ and $R_7$, or $R_{12}$ and $R_{13}$, or $R_5$ and $R_{12}$ are linked to form a heterocyclic group, the heterocyclic group may be substituted or unsubstituted. Where substituted, there will generally be 1 to 3 substituents present, preferably 1 substituent. Substituents may include:

carbon-containing groups such as
  alkyl,
  aryl, (e.g. substituted and unsubstituted phenyl (including alkylphenyl, alkoxyphenyl and halophenyl),
  arylalkyl; (e.g. substituted and unsubstituted benzyl);
halogen atoms and halogen containing groups such as
  haloalkyl (e.g. trifluoromethyl),
  haloaryl (e.g. chlorophenyl);
oxygen containing groups such as
  alcohols (e.g. hydroxy, hydroxyalkyl, hydroxyaryl, (aryl)(hydroxy)alkyl),
  ethers (e.g. alkoxy, aryloxy, alkoxyalkyl, aryloxyalkyl, alkoxyaryl, aryloxyaryl),
  aldehydes (e.g. carboxaldehyde),
  ketones (e.g. alkylcarbonyl, arylcarbonyl, alkylcarbonylalkyl, alkylcarbonylaryl, arylcarbonylalkyl, arylcarbonylaryl, arylalkylcarbonyl, arylalkylcarbonylalkyl, arylalkylcarbonylaryl)
  acids (e.g. carboxy, carboxyalkyl, carboxyaryl),
  acid derivatives such as esters
    (e.g. alkoxycarbonyl, aryloxycarbonyl, alkoxycarbonylalkyl, aryloxycarbonylalkyl, alkoxycarbonylaryl, aryloxycarbonylaryl, alkylcarbonyloxy, alkylcarbonyloxyalkyl), amides
    (e.g. aminocarbonyl, mono- or di-alkylaminocarbonyl, cyclicaminocarbonyl, aminocarbonylalkyl, mono- or di-alkylaminocarbonylalkyl, arylaminocarbonyl or arylalkylaminocarbonyl, alkylcarbonylamino, arylcarbonylamino or arylalkylcarbonylamino), carbamates
    (eg. alkoxycarbonylamino, aryloxycarbonylamino, arylalkyloxycarbonylamino, aminocarbonyloxy, mono- or di-alkylaminocarbonyloxy, arylaminocarbonyloxy or arylalkylaminocarbonyloxy) and ureas
    (eg. mono- or di-alkylaminocarbonylamino, arylaminocarbonylamino or arylalkylaminocarbonylamino);
nitrogen containing groups such as
  amines (e.g. amino, mono- or dialkylamino, cyclicamino, arylamino, aminoalkyl, mono- or dialkylaminoalkyl),
  azides,
  nitriles (e.g. cyano, cyanoalkyl),
  nitro,
  sulfonamides (e.g. aminosulfonyl, mono- or di-alkylaminosulfonyl, mono- or di-arylaminosulfonyl, alkyl- or aryl-sulfonylamino, alkyl- or aryl-sulfonyl(alkyl)amino, alkyl- or aryl-sulfonyl(aryl)amino);
sulfur containing groups such as
  thiols, thioethers, sulfoxides, and sulfones
    (e.g. alkylthio, alkylsulfinyl, alkylsulfonyl, alkylthioalkyl, alkylsulfinylalkyl, alkylsulfonylalkyl, arylthio, arylsulfinyl, arylsulfonyl, arylthioalkyl, arylsulfinylalkyl, arylsulfonylalkyl);
heterocyclic groups containing one or more, preferably one, heteroatom,
    (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl); and silicon-containing groups-such as
  silanes (e.g. trialkylsilyl).

In one embodiment, where any of $R_1$ to $R_{13}$ is directly substituted by an alkyl substituent group, or by an alkyl-containing substituent group (such as alkoxy, alkoxyalkyl or alkylcarbonylamino for example), then the alkyl moiety of the substituent group directly attached to any of $R_1$ to $R_{13}$ may be further substituted by the substituent groups hereinbefore described and particularly by halogen, hydroxy, alkoxy, CN, amines (including amino, mono- and di-alkyl amino) and aryl.

In a further embodiment, where any of $R_1$ to $R_{13}$ is directly substituted by an aryl substituent group, or by an aryl-containing substituent group (such as aryloxy or arylaminocarbonylamino for example), then the aryl moiety of the substituent group directly attached to any of $R_1$ to $R_{13}$ may be further substituted by the substituent groups hereinbefore described and particularly by halogen, alkyl (including $CF_3$), hydroxy, alkoxy, CN, amines (including amino, mono- and di-alkyl amino) and $NO_2$.

The terms "directly substituted" and "directly attached", as used herein, mean that the substituent group is bound directly to any of $R_1$ to $R_{13}$ without any intervening divalent atoms or groups.

In the compounds of formula (I), it is preferred that X is S.

In the compounds of formula (I), $R_1$ is selected from H, alkyl (including branched and unbranched alkyl, substituted and unsubstituted alkyl, and cyclic and acyclic alkyl), aryl (including heteroaryl), hydroxy, alkoxy, aryloxy, thioalkyl, thioaryl, halogen, CN, $COR_5$, $CO_2R_5$, $CONR_6R_7$, $CONR_5NR_6R_7$, $NR_6R_7$ (including $NH_2$, monoalkyl amino and dialkylamino), $NR_5CONR_6R_7$, $NR_5COR_6$, $NR_5CO_2R_8$ and $NR_5SO_2R_8$.

It is preferred that $R_1$ is selected from alkyl, alkoxy, thioalkyl, $NR_6R_7$ and $NR_5COR_6$, and preferably from alkyl and $NR_6R_7$. In one embodiment, $R_1$ is selected from $NH_2$.

Where $R_1$ is selected from alkyl, alkoxy and alkylthio, then said alkyl group or the alkyl group of the alkoxy or alkylthio is preferably selected from $C_{1-6}$ alkyl (including branched and unbranched alkyl, substituted and unsubstituted alkyl, and cyclic and acyclic alkyl), preferably saturated $C_{1-6}$ alkyl, and more preferably lower alkyl. In a preferred embodiment, $R_1$ is selected from substituted alkyl, particularly haloalkyl (including $CF_3$) and arylalkyl (including heteroarylalkyl).

In one embodiment, $R_1$ is selected from $CONR_5NR_6R_7$, $NR_5CONR_6R_7$, $NR_5COR_6$, $NR_5CO_2R_8$ and $NR_5SO_2R_8$, and $R_5$ is H or alkyl, and preferably H.

In one embodiment, $R_1$ is selected from $NR_6R_7$ wherein $R_6$ is preferably selected from H and alkyl (preferably H), and $R_7$ is a substituted alkyl group represented by $(CR_9R_{10})_n R_{11}$, wherein $R_9$ and $R_{10}$ are independently selected from H, alkyl and aryl (preferably from H and alkyl, and more preferably from H), n is selected from 1 to 6 (preferably from 2 to 4, more preferably 2), and $R_{11}$ is selected from aryl (including heteroaryl), $COR_5$, $CO_2R_5$, $CONR_{12}R_{13}$, $CONR_5NR_{12}R_{13}$, $NR_{12}R_{13}$ (including $NH_2$, monoalkyl amino and dialkylamino), $NR_5CONR_{12}R_{13}$, $NR_5COR_{12}$, $NR_5CO_2R_8$ and $NR_5SO_2R_8$ (and preferably from aryl (including heteroaryl), $NR_{12}R_{13}$ (including $NH_2$, monoalkyl amino and dialkylamino), $NR_5CONR_{12}R_{13}$, $NR_5COR_{12}$, $NR_5CO_2R_8$ and $NR_5SO_2R_8$), wherein $R_5$ and $R_8$ are as hereinbefore defined and wherein $R_{12}$ and $R_{13}$ are independently selected from H, alkyl and aryl, or where $R_{12}$ and $R_{13}$ are in an $(NR_{12}R_{13})$ group, $R_{12}$ and $R_{13}$ may be linked to form a heterocyclic group, or where $R_5$, $R_{12}$ and $R_{13}$ are in a $(CONR_5NR_{12}R_{13})$ group, $R_5$ and $R_{12}$ may be linked to form a heterocyclic group.

In the compounds of formula (I), $R_2$ is substituted or unsubstituted aryl (including heteroaryl) attached via an unsaturated carbon atom. Preferably, the aryl group is a 5- or 6-membered monocyclic aryl group.

Preferably, $R_2$ is a heteroaryl group, and preferably a heteroaryl group which is attached to the pyrimidine ring of formula (I) such that a heteroatom is adjacent to the unsaturated carbon atom attached to said pyrimidine ring. Preferably, $R_2$ is an N, O or S-containing heteroaryl group. $R_2$ may contain one or more heteroatom(s) selected from N, O and S.

It is preferred that the aryl (including heteroaryl) group of $R_2$ is not ortho,ortho-disubstituted. Preferably, the aryl (including heteroaryl) group of $R_2$ is not substituted at either ortho position. As used herein, reference to ortho-substitution of the $R_2$ group means the ortho positions of the $R_2$ group relative to the point of attachment of $R_2$ to the pyrimidine moiety of formula (I).

In a preferred embodiment, $R_2$ is selected from furyl (including 2-furyl), thienyl (including 2-thienyl), pyridyl (including 2-pyridyl), thiazolyl (including 2- and 5-thiazolyl), pyrazolyl (including 3-pyrazolyl), triazolyl (including 4-triazolyl), pyrrolyl (including 2-pyrrolyl) and oxazolyl (including 5-oxazolyl). In a further embodiment, $R_2$ is selected from 2-furyl, 2-thienyl, 2-thiazolyl, 2-pyridyl, 3-pyrazolyl, 2-pyrrolyl, 4-triazolyl and 5-oxazolyl. In a preferred embodiment, $R_2$ is selected from furyl, thienyl, pyridyl and thiazolyl, and preferably from 2-furyl, 2-thienyl, 2-thiazolyl and 2-pyridyl.

In a particularly preferred embodiment, $R_2$ is selected from 2-thiazolyl, optionally substituted, particularly by methyl.

In the compounds of formula (I), $R_3$ is selected from H, alkyl (including haloalkyl (particularly $CF_3$)), hydroxy, alkoxy (including $OCF_3$), halogen, CN and $NO_2$. Preferably, $R_3$ is selected from H, $CF_3$, hydroxy, alkoxy, halogen, CN and $NO_2$, and preferably $R_3$ is H.

In the embodiment where $R_3$ is selected from alkyl or alkoxy, then said alkyl group or the alkyl group of said alkoxy is preferably $C_{1-6}$ alkyl (including branched and unbranched alkyl, substituted and unsubstituted alkyl, and cyclic and acyclic alkyl), preferably saturated $C_{1-6}$ alkyl, and more preferably lower alkyl. In a preferred embodiment of compounds wherein $R_3$ is selected from alkyl, $R_3$ is haloalkyl (particularly $CF_3$).

In the compounds of formula (I), $R_4$ is selected from H, alkyl (including branched and unbranched alkyl, substituted and unsubstituted alkyl, and cyclic and acyclic alkyl), aryl (including heteroaryl), hydroxy, alkoxy, aryloxy, thioalkyl, thioaryl, halogen, CN, $NO_2$, $COR_5$, $CO_2R_5$, $CONR_6R_7$, $CONR_5NR_6R_7$, $NR_6R_7$ (including $NH_2$), $NR_5CONR_6R_7$, $NR_5COR_6$, $NR_5CO_2R_8$ and $NR_5SO_2R_8$.

Where $R_4$ is selected from alkyl, preferably $R_4$ is $C_{1-6}$ alkyl (including branched and unbranched alkyl, substituted and unsubstituted alkyl, and cyclic and acyclic alkyl), preferably saturated $C_{1-6}$ alkyl, and more preferably lower alkyl. In one embodiment, $R_4$ is selected from substituted alkyl, wherein the substituent groups are selected from halogen, susbtituted and unsubstituted aryl (including heteroaryl), cycloalkyl, non-aromatic heterocyclyl, $CO_2R_5$, $CONR_6R_7$, $CONR_5NR_6R_7$ and $C(=NR_5)NR_6R_7$, preferably aryl (including heteroaryl) and $CONR_6R_7$, more preferably aryl (including heteroaryl). In an alternative embodiment, $R_4$ is selected from substituted alkyl, particularly haloalkyl (including $CF_3$) and arylalkyl (including heteroarylalkyl). In an alternative embodiment, $R_4$ is selected from unsubstituted $C_{1-6}$ alkyl (preferably saturated $C_{1-6}$ alkyl).

In one embodiment $R_4$ is selected from H, alkyl (including arylalkyl (including heteroarylalkyl)), halogen, $COR_5$, $CO_2R_5$, $CONR_6R_7$ and $CONR_5NR_6R_7$, preferably from H, alkyl (including arylalkyl (including heteroarylalkyl)) and halogen, and preferably from H.

In the compounds of formula (I), $R_5$, $R_6$ and $R_7$ are independently selected from H, alkyl (including branched and unbranched alkyl, substituted and unsubstituted alkyl, cyclic and acyclic alkyl) and aryl (including heteroaryl), or where $R_6$ and $R_7$ are in any $NR_6R_7$ group $R_6$ and $R_7$ may be linked to form a heterocyclic group, or where $R_5$, $R_6$ and $R_7$ are in a $CONR_5NR_6R_7$ group, $R_5$ and $R_6$ may be linked to form a heterocyclic group.

In the compounds of formula (I), $R_{12}$ and $R_{13}$ are independently selected from H, alkyl (including branched and unbranched alkyl, substituted and unsubstituted alkyl, cyclic and acyclic alkyl) and aryl (including heteroaryl), or where $R_{12}$ and $R_{13}$ are in any $NR_{12}R_{13}$ group $R_{12}$ and $R_{13}$ may be linked to form a heterocyclic group, or where $R_5$, $R_{12}$ and $R_{13}$ are in a $CONR_5NR_{12}R_{13}$ group, $R_5$ and $R_{12}$ may be linked to form a heterocyclic group.

In the compounds of formula (I), $R_8$ is selected from alkyl (including branched and unbranched alkyl, substituted and unsubstituted alkyl, cyclic and acyclic alkyl) and aryl (including heteroaryl).

Where $R_5$ to $R_{10}$, $R_{12}$ and $R_{13}$, are independently selected from alkyl, preferably $R_5$ to $R_{10}$, $R_{12}$ and $R_{13}$ are independently selected from $C_{1-6}$ alkyl, preferably $C_{1-6}$ saturated alkyl and more preferably from lower alkyl.

Where $R_6$ and $R_7$, or $R_{12}$ and $R_{13}$, are linked to form a heterocyclic ring, said heterocyclic ring may be saturated, partially unsaturated or aromatic, and is preferably saturated. Said heterocyclic ring is preferably a 5, 6 or 7-membered ring, preferably a 5 or 6-membered ring, and may contain one or more further heteroatom(s) preferably selected from N, O and S.

Where $R_5$ and $R_6$, or $R_5$ and $R_{12}$, are linked to form a heterocyclic ring, said heterocyclic ring may be saturated, partially unsaturated or aromatic, and is preferably saturated. Said heterocyclic ring is preferably a 5, 6 or 7-membered ring, preferably a 5 or 6-membered ring, and may contain one or more further heteroatom(s) preferably selected from N, O and S.

In a particularly preferred embodiment of the invention, the compounds of the present invention are selected from:
7-bromo-4(2-furyl)-N-(2-hydroxyethyl)thieno[3,2-d]pyrimidine-2-amine;
N-allyl-4-(2-furyl)thieno[3,2-d]pyrimidine-2-amine;
2-ethyl-4-(2-pyridyl)thieno[3,2-d]pyrimidine;
2-methyl-4-(2-pyridyl)thieno[3,2-d]pyrimidine;
2-n-propyl-4-(2-pyridyl)thieno[3,2-d]pyrimidine;
N-(2-hydroxyethyl)-4-(2-thiazolyl)thieno[3,2-d]pyrimidine-2-amine;
2-isopropyl-4-(2-pyridyl)thieno[3,2-d]pyrimidine;
N-(2-methoxyethyl)-4-(2-furyl)thieno[3,2-d]pyrimidine-2-amine;
N,N-dimethyl-4-(4-methyl-2-thiazolyl)thieno[3,2-d]pyrimidine-2-amine;
4-(2-furyl)thieno[3,2-d]pyrimidine-2-amine;
2-ethyl-4-(4-methyl-2-thiazolyl)thieno[3,2-d]pyrimidine;
2-ethyl-4-(2-thiazolyl)thieno[3,2-d]pyrimidine;
N,N-dimethyl-4-(5-methyl-2-thiazolyl)thieno[3,2-d]pyrimidine-2-amine;
N,N-dimethyl-4-(4,5-dimethyl-2-thiazolyl)thieno[3,2-d]pyridine-2-amine;
4-(2-thiazolyl)thieno[3,2-d]pyrimidine-2-amine;
(2R)-2-(2-hydroxymethylpyrrolidin-1-yl)-4-(2-thiazolyl)thieno[3,2-d]pyrimidine;
N-allyl-4-(2-thiazolyl)thieno[3,2-d]pyrimidine-2-amine;
2-isopropyl-4-(2-thiazolyl)thieno[3,2-d]pyrimidine;
N,N-dimethyl-4-(5-methyl-2-pyridyl)thieno[3,2-d]pyrimidine-2-amine;
2-tert-butyl-4-(2-thiazolyl)thieno[3,2-d]pyrimidine;
2-cyclopropyl-4-(2-thiazolyl)thieno[3,2-d]pyrimidine;
2-ethyl 4-(6-methyl-2-pyridyl)thieno[3,2-d]pyrimidine;
(2S)-2-(2-hydroxymethylpyrrolidin-1-yl)-4-(2-thiazolyl)thieno[3,2-d]pyridine; and
2-(2-chloroethyl)-4-(2-thiazolyl)thieno[3,2-d]pyrimidine.

Where chiral the compounds of the present invention may be in the form of a racemic mixture of pairs of enantiomers or in enantiomerically pure form.

According to a further aspect of the invention, there is provided for use in therapy a compound of the present invention, or a pharmaceutically acceptable salt or prodrug thereof.

The present invention may be employed in respect of a human or animal subject, more preferably a mammal, more preferably a human subject.

The disorders of particular interest are those in which the blocking of purine receptors, partiucularly adenosine receptors and more particularly adenosine $A_{2A}$ receptors, may be beneficial. These may include movement disorders such as Parkinson's disease, drug-induced Parkinsonism, post-encephalitic Parkinsonism, Parkinsonism induced by poisoning (for example MPTP, manganese, carbon monoxide) and post-traumatic Parkinson's disease (punch-drunk syndrome).

Other movement disorders in which the blocking of purine receptors, may be of benefit include progressive supernuclear palsy, Huntingtons disease, multiple system atrophy, corticobasal degeneration, Wilsons disease, Hallerrorden-Spatz disease, progressive pallidal atrophy, Dopa-responsive dystonia-Parkinsonism, spasticity or other disorders of the basal ganglia which result in abnormal movement or posture. The present invention may also be effective in treating Parkinson's with on-off phenomena; Parkinson's with freezing (end of dose deterioration); and Parkinson's with prominent dyskinesias.

The compounds of formula (I) may be used or administered in combination with one or more additional drugs useful in the treatment of movement disorders, such as L-DOPA or a dopamine agonist, the components being in the same formulation or in separate formulations for administration simultaneously or sequentially.

Other disorders in which the blocking of purine receptors, particularly adenosine receptors and more particularly adenosine $A_{2A}$ receptors may be beneficial include acute and chronic pain; for example neuropathic pain, cancer pain, trigeminal neuralgia, migraine and other conditions associated with cephalic pain, primary and secondary hyperalgesia, inflammatory pain, nociceptive pain, tabes dorsalis, phantom limb pain, spinal cord injury pain, central pain, post-herpetic pain and HIV pain; affective disorders including mood disorders such as bipolar disorder, seasonal affective disorder, depression, manic depression, a typical depression and monodepressive disease; central and peripheral nervous system degenerative disorders including corticobasal degeneration, demyelinating disease (multiple sclerosis, disseminated sclerosis), Freidrich's ataxia, motoneurone disease (amyotrophic lateral sclerosis, progressive bulbar atrophy), multiple system atrophy, myelopathy, radiculopathy, peripheral neuropathy (diabetic neuropathy, tabes dorsalis, drug-induced neuropathy, vitamin deficiency), systemic lupus erythamatosis, granulomatous disease, olivo-ponto-cerebellar atrophy, progressive pallidal atrophy, progressive supranuclear palsy, spasticity; schizophrenia and related pyshoses; cognitive disorders including dementia, Alzheimers Disease, Frontotemporal dementia, multi-infarct dementia, AIDS dementia, dementia associated with Huntingtons Disease, Lewy body dementia, senile dementia, age-related memory impairment, cognitive impairment associated with dementia, Korsakoff syndrome, dementia pugilans; attention disorders such as attention-deficit hyperactivity disorder (ADHD), attention deficit disorder, minimal brain dysfunction, brain-injured child syndrome, hyperkinetic reaction childhood, and hyperactive child syndrome; central nervous system injury including traumatic brain injury, neurosurgery (surgical trauma), neuroprotection for head injury, raised intracranial pressure, cerebral oedema, hydrocephalus, spinal cord injury; cerebral ischaemia including transient ischaemic attack, stroke (thrombotic stroke, ischaemic stroke, embolic stroke, haemorrhagic stroke, lacunar stroke) subarachnoid haemorrhage, cerebral vasospasm, neuroprotection for stroke, peri-natal asphyxia, drowning, cardiac arrest, subdural haematoma; myocardial ischaemia; muscle ischaemia; sleep disorders such as hypersomnia and narcolepsy; eye disorders such as retinal ischaemia-reperfusion injury and diabetic neuropathy; cardiovascular disorders such as claudication and hypotension; and diabetes and its complications.

According to a further aspect of the present invention, there is provided the use of a compound of the present invention or a pharmaceutically acceptably salt or prodrug thereof in the manufacture of a medicament for the treatment or prevention of a disorder in which the blocking of purine receptors, particularly adenosine receptors and more particularly $A_{2A}$ receptors, may be beneficial.

According to a further aspect of the present invention there is provided a method of treating or preventing a disorder in which the blocking of purine receptors, particularly adenosine receptors and more particularly adenosine $A_{2A}$ receptors, may be beneficial, the method comprising administration to a subject in need of such treatment an effective dose of a compound of the present invention or a pharmaceutically acceptable salt or prodrug thereof.

The disorder may be caused by the hyperfunctioning of the purine receptors.

According to a further aspect of the present invention there is provided use of a compound of the present invention or a pharmaceutically acceptable salt or prodrug thereof in the manufacture of a medicament for the treatment or prevention of movement disorders in a subject.

According to a further aspect of the invention there is provided a method of treating or preventing movement disorders comprising administration to a subject in need of such treatment an effective dose of a compound of the present invention or a pharmaceutically acceptable salt or prodrug thereof.

According to a further aspect of the invention there is provided use of a compound of the present invention or a pharmaceutically acceptable salt or prodrug thereof in the manufacture of a medicament for neuroprotection in a subject.

According to a further aspect of the invention there is provided a method of neuroprotection comprising administration to a subject in need of such treatment an effective dose of a compound of the present invention or a pharmaceutically acceptable salt or prodrug thereof.

The medicament for or method of neuroprotection may be of use in the treatment of subjects who are suffering from or at risk from a neurodegenerative disorder, such as a movement disorder.

According to a further aspect of the invention, there is provided a method of preparing the novel compounds of the present invention. Compounds of formula (I) may be prepared according to conventional synthetic methods, such as set out in Reaction Scheme 1.

Reaction Scheme 1

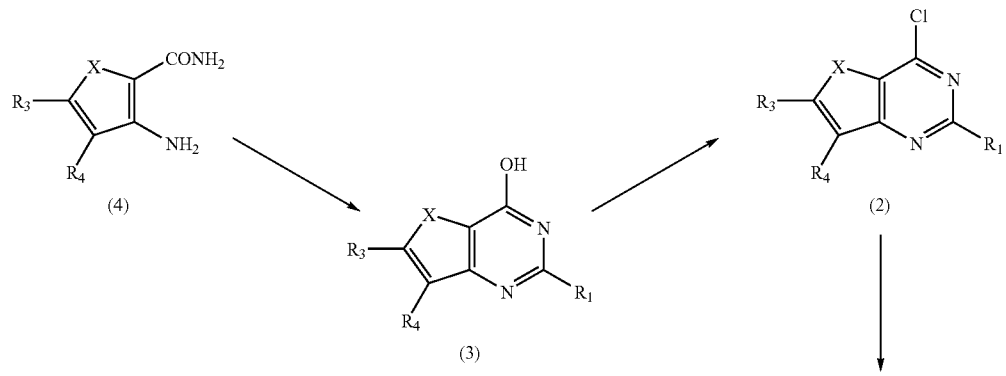

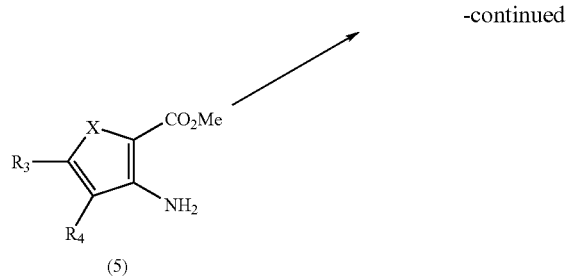

(5)

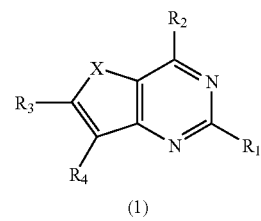

(1)

Compounds of formula (1) are prepared from halides of formula (2) by standard methods such as aryl coupling reactions which may be advantageously carried out in the presence of a catalyst such as a palladium catalyst. The aryl coupling reaction may be carried out by reaction of a halide of formula (2) with, for example, an aryl or heteroaryl trialkyltin reagent, an aryl or heteroaryl boronic acid or boronic ester reagent or an aryl or heteroaryl zinc halide reagent according to methods described in the literature. Suitable aryl or heteroaryl trialkyl tin, boronic acid, boronic ester or zinc halide reagents are either commercially available or may be prepared by standard literature methods.

Halides of formula (2) are either known in the literature or may be prepared from compounds of formula (3) by standard methods, for example by treatment with a chlorinating reagent such as $POCl_3$. Compounds of formula (3) are either known in the literature or may be prepared from compounds of formula (4) by standard methods such as treatment with an appropriate ester ($R_1CO_2Et$) in the presence of a suitable base such as NaOEt, or by treatment with an appropriate anhydride ($R_1CO)_2O$ in the presence of a base such as $Et_3N$ followed by heating in the presence of a stronger base such as NaOH. Alternatively compounds of formula (3) may be prepared from compounds of formula (5) by standard methods such as treatment with an appropriate nitrile ($R_1CN$) in the presence of dry HCl gas. Compounds of formula (4) and formula (5) are either known in the literature or may be prepared by standard methods.

Compounds of formula (1) where $R_1$ is $NR_6R_7$ may be prepared from compounds of formula (1) where $R_1$ is halogen by standard methods such as reaction with an appropriate amine ($R_6R_7NH$). Compounds of formula (1) where $R_1$ is halogen may be prepared from compounds of formula (2) where $R_1$ is halogen as described above. Compounds of formula (2) where $R_1$ is halogen are either known in the literature or may be prepared by methods analogous to those described in the literature.

Compounds of formula (1) where $R_1$ is $NR_5CONR_6R_7$, $NR_5COR_6$, $NR_5CO_2R_8$ or $NR_5SO_2R_8$ wherein $R_5$ is H may be prepared from compounds of formula (1) where $R_1$ is $NH_2$ by standard methods for example by treatment with an appropriate isocyanate ($R_6NCO$ or $R_7NCO$), carbamoyl chloride ($R_6R_7NCOCl$), acid chloride ($R_6COCl$), chloroformate ($ClCO_2R_8$) or sulphonyl chloride ($ClSO_2R_8$). Analogous compounds wherein $R_5$ is alkyl may be prepared by initial alkylation or reductive alkylation followed by reaction with the appropriate reagent as described above.

Compounds of formula (1) where $R_1$ is $NH_2$ may be prepared from compounds of formula (1) where $R_1$ is halogen either by direct displacement with ammonia or by reaction with an appropriate protected amine, for example 3,4-dimethoxybenzylamine, followed by removal of the protecting group, if desired, by treatment with TFA.

Compounds of formula (1) where $R_1$ is hydroxy, alkoxy, aryloxy, thioalkyl, thioaryl, or CN may be prepared from compounds of formula (1) where $R_1$ is halogen by direct displacement with an appropriate nucleophile such as water, an alcohol, thiol or cyanide in the presence of a suitable base.

Compounds of formula (1) where $R_1$ is $CONR_6R_7$ or $CONR_5NR_6R_7$ may be prepared from compounds of formula (1) where $R_1$ is $CO_2R_5$ by standard methods such as reaction with an appropriate amine ($R_6R_7NH$) or substituted hydrazine ($HNR_5N_6R_7$), either directly or in the presence of a suitable reagent such as trimethylaluminium.

Compounds of formula (1) where $R_1$ is $COR_5$, wherein $R_5$ is H, may be prepared from compounds of formula (1) where $R_1$ is $CO_2R_5$ by standard methods such as reduction with an appropriate reducing agent such as DIBAL at low temperature. Compounds of formula (1) where $R_1$ is $COR_5$, wherein $R_5$ is alkyl or aryl, may be prepared from compounds of formula (1) where $R_1$ is $COR_5$, wherein $R_5$ is H, by standard methods such as initial treatment with an appropriate alkyl or aryllithium or Grignard reagent, followed by oxidation.

Compounds of formula (1) where $R_1$ is $CO_2R_5$ may be prepared according to Reaction Scheme 1 by the methods described above.

In a compound of formula (1) where $R_1$ is alkyl or aryl or where the group $R_1$ contains an alkyl or aryl substituent, the alkyl or aryl group may be substituted as defined above. Where the alkyl or aryl group is substituted by a reactive functional group it will be appreciated that derivatisation of the reactive functional group may lead to a wide variety of additional substituent groups. By way of example where the alkyl or aryl group is substituted by an amino group then the amino group may be derivatised to form a mono- or dialkylamine, urea, thiourea, amide, carbamate or sulphonamide by the use of standard reactions such as those described above. Where the alkyl or aryl group is substituted by an amino group it may be advantageous to protect the amino group during the synthesis by the use of a standard protecting group such as a BOC group. The protecting group may then be removed at the appropriate step in the synthesis, by standard methods such as treatment with TFA.

Compounds of formula (1) where $R_3$ is halogen or $NO_2$ may be prepared from compounds of formula (2) where $R_3$ is halogen or $NO_2$ as described above. Compounds of formula (2) where $R_3$ is halogen or $NO_2$ are either known in the literature or may be prepared from compounds of formula (2) where $R_3$ is H by standard literature methods such as halogenation or nitration.

Compounds of formula (1) where $R_3$ is hydroxy, alkoxy or cyano may be prepared from compounds of formula (2) where $R_3$ is hydroxy, alkoxy or cyano as described above. Compounds of formula (2) where $R_3$ is hydroxy, alkoxy or cyano may be prepared from compounds of formula (2) where $R_3$ is halogen by standard literature methods such as nucleophilic displacement.

Compounds of formula (1) where $R_4$ is aryl or heteroaryl may be prepared from compounds of formula (1) where $R_4$ is halogen by standard methods such as palladium catalysed aryl coupling reactions as described above. Compounds of formula (1) where $R_4$ is halogen are prepared from compounds of formula (2) where $R_4$ is halogen as described above. Compounds of formula (2) where $R_4$ is halogen are either known in the literature or prepared by methods analogous to those described in the literature.

Compounds of formula (1) where $R_4$ is $NH_2$ are prepared from compounds of formula (1) where $R_4$ is $NO_2$ by standard methods such as reduction. Compounds of formula (1) where $R_4$ is $NO_2$ are prepared from compounds of formula (2) where $R_4$ is $NO_2$ as described above. Compounds of formula (2) where $R_4$ is $NO_2$ are either known in the literature or prepared by methods analogous to those described in the literature.

Compounds of formula (1) where $R_4$ is $NR_6R_7$, $NR_5CONR_6R_7$, $NR_5COR_6$, $NR_5CO_2R_8$ or $NR_5SO_2R_8$ wherein $R_5$ is H may be prepared from compounds of formula (1) where $R_4$ is $NH_2$ by standard methods for example by mono- or dialkylation, reductive alkylation or by treatment with an appropriate isocyanate ($R_6NCO$ or $R_7NCO$), carbamoyl chloride ($R_6R_7NCOCl$), acid chloride ($R_6COCl$), chloroformate ($ClCO_2R_8$) or sulphonyl chloride ($ClSO_2R_8$). Analogous compounds wherein $R_5$ is alkyl may be prepared by initial alkylation or reductive alkylation followed by reaction with the appropriate reagent as described above.

Compounds of formula (1) where $R_4$ is $COR_5$ may be prepared from compounds of formula (2) where $R_4$ is $COR_5$ as described above. Compounds of formula (2) where $R_1$ is $COR_5$ may be prepared from compounds of formula (2) where $R_4$ is H by standard methods such as Friedel-Crafts acylation.

Compounds of formula (1) where $R_4$ is $CO_2R_5$, $CONR_6R_7$ or $CONR_5NR_6R_7$ may be prepared from compounds of formula (2) where $R_4$ is $CO_2R_5$, $CONR_6R_7$ or $CONR_5NR_6R_7$ as described above. Compounds of formula (2) where $R_4$ is $CO_2R_5$ or $CONR_6R_7$ may be prepared from compounds of formula (2) where $R_4$ is halogen by standard methods such as palladium catalysed carbonylation reactions in the presence of an appropriate alcohol ($R_5OH$) or amine ($HNR_6R_7$). Compounds of formula (2) where $R_4$ is $CONR_6R_7$ or $CONR_5NR_6R_7$ may be prepared from compounds of formula (2) where $R_4$ is $CO_2R_5$ by standard methods such as reaction with a suitable amine ($HNR_6R_7$) or hydrazine ($HNR_5NR_6R_7$) derivative.

Compounds of formula (1) where $R_4$ is cyano may be prepared from compounds of formula (1) where $R_4$ is $CONR_6R_7$, wherein $R_6$ and $R_7$ are both H, by standard literature methods such as dehydration.

Compounds of formula (1) where $R_4$ is hydroxy, alkoxy, aryloxy, thioalkyl or thioaryl may be prepared by standard literature methods known to those skilled in the art. Such standard methods may include treatment of a compound of formula (1) where $R_4$ is halogen with an appropriate nucleophile. Alternatively compounds of formula (1) where $R_4$ is hydroxy or alkoxy may be prepare from a compound of formula (1) where $R_4$ is $COR_5$ by use of the Bayer Villiger reaction, followed by a hydrolysis step and followed, if desired, by an alkylation step.

According to a further aspect of the invention, there is provided a pharmaceutical composition comprising a compound of the present invention in combination with a pharmaceutically acceptable carrier or excipient and a method of making such a composition comprising combining a compound of the present invention with a pharmaceutically acceptable carrier or excipient.

The pharmaceutical compositions employed in the present invention comprise a compound of the present invention, or pharmaceutically acceptable salts or prodrugs thereof, and may also contain a pharmaceutically acceptable carrier and optionally other therapeutic ingredients known to those skilled in the art. The term, "pharmaceutically acceptable salts", refers to salts prepared from pharmaceutically acceptable non-toxic acids including inorganic acids and organic acids.

Where the compounds of the present invention are basic, salts may be prepared from pharmaceutically acceptable non-toxic acids including inorganic and organic acids. Such acids include acetic, benzenesulfonic, benzoic, camphorsulfonic, citric, ethenesulfonic, fumaric, gluconic, glutamic, hippuric, hydrobromic, hydrochloric, isethionic, lactic, maleic, malic, mandelic, methanesulfonic, mucic, nitric, pamoic, pantothenic, phosphoric, succinic, sulfuric, tartaric, oxalic, p-toluenesulfonic and the like. Particularly preferred are hydrochloric, hydrobromic, phosphoric, and sulfuric acids, and most particularly preferred is the hydrochloride salt.

Any suitable route of administration may be employed for providing the patient with an effective dosage of a compound of the present invention. For example, oral, rectal, parenteral (intravenous, intramuscular), transdermal, subcutaneous, and the like may be employed. Dosage forms include tablets, troches, dispersions, suspensions, solutions, capsules, patches, and the like. The most suitable route in any given case will depend on the severity of the condition being treated. The most preferred route of administration of the present invention is the oral route. The compositions may be conveniently presented in unit dosage form and prepared by any of the methods well known in the art of pharmacy.

In practical use, the compounds of the present invention can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (e.g. intravenous). In preparing the compositions for oral dosage form, any of the usual pharmaceutical media may be employed as carriers, such as, for example, water, glycols, oils, alcohols, flavouring agents, preservatives, colouring agents, and the like in the case of oral liquid preparations (such as suspensions, solutions and elixirs) or aerosols; or carriers such as starches, sugars, micro-crystalline cellulose, diluents, granulating agents, lubricants, binders, disintegrating agents, and the like may be used in the case of oral solid preparations such as, for example, powders, capsules, and tablets, with the solid oral preparations being preferred over the liquid preparations. The most preferred solid oral preparation is tablets.

Because of their ease of administration, tablets and capsules represent the most advantageous oral dosage unit form in which case solid pharmaceutical carriers are employed. If desired, tablets may be coated by standard aqueous or non-aqueous techniques.

In addition to the common dosage forms set out above, the compounds of the present invention may also be administered by controlled release means and/or delivery devices such as those described in U.S. Pat. Nos. 3,845,770; 3,916, 899; 3,536,809; 3,598,123; 3,630,200; 4,008,719; 4,687,660; and 4,769,027, the disclosures of which are hereby incorporated by reference.

Pharmaceutical compositions employed in the present invention suitable for oral administration may be presented as discrete units such as capsules, cachets, or tablets, or aerosol sprays each containing a predetermined amount of the active ingredient as a powder or granules, a solution or a suspension in an aqueous liquid, an oil-in-water emulsion, or a water-in-oil liquid emulsion. Such compositions may be prepared by any of the methods of pharmacy, but all methods include the step of bringing the active ingredient into association with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or moulding, optionally with one or more accessory ingredients. Compressed tablets may be prepared by compressing in a suitable machine the active ingredient in a free-flowing form such as powder or granules, optionally mixed with a binder, a lubricant, an inert diluent, and/or a surface active or dispersing agent. Moulded tablets may be made by moulding in a suitable machine a mixture of the powdered compound moistened with an inert liquid diluent.

The invention is further defined by reference to the following examples. It will be apparent to those skilled in the art that many modifications, both to materials and methods, may be practised without departing from the purpose and interest of this invention.

EXAMPLES

Synthetic Examples

The invention is illustrated with reference to the following Examples, as set out in Table 1. The syntheses of the Examples are performed using the general Synthetic Methods described hereinafter. The Method used for each Example is given in parentheses in column 1 of Table 1. Analytical data are given in Table 2.

TABLE 1

| Example | Structure | Compound Name |
|---|---|---|
| 1 (A) | 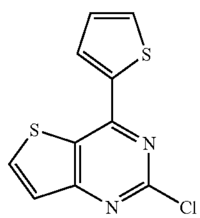 | 2-chloro-4-(2-thienyl)thieno[3,2-d]pyrimidine |
| 2 (E) | 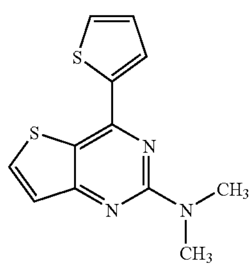 | N,N-dimethyl-4-(2-thienyl)thieno[3,2-d]pyrimidine-2-amine |
| 3 (A) | 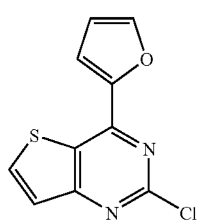 | 2-chloro-4-(2-furyl)thieno[3,2-d]pyrimidine |
| 4 (E) | 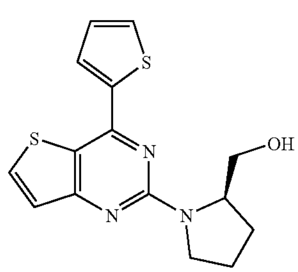 | (2R)-2-(2-hydroxymethylpyrrolidin-1-yl)-4-(2-thienyl)thieno[3,2-d]pyrimidine |

TABLE 1-continued

| Example | Structure | Compound Name |
|---|---|---|
| 5 (E) | 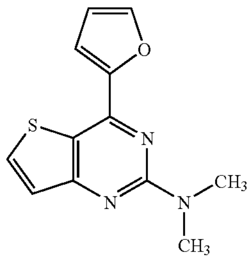 | N,N-dimethyl-4-(2-furyl)thieno[3,2-d]pyrimidine-2-amine |
| 6 (E) | 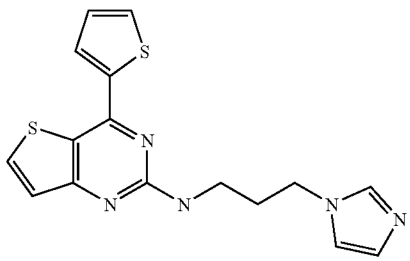 | N-(3-(1H-imidazol-1-yl)propyl)-4-(2-thienyl)thieno[3,2-d]pyrimidine-2-amine |
| 7 (E) | 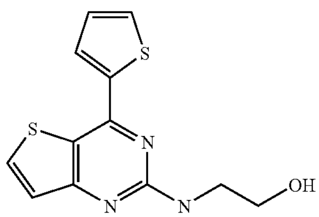 | N-(2-hydroxyethyl)-4-(2-thienyl)thieno[3,2-d]pyrimidine-2-amine |
| 8 (E) | 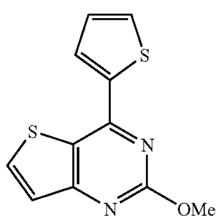 | 2-methoxy-4-(2-thienyl)thieno[3,2-d]pyrimidine |
| 9 (B) | 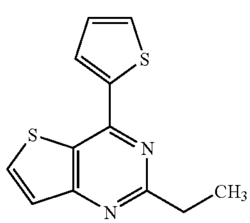 | 2-ethyl-4-(2-thienyl)thieno[3,2-d]pyrimidine |
| 10 (E) | 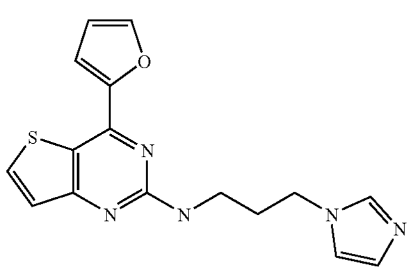 | N-(3-(1H-imidazol-1-yl)propyl)-4-(2-furyl)thieno[3,2-d]pyrimidine-2-amine |

TABLE 1-continued

| Example | Structure | Compound Name |
|---|---|---|
| 11 (A) | 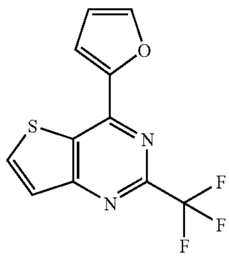 | 4-(2-furyl)-2-trifluoromethylthieno[3,2-d]pyrimidine |
| 12 (A) | 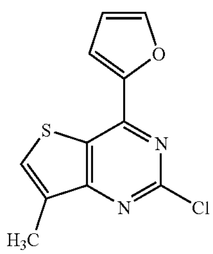 | 2-chloro-4-(2-furyl)-7-methylthieno[3,2-d]pyrimidine |
| 13 (A) | 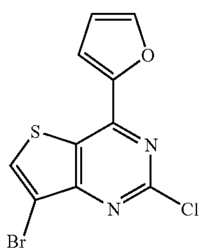 | 7-bromo-2-chloro-4-(2-furyl)thieno[3,2-d]pyrimidine |
| 14 (E) | 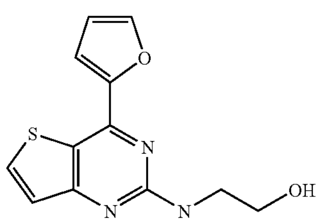 | 4-(2-furyl)-N-(2-hydroxyethyl)thieno[3,2-d]pyrimidine-2-amine |
| 15 (E) | 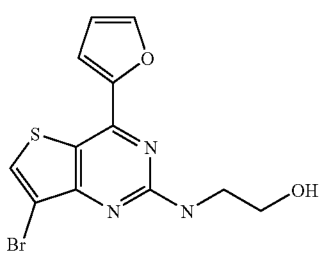 | 7-bromo-4-(2-furyl)-N-(2-hydroxyethyl)thieno[3,2-d]pyrimidine-2-amine |
| 16 (E) | 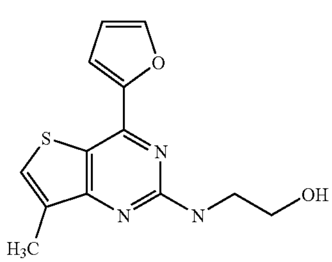 | 4-(2-furyl)-N-(2-hydroxyethyl)-7-methylthieno[3,2-d]pyrimidine-2-amine |

TABLE 1-continued

| Example | Structure | Compound Name |
|---------|-----------|---------------|
| 17 (A) | 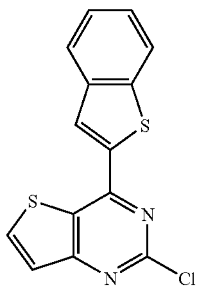 | 4-(2-benzothiophenyl)-2-chlorothieno[3,2-d]pyrimidine |
| 18 (A) | 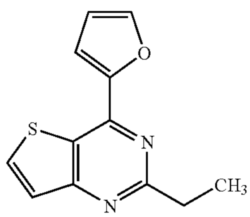 | 2-ethyl-4-(2-furyl)thieno[3,2-d]pyrimidine |
| 19 (E) | 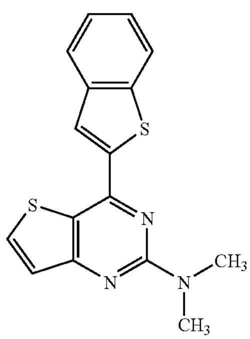 | 4-(2-benzothiophenyl)-N,N-dimethylthieno[3,2-d]pyrimidine-2-amine |
| 20 (E) | 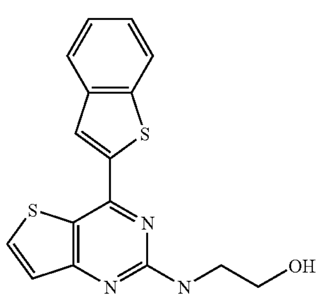 | 4-(2-benzothiophenyl)-N-(2-hydroxyethyl)thieno[3,2-d]pyrimidine-2-amine |
| 21 (E) | 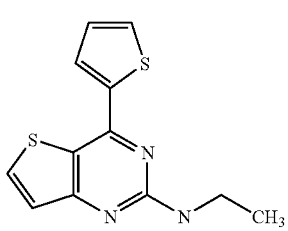 | N-ethyl-4-(2-thienyl)thieno[3,2-d]pyrimidine-2-amine |

TABLE 1-continued

| Example | Structure | Compound Name |
|---|---|---|
| 22 (E) | 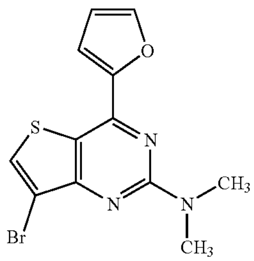 | 7-bromo-N,N-dimethyl-4-(2-furyl)thieno[3,2-d]pyrimidine-2-amine |
| 23 (E) | 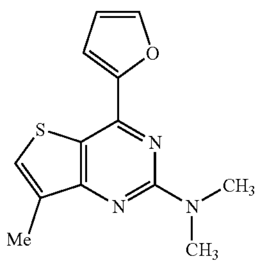 | 4-(2-furyl)-7,N,N-trimethylthieno[3,2-d]pyrimidine-2-amine |
| 24 (A) | 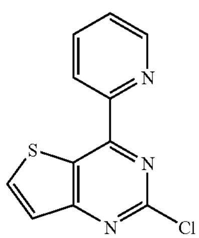 | 2-chloro-4-(2-pyridyl)thieno[3,2-d]pyrimidine |
| 25 (E) | 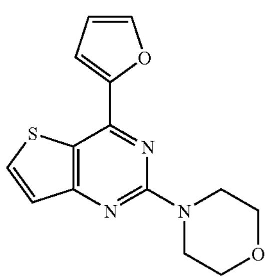 | 4-(2-furyl)-2-morpholinothieno[3,2-d]pyrimidine |
| 26 (E) | 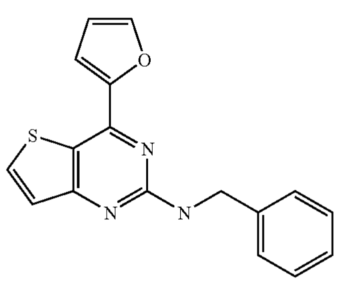 | N-benzyl-4-(2-furyl)thieno[3,2-d]pyrimidine-2-amine |

TABLE 1-continued

| Example | Structure | Compound Name |
|---|---|---|
| 27 (E) | 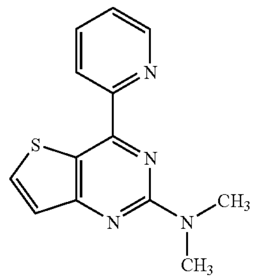 | N,N-dimethyl-4-(2-pyridyl)thieno[3,2-d]pyrimidine-2-amine |
| 28 (B) | 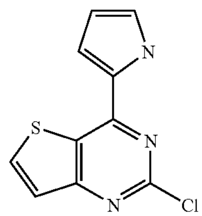 | 2-chloro-4-(1H-pyrrol-1-yl)thieno[3,2-d]pyrimidine |
| 29 (A) | 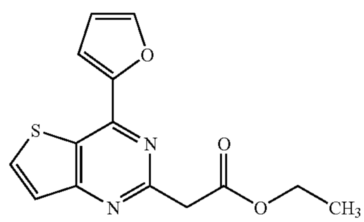 | Ethyl 4-(2-furyl)thieno[3,2-d]pyrimidine-2-acetate |
| 30 (A) | 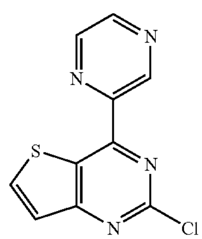 | 2-chloro-4-(2-pyrazinyl)thieno[3,2-d]pyrimidine |
| 31 (P) | 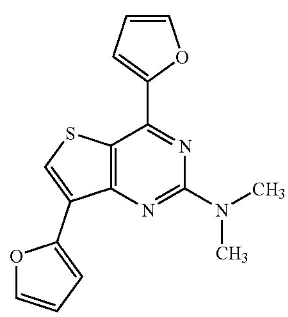 | 4,7-bis(2-furyl)-N,N-dimethylthieno[3,2-d]pyrimidine-2-amine |
| 32 (E) | 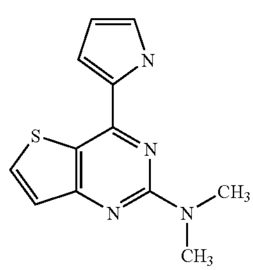 | N,N-dimethyl-4-(1H-pyrrol-1-yl)thieno[3,2-d]pyrimidine-2-amine |

TABLE 1-continued

| Example | Structure | Compound Name |
|---|---|---|
| 33 (E) | 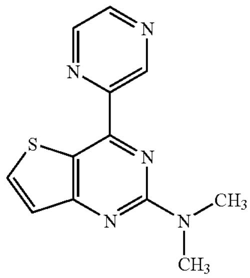 | N,N-dimethyl-4-(2-pyrazinyl)thieno[3,2-d]pyrimidine-2-amine |
| 34 (E) | 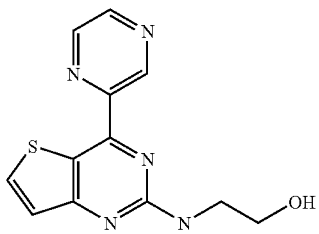 | N-(2-hydroxyethyl)-4-(2-pyrazinyl)thieno[3,2-d]pyrimidine-2-amine |
| 35 (E) | 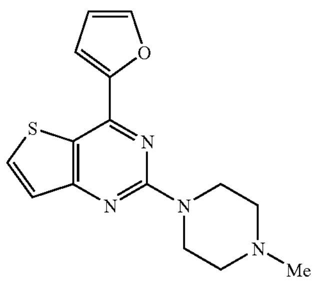 | 4-(2-furyl)-2-(4-methylpiperazinyl)thieno[3,2-d]pyrimidine |
| 36 (E) | 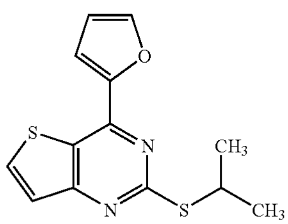 | 4-(2-furyl)-2-isopropylthiothieno[3,2-d]pyrimidine |
| 37 (E) | 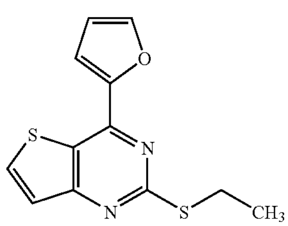 | 2-ethylthio-4-(2-furyl)thieno[3,2-d]pyrimidine |
| 38 (E) | 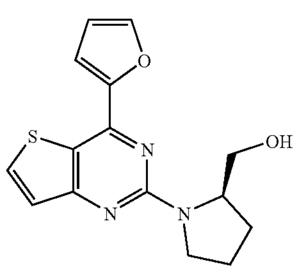 | (2R)-4-(2-furyl)-2-(2-hydroxymethylpyrrolidin-1-yl)thieno[3,2-d]pyrimidine |

TABLE 1-continued

| Example | Structure | Compound Name |
|---|---|---|
| 39 (E) | 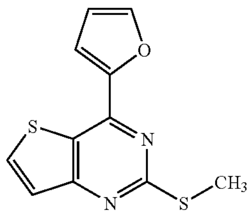 | 4-(2-furyl)-2-methylthiothieno[3,2-d]pyrimidine |
| 40 (E) | 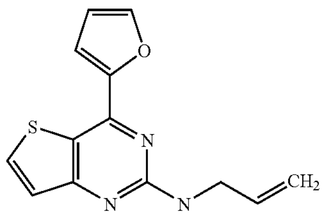 | N-allyl-4-(2-furyl)thieno[3,2-d]pyrimidine-2-amine |
| 41 (A) | 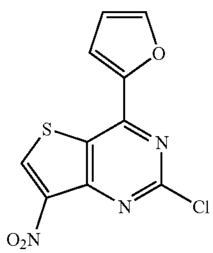 | 2-chloro-4-(2-furyl)-7-nitrothieno[3,2-d]pyrimidine |
| 42 (E) | 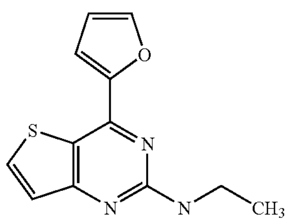 | N-ethyl-4-(2-furyl)thieno[3,2-d]pyrimidine-2-amine |
| 43 (E) | 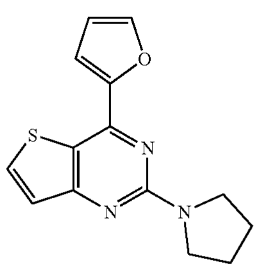 | 4-(2-furyl)-2-(pyrrolidin-1-yl)thieno[3,2-d]pyrimidine |
| 44 (E) | 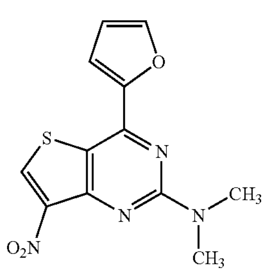 | N,N-dimethyl-4-(2-furyl)-7-nitrothieno[3,2-d]pyrimidine-2-amine |

TABLE 1-continued

| Example | Structure | Compound Name |
|---|---|---|
| 45 (E) | 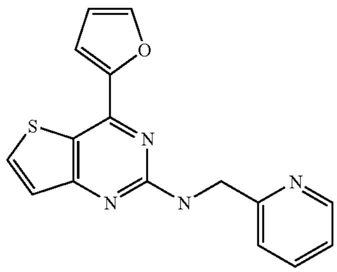 | 4-(2-furyl)-N-(2-pyridylmethyl)thieno[3,2-d]pyrimidine-2-amine |
| 46 (A) | 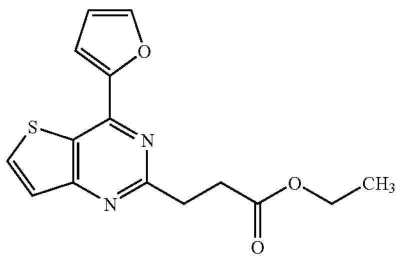 | Ethyl 3-(4-(2-furyl)thieno[3,2-d]pyrimidine-2-yl)propionate |
| 47 (E) | 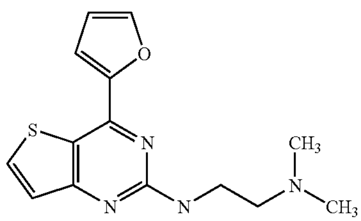 | N-(2-dimethylaminoethyl)4-(2-furyl)thieno[3,2-d]pyrimidine-2-amine |
| 48 (K) | 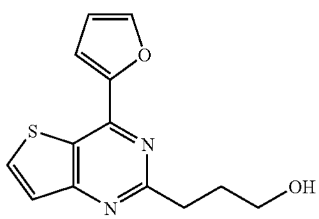 | 3-(4-(2-furyl)thieno[3,2-d]pyrimidin-2-yl)propanol |
| 49 (M) | 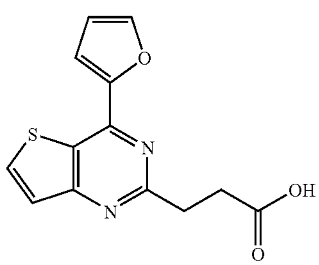 | 3-(4-(2-furyl)thieno[3,2-d]pyrimidine-2-yl)propionic acid |
| 50 (N) | 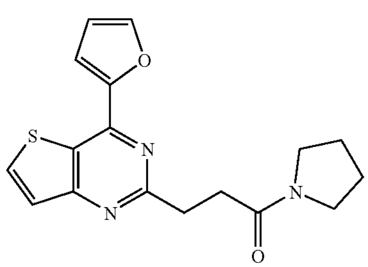 | 4-(2-furyl)-2-(3-oxo-3-(1-pyrrolidinyl)propyl)thieno[3,2-d]pyrimidine |

TABLE 1-continued

| Example | Structure | Compound Name |
| --- | --- | --- |
| 51 (J) | 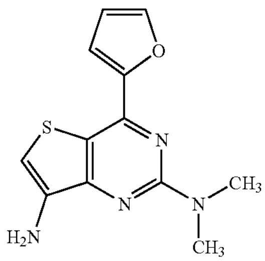 | 7-amino-N,N-dimethyl-4-(2-furyl)thieno[3,2-d]pyrimidine-2-amine |
| 52 (C) | 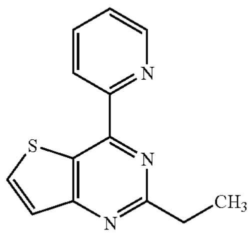 | 2-ethyl-4-(2-pyridyl)thieno[3,2-d]pyrimidine |
| 53 (E) | 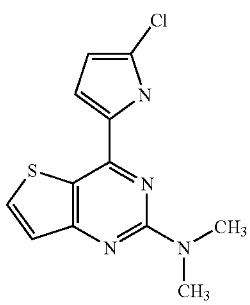 | 4-(5-chloro-2-thienyl)-N,N-dimethylthieno[3,2-d]pyrimidine-2-amine |
| 54 (K) | 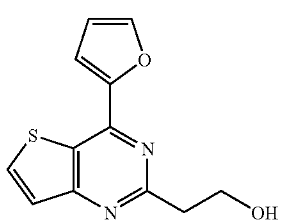 | 2-(4-(2-furyl)thieno[3,2-d]pyrimidin-2-yl)ethanol |
| 55 (I) | 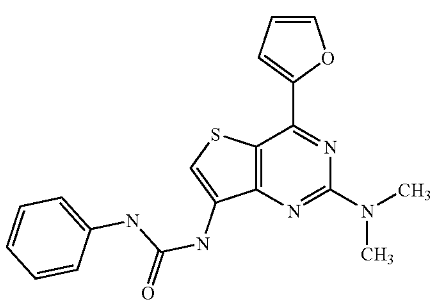 | N-(2-dimethylamino-4-(2-furyl)thieno[3,2-d]pyrimidine-7-yl)-N'-phenylurea |

TABLE 1-continued

| Example | Structure | Compound Name |
| --- | --- | --- |
| 56 (G) | 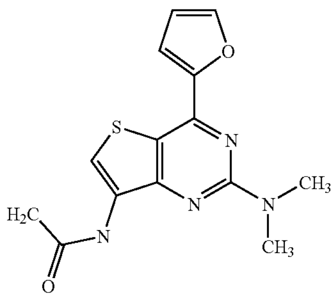 | N-(2-dimethylamino-4-(2-furyl)thieno[3,2-d]pyrimidine-7-yl)acetamide |
| 57 (G) | 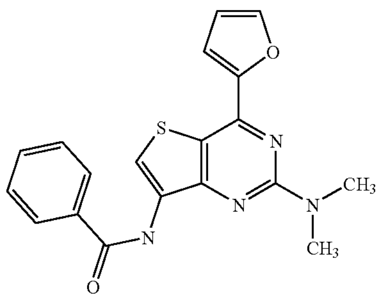 | N-(2-dimethylamino-4-(2-furyl)thieno[3,2-d]pyrimidine-7-yl)benzamide |
| 58 (E) | 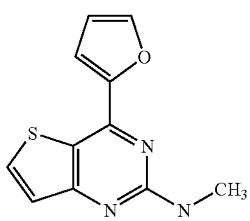 | 4-(2-furyl)-N-methylthieno[3,2-d]pyrimidine-2-amine |
| 59 (G) | 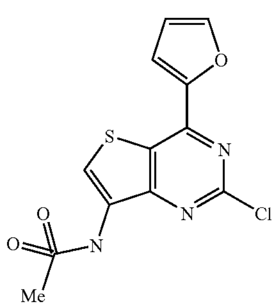 | N-(2-chloro-4-(2-furyl)thieno[3,2-d]pyrimidine-7-yl)methanesulphonamide |
| 60 (G) | 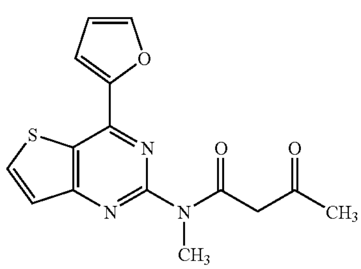 | N-(4-(2-furyl)thieno[3,2-d]pyrimidine-2-yl)-N-methyl-3-oxobutanamide |

TABLE 1-continued

| Example | Structure | Compound Name |
|---|---|---|
| 61 (E) | 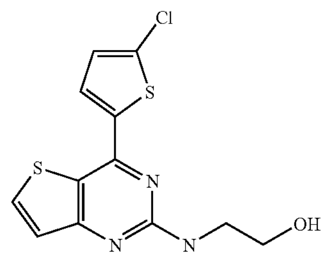 | 4-(5-chloro-2-thienyl)-N-(2-hydroxyethyl)thieno[3,2-d]pyrimidine-2-amine |
| 62 (C) | 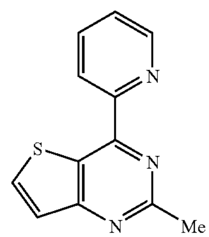 | 2-methyl-4-(2-pyridyl)thieno[3,2-d]pyrimidine |
| 63 (C) | 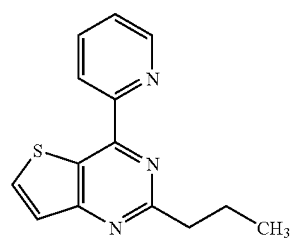 | 2-n-propyl-4-(2-pyridyl)thieno[3,2-d]pyrimidine |
| 64 (C) | 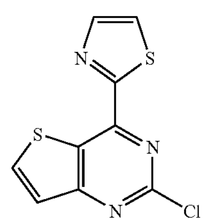 | 2-chloro-4-(2-thiazolyl)thieno[3,2-d]pyrimidine |
| 65 (E) | 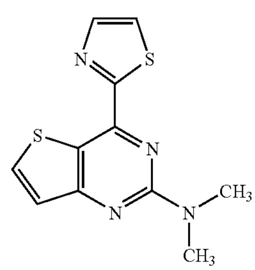 | N,N-dimethyl-4-(2-thiazolyl)thieno[3,2-d]pyrimidine-2-amine |
| 66 (C) | 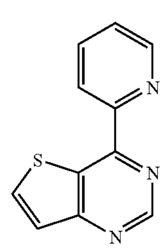 | 4-(2-pyridyl)thieno[3,2-d]pyrimidine |

TABLE 1-continued

| Example | Structure | Compound Name |
| --- | --- | --- |
| 67 (E) | 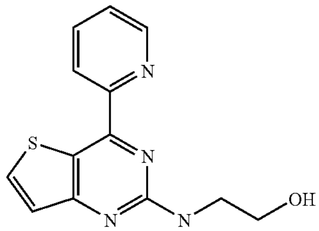 | N-(2-hydroxyethyl)-4-(2-pyridyl)thieno[3,2-d]pyrimidine-2-amine |
| 68 (E) | 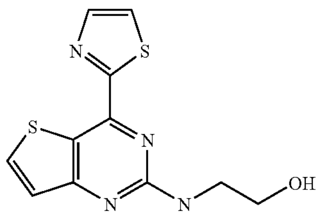 | N-(2-hydroxyethyl)-4-(2-thiazolyl)thieno[3,2-d]pyrimidine-2-amine |
| 69 (L) | 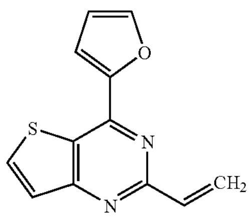 | 4-(2-furyl)-2-vinylthieno[3,2-d]pyrimidine |
| 70 (C) | 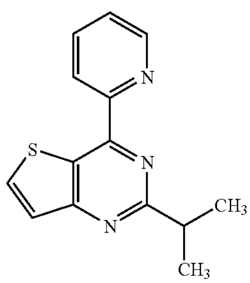 | 2-isopropyl-4-(2-pyridyl)thieno[3,2-d]pyrimidine |
| 71 (E) | 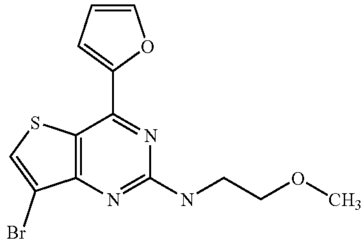 | N-(2-methoxyethyl)-4-(2-furyl)thieno[3,2-d]pyrimidine-2-amine |
| 72 (E) | 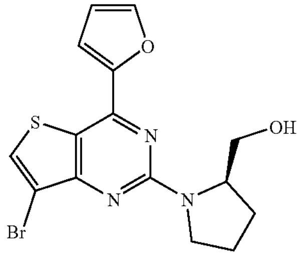 | (2R)-7-bromo-4-(2-furyl)-2-(2-hydroxymethylpyrrolidin-1-yl)thieno[3,2-d]pyrimidine |

TABLE 1-continued

| Example | Structure | Compound Name |
| --- | --- | --- |
| 73 (A) | 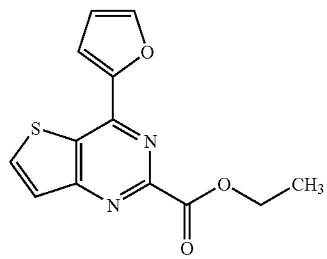 | Ethyl 4-(2-furyl)thieno[3,2-d]pyrimidine-2-carboxylate |
| 74 (E) | 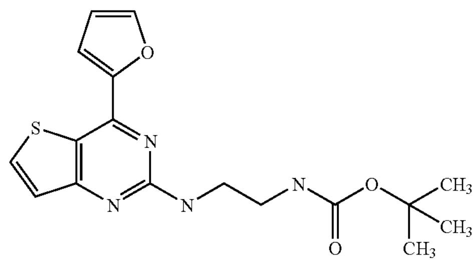 | tert-butyl (2-(4-(2-furyl)thieno[3,2-d]pyrimidine-2-ylamino)ethyl)carbamate |
| 75 (F) | 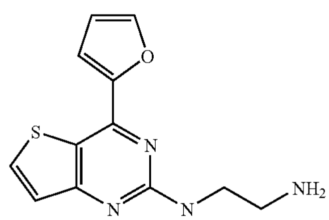 | N-(2-aminoethyl)-4-(2-furyl)thieno[3,2-d]pyrimidine-2-amine |
| 76 (E) | 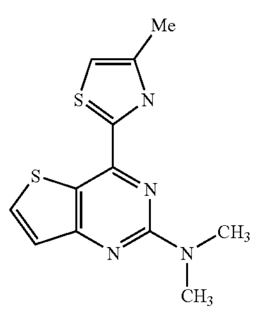 | N,N-dimethyl-4-(4-methyl-2-thiazolyl)thieno[3,2-d]pyrimidine-2-amine |
| 77 (H) | 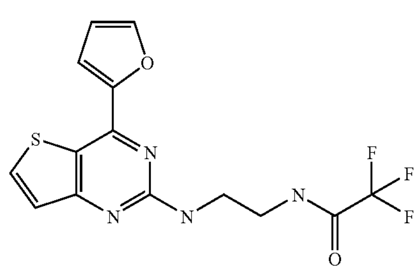 | N-(2-(4-(2-furyl)thieno[3,2-d]pyrimidine-2-ylamino)ethyl)trifluoroacetamide |

TABLE 1-continued

| Example | Structure | Compound Name |
|---|---|---|
| 78 (E) | 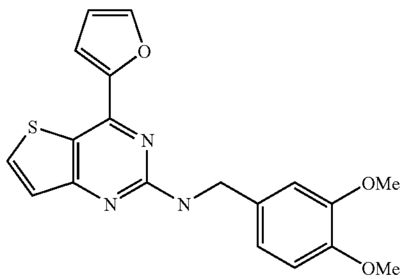 | N-(3,4-dimethoxybenzyl)-4-(2-furyl)thieno[3,2-d]pyrimidine-2-amine |
| 79 (F) | 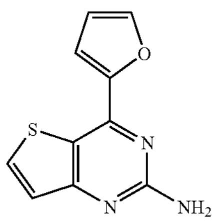 | 4-(2-furyl)thieno[3,2-d]pyrimidine-2-amine |
| 80 (C) | 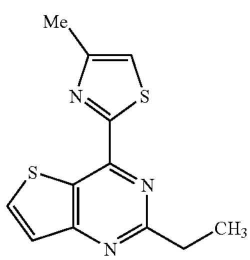 | 2-ethyl-4-(4-methyl-2-thiazolyl)thieno[3,2-d]pyrimidine |
| 81 (K) | 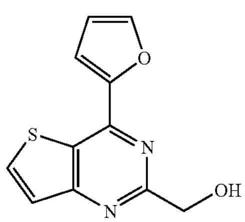 | 4-(2-furyl)thienol[3,2-d]pyrimidine-2-methanol |
| 82 (C) | 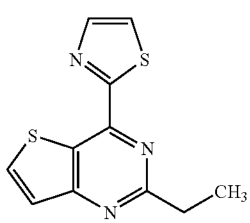 | 2-ethyl-4-(2-thiazolyl)thieno[3,2-d]pyrimidine |
| 83 (H) | 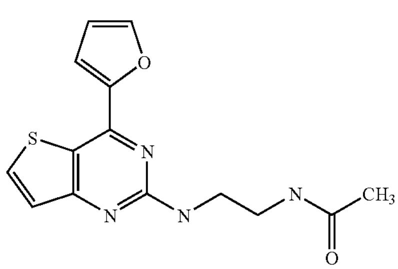 | N-(2-(4-(2-furyl)thieno[3,2-d]pyrimidine-2-ylamino)ethyl)acetamide |

TABLE 1-continued

| Example | Structure | Compound Name |
|---|---|---|
| 84 (H) | 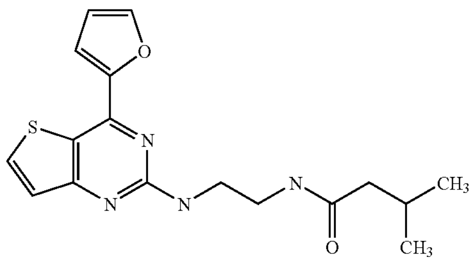 | N-(2-(4-(2-furyl)thieno[3,2-d]pyrimidine-2-ylamino)ethyl)-3-methylbutanamide |
| 85 (H) | 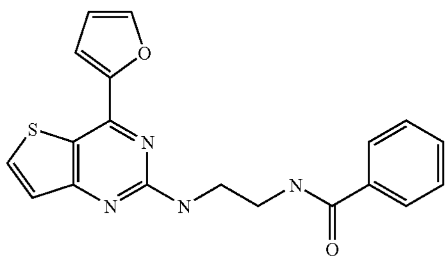 | N-(2-(4-(2-furyl)thieno[3,2-d]pyrimidine-2-ylamino)ethyl)benzamide |
| 86 (H) | 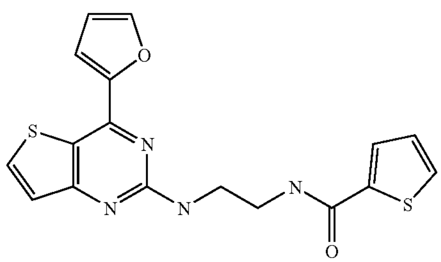 | N-(2-(4-(2-furyl)thieno[3,2-d]pyrimidine-2-ylamino)ethyl)thiophene-2-carboxamide |
| 87 (H) | 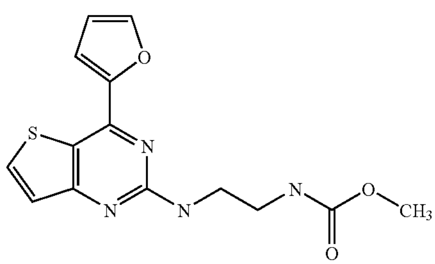 | methyl (2-(4-(2-furyl)thieno[3,2-d]pyrimidine-2-ylamino)ethyl)carbamate |
| 88 (H) | 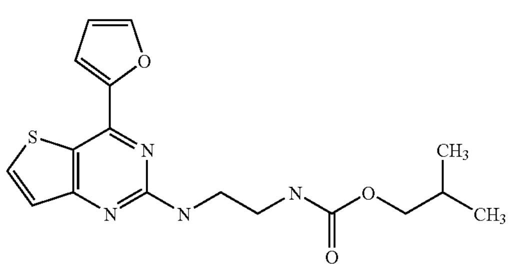 | isobutyl (2-(4-(2-furyl)thieno[3,2-d]pyrimidine-2-ylamino)ethyl)carbamate |
| 89 (H) | 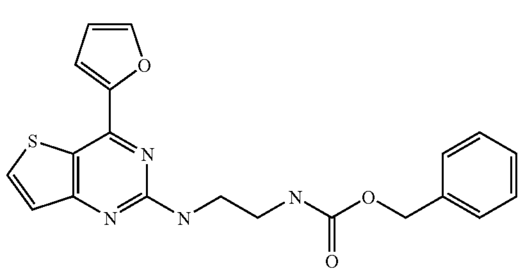 | benzyl (2-(4-(2-furyl)thieno[3,2-d]pyrimidine-2-ylamino)ethyl)carbamate |

TABLE 1-continued

| Example | Structure | Compound Name |
| --- | --- | --- |
| 90 (H) | 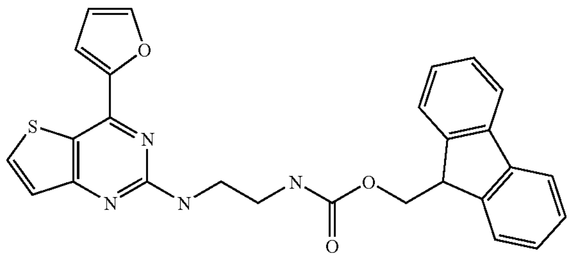 | 9-fluorenylmethyl (2-(4-(2-furyl)thieno[3,2-d]pyrimidine-2-ylamino)ethyl)carbamate |
| 91 (I) | 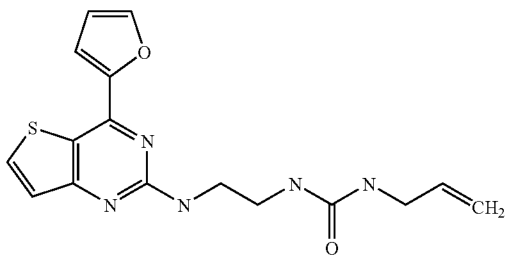 | N-allyl-N'-(2-(4-(2-furyl)thieno[3,2-d]pyrimidine-2-ylamino)ethyl)urea |
| 92 (I) | 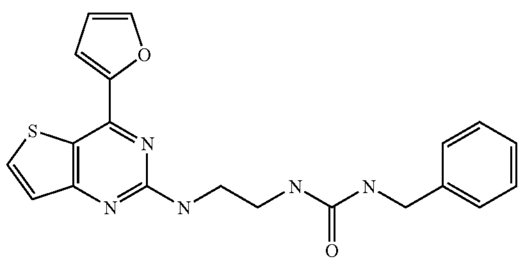 | N-benzyl-N'-(2-(4-(2-furyl)thieno[3,2-d]pyrimidine-2-ylamino)ethyl)urea |
| 93 (I) | 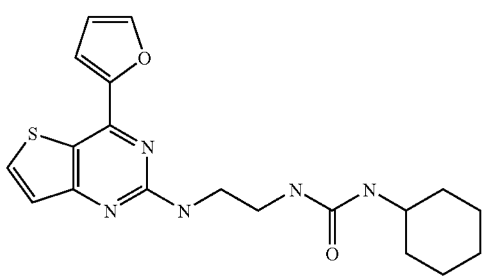 | N-cyclohexyl-N'-(2-(4-(2-furyl)thieno[3,2-d]pyrimidine-2-ylamino)ethyl)urea |
| 94 (I) | 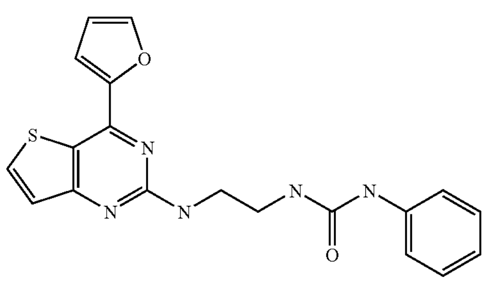 | N-(2-(4-(2-furyl)thieno[3,2-d]pyrimidine-2-ylamino)ethyl)-N'-phenylurea |

TABLE 1-continued

| Example | Structure | Compound Name |
| --- | --- | --- |
| 95 (I) | 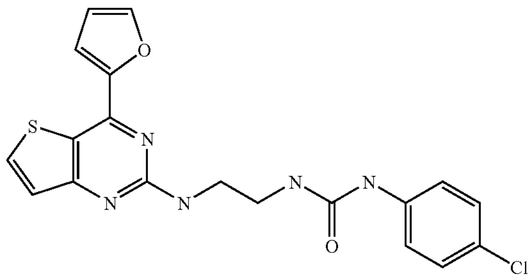 | N-(4-chlorophenyl)-N'-(2-(4-(2-furyl)thieno[3,2-d]pyrimidine-2-ylamino)ethyl)urea |
| 96 (I) | 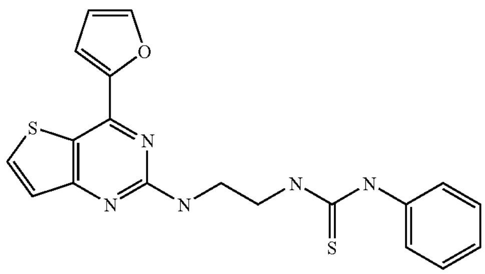 | N-(2-(4-(2-furyl)thieno[3,2-d]pyrimidine-2-ylamino)ethyl)-N'-phenylthiourea |
| 97 (I) | 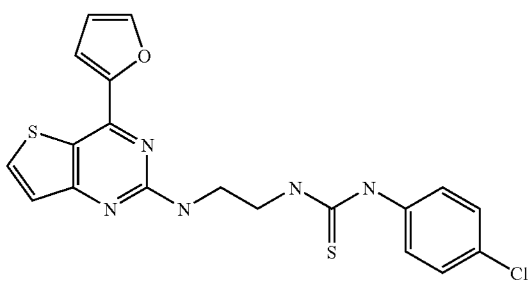 | N-(4-chlorophenyl)-N'-(2-(4-(2-furyl)thieno[3,2-d]pyrimidine-2-ylamino)ethyl)thiourea |
| 98 (H) | 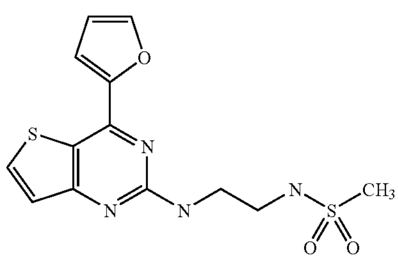 | N-(2-(4-(2-furyl)thieno[3,2-d]pyrimidine-2-ylamino)ethyl)methanesulphonamide |
| 99 (H) | 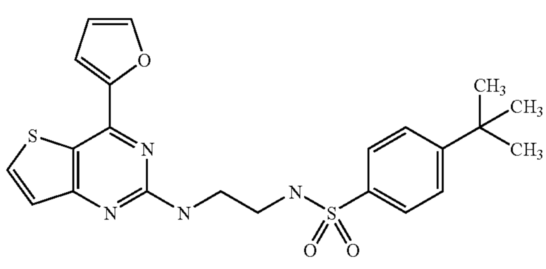 | N-(2-(4-(2-furyl)thieno[3,2-d]pyrimidine-2-ylamino)ethyl)4-tert-butylphenylsulphonamide |

TABLE 1-continued

| Example | Structure | Compound Name |
|---|---|---|
| 100 (A) | 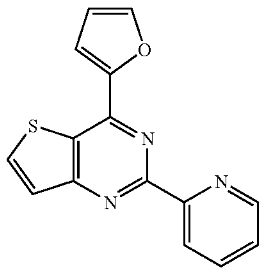 | 4-(2-furyl)-2-(2-pyridyl)thieno[3,2-d]pyrimidine |
| 101 (G) | 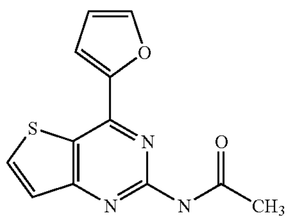 | N-(4-(2-furyl)thieno[3,2-d]pyrimidin-2-yl)acetamide |
| 102 (C) | 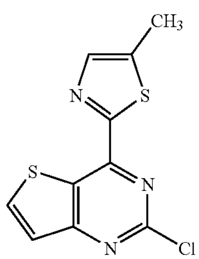 | 2-chloro-4-(5-methyl-2-thiazolyl)thieno[3,2-d]pyrimidine |
| 103 (C) | 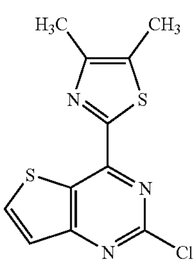 | 2-chloro-4-(4,5-dimethyl-2-thiazolyl)thieno[3,2-d]pyrimidine |
| 104 (E) | 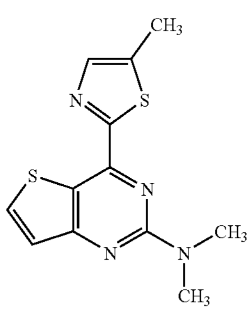 | N,N-dimethyl-4-(5-methyl-2-thiazolyl)thieno[3,2-d]pyrimidine-2-amine |

TABLE 1-continued

| Example | Structure | Compound Name |
| --- | --- | --- |
| 105 (E) | 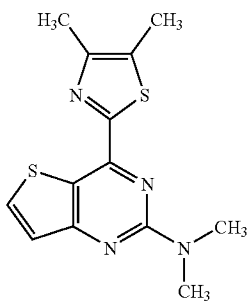 | N,N-dimethyl-4-(4,5-dimethyl-2-thiazolyl)thieno[3,2-d]pyrimidine-2-amine |
| 106 (C) | 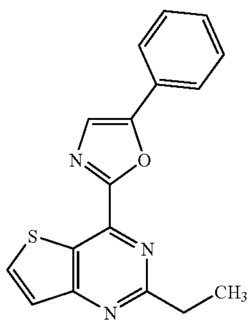 | 2-ethyl-4-(5-phenyl-2-oxazolyl)thieno[3,2-d]pyrimidine |
| 107 (D) | 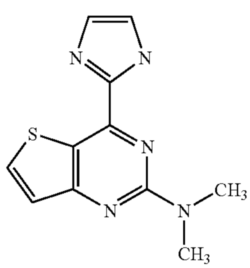 | N,N-dimethyl-4-(1H-imidazol-2-yl)thieno[3,2-d]pyrimidine-2-amine |
| 108 (E) | 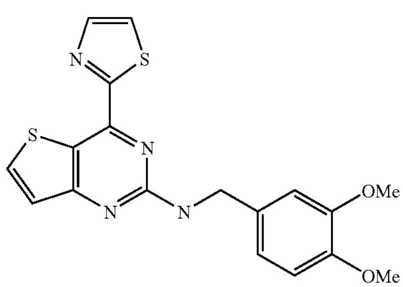 | N-(3,4-dimethoxybenzyl)-4-(2-thiazolyl)thieno[3,2-d]pyrimidine-2-amine |
| 109 (C) | 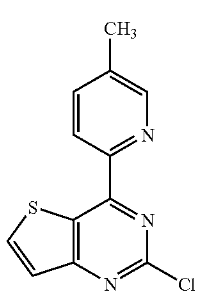 | 2-chloro-4-(5-methyl-2-pyridyl)thieno[3,2-d]pyrimidine |

TABLE 1-continued

| Example | Structure | Compound Name |
|---|---|---|
| 110 (F) | 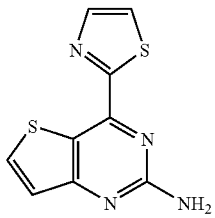 | 4-(2-thiazolyl)thieno[3,2-d]pyrimidine-2-amine |
| 111 (E) | 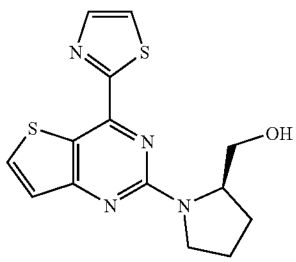 | (2R)-2-(2-hydroxymethylpyrrolidin-1-yl)-4-(2-thiazolyl)thieno[3,2-d]pyrimidine |
| 112 (E) | 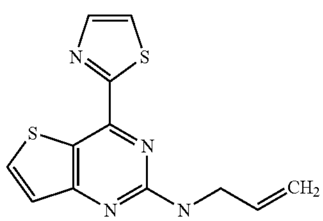 | N-allyl-4-(2-thiazolyl)thieno[3,2-d]pyrimidine-2-amine |
| 113 (C) | 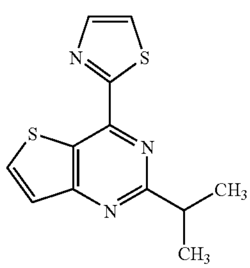 | 2-isopropyl-4-(2-thiazolyl)thieno[3,2-d]pyrimidine |
| 114 (C) | 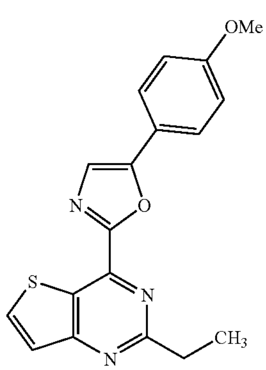 | 2-ethyl-4-(5-(4-methoxyphenyl)-2-oxazolyl)thieno[3,2-d]pyrimidine |

TABLE 1-continued

| Example | Structure | Compound Name |
| --- | --- | --- |
| 115 (E) | 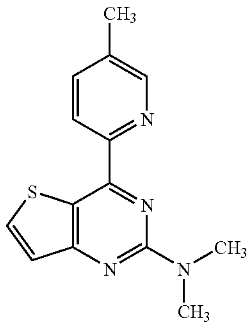 | N,N-dimethyl-4-(5-methyl-2-pyridyl)thieno[3,2-d]pyrimidine-2-amine |
| 116 (G) | 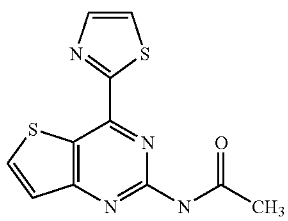 | N-(4-(2-thiazolyl)thieno[3,2-d]pyrimidin-2-yl)acetamide |
| 117 (A) | 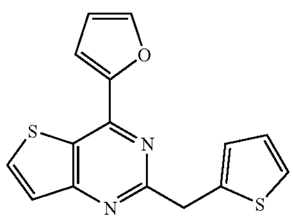 | 4-(2-furyl)-2-(2-thienylmethyl)thieno[3,2-d]pyrimidine |
| 118 (A) | 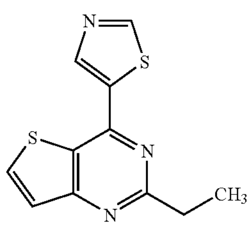 | 2-ethyl-4-(5-thiazolyl)thieno[3,2-d]pyrimidine |
| 119 (A) | 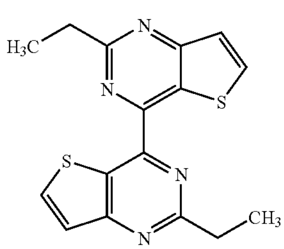 | 2-ethyl-4-(2-ethylthieno[3,2-d]pyrimidin-4-yl)thieno[3,2-d]pyrimidine |
| 120 (D) | 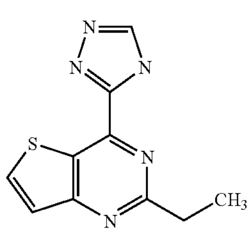 | 2-ethyl-4-(1H-triazol-3-yl)thieno[3,2-d]pyrimidine |

TABLE 1-continued

| Example | Structure | Compound Name |
|---|---|---|
| 121 (D) | 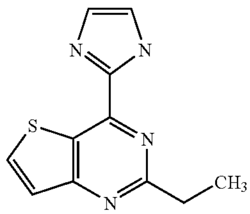 | 2-ethyl-4-(1H-imidazol-2-yl)thieno[3,2-d]pyrimidine |
| 122 (C) | 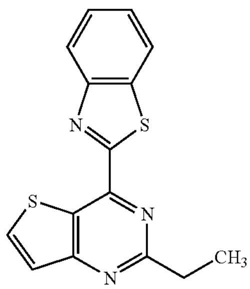 | 4-(2-benzothiazolyl)-2-ethylthieno[3,2-d]pyrimidine |
| 123 (E) | 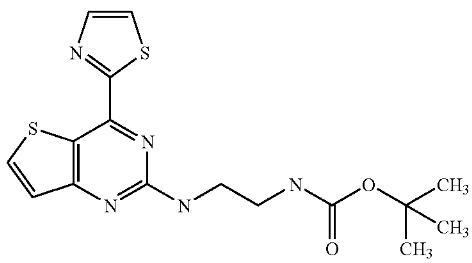 | tert-butyl (2-(4-(2-thiazolyl)thieno[3,2-d]pyrimidine-2-ylamino)ethyl)carbamate |
| 124 (F) | 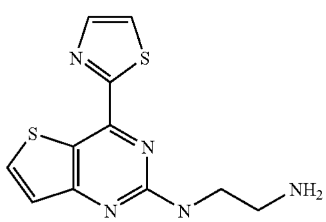 | N-(2-aminoethyl)-4-(2-thiazolyl)thieno[3,2-d]pyrimidine-2-amine |
| 125 (H) | 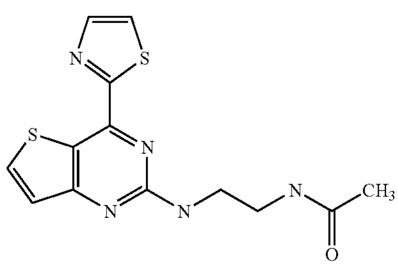 | N-(2-(4-(2-thiazolyl)thieno[3,2-d]pyrimidine-2-ylamino)ethyl)acetamide |
| 126 (I) | 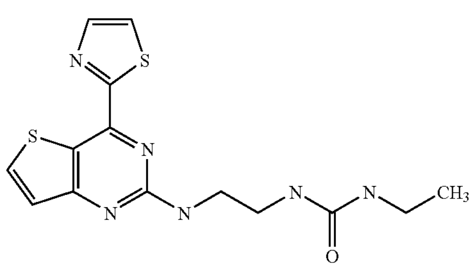 | N-ethyl-N'-(2-(4-(2-thiazolyl)thieno[3,2-d]pyrimidine-2-ylamino)ethyl)urea |

TABLE 1-continued

| Example | Structure | Compound Name |
|---|---|---|
| 127 (I) | 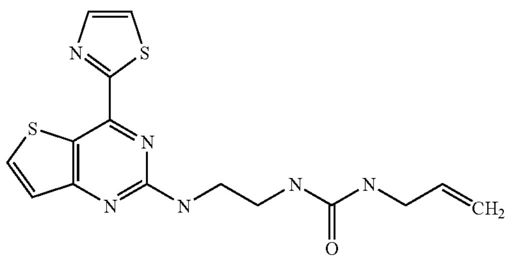 | N-allyl-N'-(2-(4-(2-thiazolyl)thieno[3,2-d]pyrimidine-2-ylamino)ethyl)urea |
| 128 (I) | 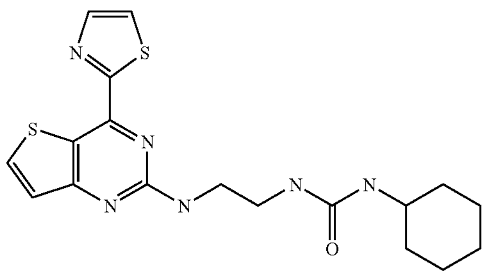 | N-cyclohexyl-N'-(2-(4-(2-thiazolyl)thieno[3,2-d]pyrimidine-2-ylamino)ethyl)urea |
| 129 (H) | 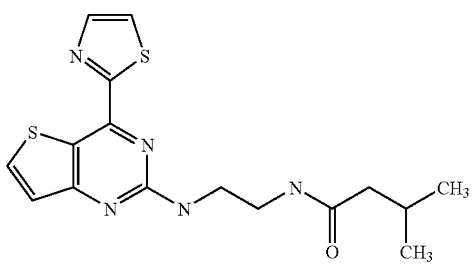 | N-(2-(4-(2-thiazolyl)thieno[3,2-d]pyrimidine-2-ylamino)ethyl)-3-methylbutanamide |
| 130 (H) | 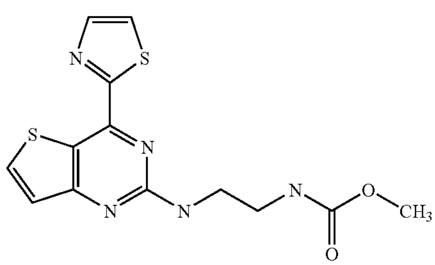 | methyl (2-(4-(2-thiazolyl)thieno[3,2-d]pyrimidine-2-ylamino)ethyl)carbamate |
| 131 (H) | 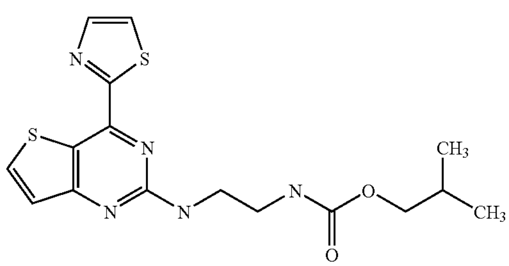 | isobutyl (2-(4-(2-thiazolyl)thieno[3,2-d]pyrimidine-2-ylamino)ethyl)carbamate |
| 132 (I) | 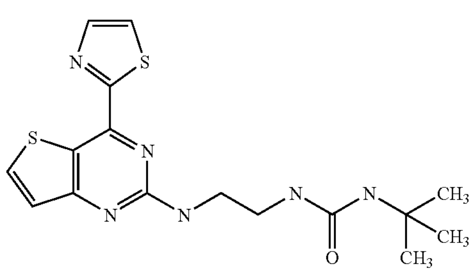 | N-tert-butyl-N'-(2-(4-(2-thiazolyl)thieno[3,2-d]pyrimidine-2-ylamino)ethyl)urea |

TABLE 1-continued

| Example | Structure | Compound Name |
| --- | --- | --- |
| 133 (I) | 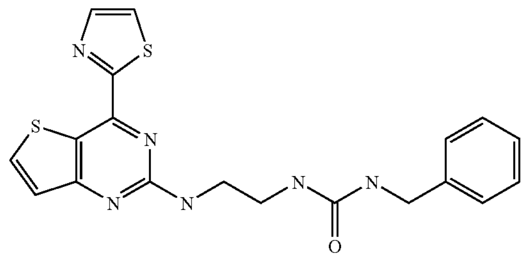 | N-benzyl-N'-(2-(4-(2-thiazolyl)thieno[3,2-d]pyrimidine-2-ylamino)ethyl)urea |
| 134 (I) | 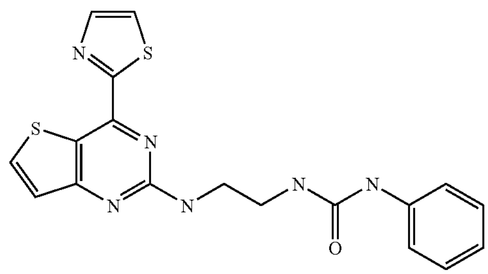 | N-phenyl-N'-(2-(4-(2-thiazolyl)thieno[3,2-d]pyrimidine-2-ylamino)ethyl)urea |
| 135 (I) | 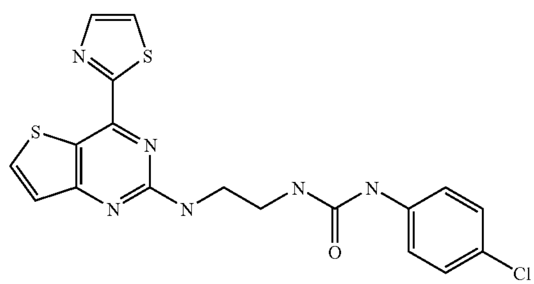 | N-(4-chlorophenyl)-N'-(2-(4-(2-thiazolyl)thieno[3,2-d]pyrimidine-2-ylamino)ethyl)urea |
| 136 (I) | 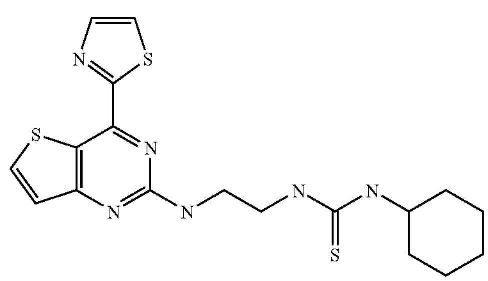 | N-cyclohexyl-N'-(2-(4-(2-thiazolyl)thieno[3,2-d]pyrimidine-2-ylamino)ethyl)thiourea |
| 137 (I) | 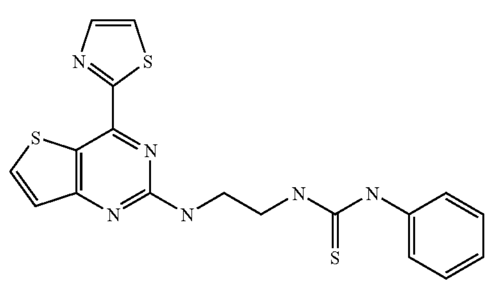 | N-phenyl-N'-(2-(4-(2-thiazolyl)thieno[3,2-d]pyrimidine-2-ylamino)ethyl)thiourea |

TABLE 1-continued

| Example | Structure | Compound Name |
|---|---|---|
| 138 (I) | 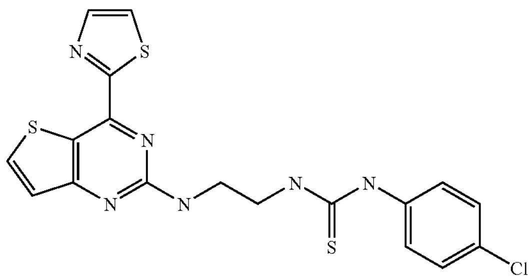 | N-(4-chlorophenyl)-N'-(2-(4-(2-thiazolyl)thieno[3,2-d]pyrimidine-2-ylamino)ethyl)thiourea |
| 139 (C) | 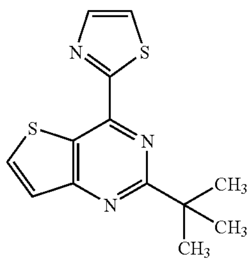 | 2-tert-butyl-4-(2-thiazolyl)thieno[3,2-d]pyrimidine |
| 140 (C) | 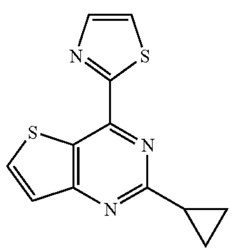 | 2-cyclopropyl-4-(2-thiazolyl)thieno[3,2-d]pyrimidine |
| 141 (C) | 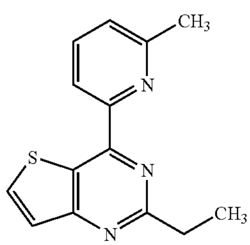 | 2-ethyl-4-(6-methyl-2-pyridyl)thieno[3,2-d]pyrimidine |
| 142 (H) | 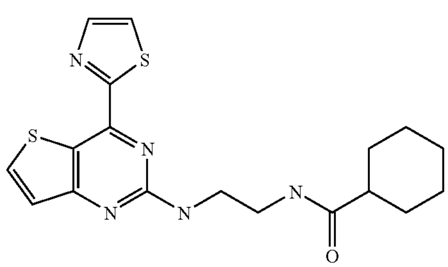 | N-(2-(4-(2-thiazolyl)thieno[3,2-d]pyrimidine-2-ylamino)ethyl)cyclohexylcarboxamide |
| 143 (H) | 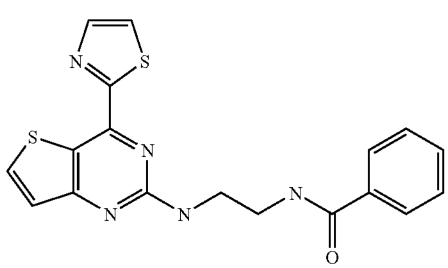 | N-(2-(4-(2-thiazolyl)thieno[3,2-d]pyrimidine-2-ylamino)ethyl)benzamide |

TABLE 1-continued

| Example | Structure | Compound Name |
| --- | --- | --- |
| 144 (H) | 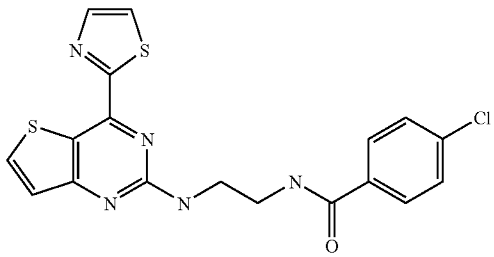 | 4-chloro-N-(2-(4-(2-thiazolyl)thieno[3,2-d]pyrimidine-2-ylamino)ethyl)benzamide |
| 145 (H) | 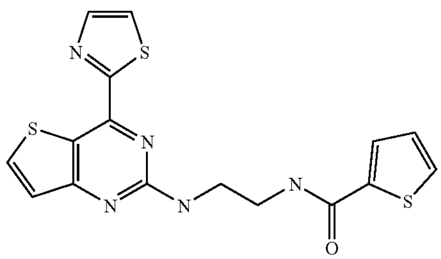 | N-(2-(4-(2-thiazolyl)thieno[3,2-d]pyrimidine-2-ylamino)ethyl)thiophene-2-carboxamide |
| 146 (H) | 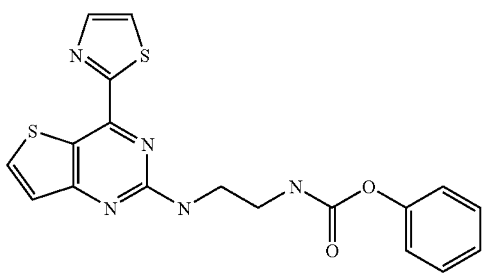 | phenyl (2-(4-(2-thiazolyl)thieno[3,2-d]pyrimidine-2-ylamino)ethyl)carbamate |
| 147 (H) | 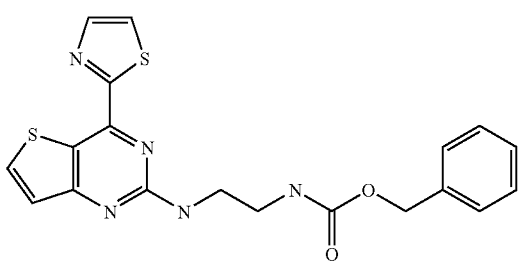 | benzyl (2-(4-(2-thiazolyl)thieno[3,2-d]pyrimidine-2-ylamino)ethyl)carbamate |
| 148 (H) | 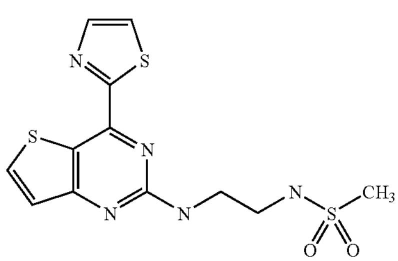 | N-(2-(4-(2-thiazolyl)thieno[3,2-d]pyrimidine-2-ylamino)ethyl)methanesulphonamide |
| 149 (H) | 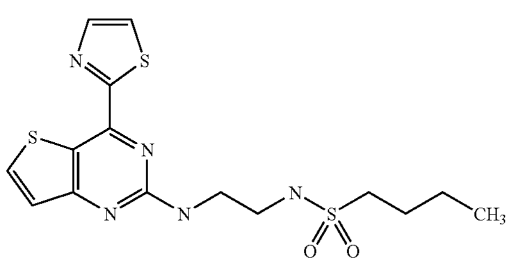 | N-(2-(4-(2-thiazolyl)thieno[3,2-d]pyrimidine-2-ylamino)ethyl)butanesulphonamide |

TABLE 1-continued

| Example | Structure | Compound Name |
|---|---|---|
| 150 (E) | 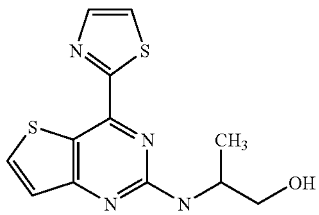 | (1RS)-N-(2-hydroxy-1-methylethyl)-4-(2-thiazolyl)thieno[3,2-d]pyrimidine-2-amine |
| 151 (E) | 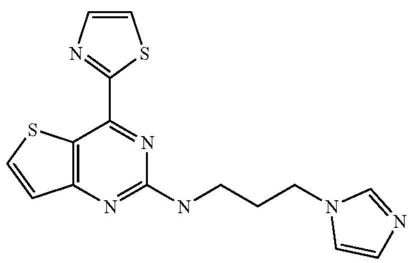 | N-(3-(1H-imidazol-1-yl)propyl)-4-(2-thiazolyl)thieno[3,2-d]pyrimidine-2-amine |
| 152 (E) | 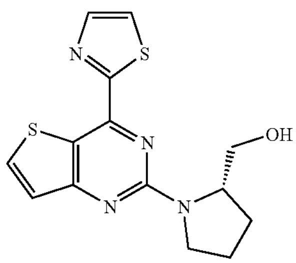 | (2S)-2-(2-hydroxymethylpyrrolidin-1-yl)-4-(2-thiazolyl)thieno[3,2-d]pyrimidine |
| 153 (C) | 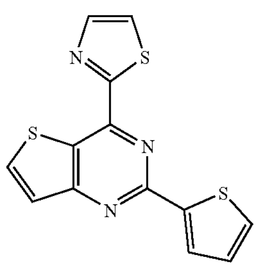 | 4-(2-thiazolyl)-2-(2-thienyl)thieno[3,2-d]pyrimidine |
| 154 (C) | 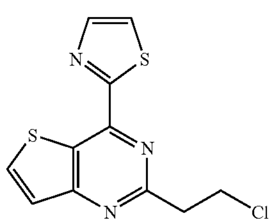 | 2-(2-chloroethyl)-4-(2-thiazolyl)thieno[3,2-d]pyrimidine |
| 155 (O) | 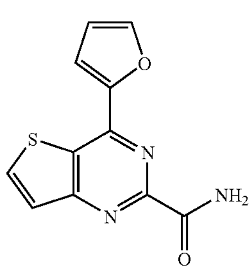 | 4-(2-furyl)thieno[3,2-d]pyrimidine-2-carboxamide |

TABLE 1-continued

| Example | Structure | Compound Name |
|---|---|---|
| 156 (B) | 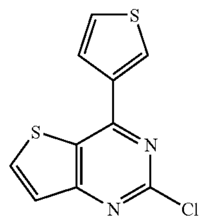 | 2-chloro-4-(3-thienyl)thieno[3,2-d]pyrimidine |
| 157 (E) | 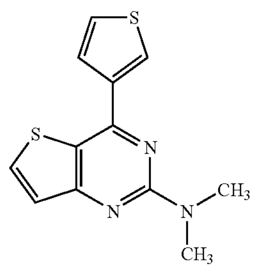 | N,N-dimethyl-4-(3-thienyl)thieno[3,2-d]pyrimidine-2-amine |
| 158 (B) | 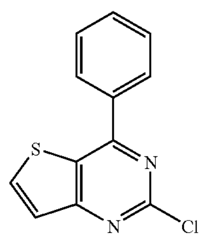 | 2-chloro-4-phenylthieno[3,2-d]pyrimidine |
| 159 (E) | 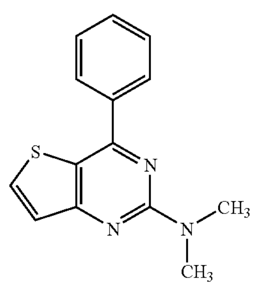 | N,N-dimethyl-4-phenylthieno[3,2-d]pyrimidine-2-amine |
| 160 (B) | 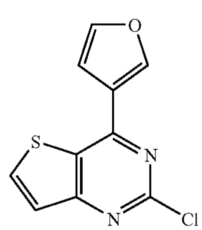 | 2-chloro-4-(3-furyl)thieno[3,2-d]pyrimidine |
| 161 (E) | 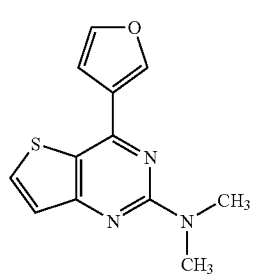 | N,N-dimethyl-4-(3-furyl)thieno[3,2-d]pyrimidine-2-amine |

TABLE 1-continued

| Example | Structure | Compound Name |
|---|---|---|
| 162 (A) | 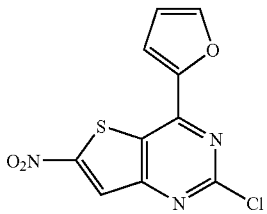 | 2-chloro-4-(2-furyl)-6-nitrothieno[3,2-d]pyrimidine |
| 163 (B) | 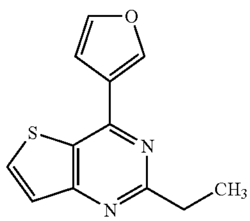 | 2-ethyl-4-(3-furyl)thieno[3,2-d]pyrimidine |
| 164 (B) | 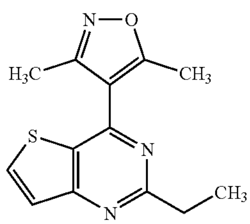 | 4-(3,5-dimethyl-4-isoxazolyl)-2-ethylthieno[3,2-d]pyrimidine |
| 165 (B) | 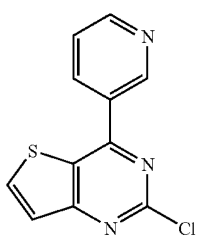 | 2-chloro-4-(3-pyridyl)thieno[3,2-d]pyrimidine |
| 166 (E) | 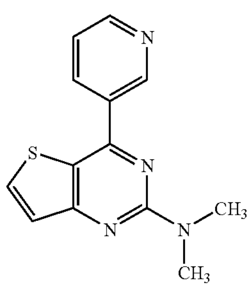 | N,N-dimethyl-4-(3-pyridyl)thieno[3,2-d]pyrimidine-2-amine |
| 167 (C) | 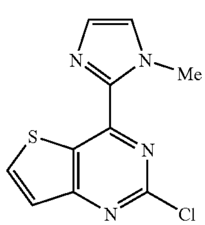 | 2-chloro-4-(1-methyl-1H-imidazol-2-yl)thieno[3,2-d]pyrimidine |

TABLE 1-continued

| Example | Structure | Compound Name |
|---|---|---|
| 168 (E) | 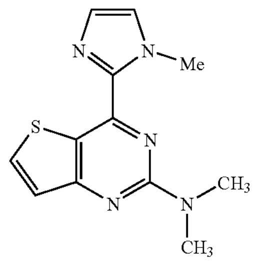 | N,N-dimethyl-4-(1-methyl-1H-imidazol-2-yl)thieno[3,2-d]pyrimidine-2-amine |
| 169 (E) | 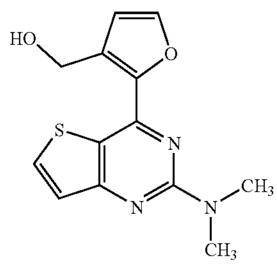 | N,N-dimethyl-4-(3-hydroxymethyl-2-furyl)thieno[3,2-d]pyrimidine-2-amine |
| 170 (E) | 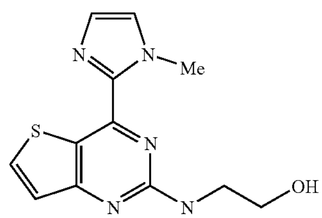 | N-(2-hydroxyethyl)-4-(1-methyl-1H-imidazol-2-yl)thieno[3,2-d]pyrimidine-2-amine |
| 171 (E) | 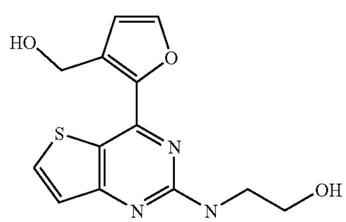 | N-(2-hydroxyethyl)-4-(3-hydroxymethyl-2-furyl)thieno[3,2-d]pyrimidine-2-amine |
| 172 (C) | 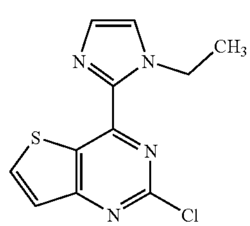 | 2-chloro-4-(1-ethyl-1H-imidazol-2-yl)thieno[3,2-d]pyrimidine |
| 173 (E) | 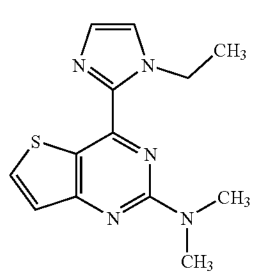 | N,N-dimethyl-4-(1-ethyl-1H-imidazol-2-yl)thieno[3,2-d]pyrimidine-2-amine |

TABLE 1-continued

| Example | Structure | Compound Name |
|---|---|---|
| 174 (E) | 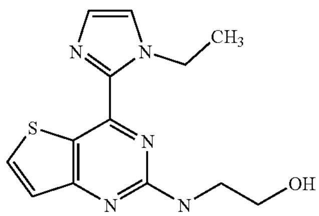 | 4-(1-ethyl-1H-imidazol-2-yl)-N-(2-hydroxyethyl)thieno[3,2-d]pyrimidine-2-amine |
| 175 (C) | 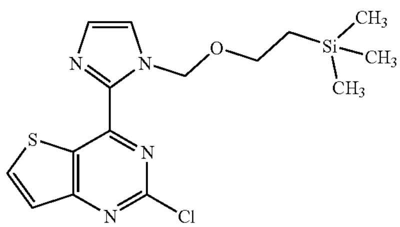 | 2-chloro-4-(1-(2-trimethylsilylethoxymethyl)-1H-imidazol-2-yl)thieno[3,2-d]pyrimidine |
| 176 (E) | 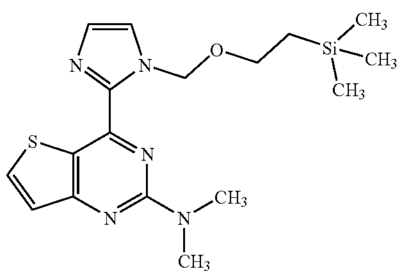 | N,N-dimethyl-4-(1-(2-trimethylsilylethoxymethyl)-1H-imidazol-2-yl)thieno[3,2-d]pyrimidine-2-amine |
| 177 (C) | 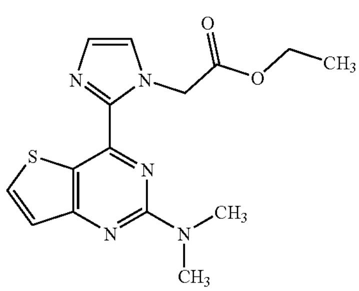 | N,N-dimethyl-4-((1-ethoxycarbonylmethyl)-1H-imidazol-2-yl)thieno[3,2-d]pyrimidine-2-amine |
| 178 (K) | 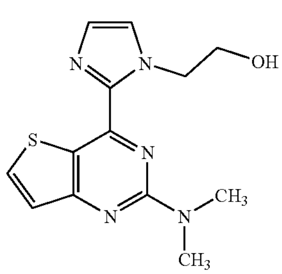 | N,N-dimethyl-4-(1-(2-hydroxyethyl)-1H-imidazol-2-yl)thieno[3,2-d]pyrimidine-2-amine |
| 179 (C) | 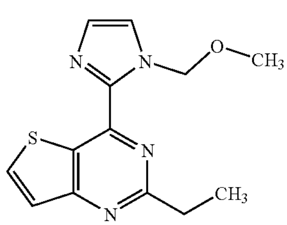 | 2-ethyl-4-(1-methoxymethyl-1H-imidazol-2-yl)thieno[3,2-d]pyrimidine |

TABLE 1-continued

| Example | Structure | Compound Name |
| --- | --- | --- |
| 180 (C) | 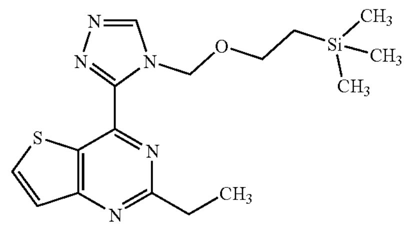 | 2-ethyl-4-(4-(2-trimethylsilylethoxymethyl)-4H-1,2,4-triazol-3-yl)thieno[3,2-d]pyrimidine |
| 181 (C) | 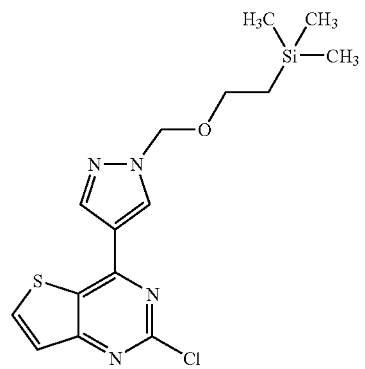 | 2-chloro-4-(1-(2-trimethylsilylethoxymethyl)-1H-pyrazol-4-yl)thieno[3,2-d]pyrimidine |
| 182 (C) | 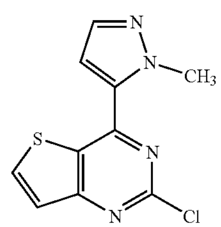 | 2-chloro-4-(1-methyl-1H-pyrazol-5-yl)thieno[3,2-d]pyrimidine |
| 183 (E) | 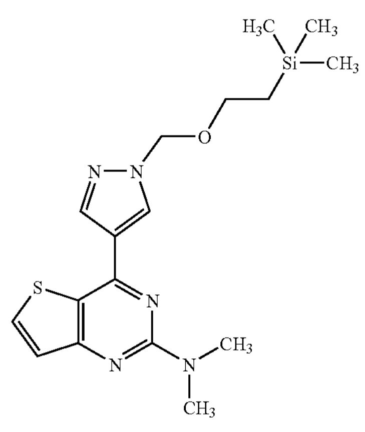 | N,N-dimethyl-4-(1-(2-trimethylsilylethoxymethyl)-1H-pyrazol-4-yl)thieno[3,2-d]pyrimidine-2-amine |
| 184 (E) | 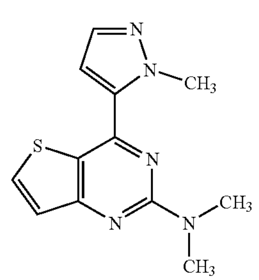 | N,N-dimethyl-4-(1-methyl-1H-pyrazol-5-yl)thieno[3,2-d]pyrimidine-2-amine |

TABLE 1-continued

| Example | Structure | Compound Name |
|---|---|---|
| 185 (D) | 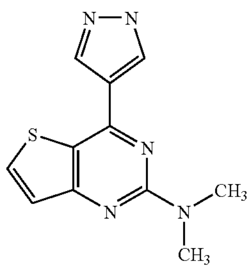 | N,N-dimethyl-4-(1H-pyrazol-4-yl)thieno[3,2-d]pyrimidine-2-amine |
| 186 (C) | 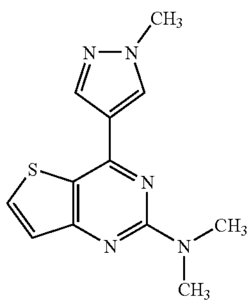 | N,N-dimethyl-4-(1-methyl-1H-pyrazol-4-yl)thieno[3,2-d]pyrimidine-2-amine |
| 187 (C) | 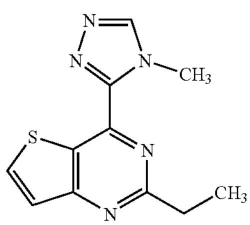 | 2-ethyl-4-(4-methyl-4H-1,2,4-triazol-3-yl)thieno[3,2-d]pyrimidine |
| 188 (A) | 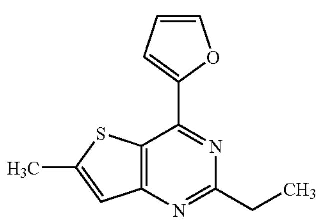 | 2-ethyl-4-(2-furyl)-6-methylthieno[3,2-d]pyrimidine |

The general synthetic methods used for the preparation of these examples are set out below as Methods A to T.

Method A

2-Chloro-4-(2-furyl)thieno[3,2-d]pyrimidine (Example 3)

A solution of 2,4-dichlorothieno[3,2-d]pyrimidine (205 mg, 1 mmol) in DMF (4 mL) was treated with PdCl$_2$(PPh$_3$)$_2$ (35 mg, 0.05 mmol) and 2-(tributylstannyl)-furan (315 µL, 1 mmol), stirred at room temperature for 16 h, the reaction mixture purified directly by chromatography (SiO$_2$:EtOAc: Heptane, 1:9) and the resulting cream solid recrystallised (EtOAc/Heptane) to give the title compound (122 mg, 52%) as a cream solid.

Method B

2-Chloro-4-(5-chloro-2-thienyl)thieno[3,2-d]pyrimidine

A solution of Pd(OAc)$_2$ (12 mg, 5 mol %) and PPh$_3$ (52 mg, 20 mol %) in THF (2 mL) was stirred for 5 min, treated dropwise with a solution of 2,4-dichlorothieno[3,2-d]pyrimidine (205 mg, 1 mmol) in THF (1 mL), stirred for 5 min, treated with 5-chlorothiophene-2-boronic acid (244 mg, 1.5 mmol) then saturated aqueous NaHCO$_3$ (1 mL) refluxed for 4 h, cooled, diluted with H$_2$O and filtered to give the title compound (268 mg, 94%) as a grey solid; NMR δ$_H$ (400 MHz, CDCl$_3$) 7.10 (1H, d, J 4.0 Hz), 7.55 (1H, d, J 5.5 Hz), 7.85 (1H, d, J 4.5 Hz) and 8.08 (1H, d, J 5.5 Hz)

Method C

2-Chloro-4-(2-thiazolyl)thieno[3,2-d]pyrimidine (Example 64)

A stirred solution of thiazole (0.14 mL, 2 mmol) in dry THF (10 mL) at −78° C., under argon was treated with n-BuLi (1.6-M in hexanes, 1.3 mL, 2 mmol), stirred for 30 min, treated with a solution of ZnCl$_2$ (1.0-M in Et$_2$O, 2.0 mL, 2 mmol) and allowed to warm gradually to room temperature. The mixture was treated with a solution of 2,4-dichlorothieno[3,2-d]pyrimidine (205 mg, 1 mmol) in THF (5 mL) then Pd(PPh$_3$)$_4$ (100 mg, 10 mol %) refluxed for 17 h, cooled, diluted with saturated NH$_4$Cl solution and extracted with EtOAc. The organic extracts were dried (MgSO$_4$), concentrated in vacuo and purified by chromatography [SiO$_2$; isohexane:CH$_2$Cl$_2$ (2:1)] to give the title compound (75 mg, 26%) as a white solid.

Method D

2-Ethyl-4-(1H-imidazol-2-yl)thieno[3,2-d]pyrimidine (Example 121)

A stirred solution of 1-(2-trimethylsilyl)ethoxymethyl-1H-imidazole (295 mg, 1.5 mmol) in dry THF (10 mL) at −78° C., under argon was treated with n-BuLi (1.6-M in hexanes, 0.93 mL, 1.5 mmol), stirred for 30 min, treated with a solution of ZnCl$_2$ (1.0-M in Et$_2$O, 1.5 mL, 1.5 mmol) and the mixture allowed to warm gradually to room temperature. The mixture was treated with 4-chloro-2-ethylthieno[3,2-d]pyrmidine (148 mg, 0.75 mmol) and Pd(PPh$_3$)$_4$ (100 mg), refluxed for 3 h, cooled, diluted with saturated NH$_4$Cl solution, extracted with EtOAc, dried (MgSO$_4$), concentrated in vacuo and purified by chromatography [SiO$_2$; heptane: EtOAc (7:1) then (4:1)] to give the intermediate coupled product as a viscous oil (140 mg). A portion of this material (130 mg, 0.36 mmol) was dissolved in THF (5 mL), treated with a solution of tetra-n-butylammonium fluoride (1-M in THF, 0.72 mL, 0.72 mmol), refluxed for 4 hr, cooled, extracted with EtOAc, dried (MgSO$_4$) concentrated in vacuo and purified by chromatography [SiO$_2$; heptane:EtOAc (4:1) then (2:1)] to give the title compound (62 mg, 39%) as a white solid.

Method E

7-Bromo-4-(2-furyl)-N-(2-hydroxyethyl)thieno[3,2-d]pyrimidine-2-amine (Example 15)

A solution of 7-bromo-2-chloro-4-(2-furyl)thieno[3,2-d]pyrimidine (110 mg, 0.35 mmol) in 1-methyl-2-pyrrolidinone (1 mL) was treated with ethanolamine (32 μL, 0.52 mmol), heated at 90° C. for 16 h, cooled, poured into water, extracted with EtOAc, dried (MgSO$_4$), concentrated in vacuo and purified by chromatography (SiO$_2$: EtOAc:Heptane, 1:1) to give the title compound (45 mg, 38%) as a yellow solid.

Method F 4-(2-Furyl)thieno[3,2-d]pyrimidine-2-amine (Example 79)

A solution of N-(3,4-dimethoxybenzyl)-4-(2-furyl)thieno[3,2-d]pyrimidine-2-amine (199 mg, 0.54 mmol) in TFA (1 mL) was heated at 60° C. for 1 h, cooled, poured into sat. NaHCO$_3$, extracted with EtOAc, dried (MgSO$_4$), concentrated in vacuo and purified by chromatography (SiO$_2$: EtOAc:Heptane, 1:1 and MeOH:DCM, 1:19) to give the title compound (108 mg, 92%) as a cream solid.

Method G

N-(4-(2-Furyl)thieno[3,2-d]pyrimidin-2-yl)acetamide (Example 101)

An ice-cold solution of 4-(2-furyl)thieno[3,2-d]pyrimidine-2-amine (130 mg, 0.6 mmol) in pyridine (1 mL) was treated with acetyl chloride (47 μL, 0.66 mmol), stirred at room temperature for 16 h, poured into water, extracted with EtOAc, dried (MgSO$_4$) and concentrated in vacuo and purified by chromatography (SiO$_2$:EtOAc:Heptane, 1:1) to give the title compound (125 mg, 80%) as a cream solid.

Method H

N-(2-(4-(2-Thiazolyl)thieno[3,2-d]pyrimidine-2-ylamino) ethyl)acetamide (Example 125)

A solution of N-(2-aminoethyl)-4-(2-thiazolyl))thieno[3,2-d]pyrimidine-2-amine (0.040 g, 0.14 mmol) in DMF (2 mL) was treated with triethylammonium methylpolystyrene carbonate (0.066 g, 0.22 mmol) followed by acetyl chloride (0.023 g, 0.29 mmol), shaken at room temperature for 7 h, treated with tris-(2-aminoethyl)amine polystyrene (0.19 g, 0.87 mmol), shaken at room temperature for 16 h, treated with polystyrene 4-benzyloxybenzaldehyde (0.19 g, 0.28 mmol), shaken for a further 3 h, filtered and concentrated in vacuo to give the title compound as a yellow solid.

Method I

N-Ethyl-N'-(2-(4-(2-thiazolyl)thieno[3,2-d]pyrimidine-2-ylamino)ethyl)urea (Example 126)

A solution of N-(2-aminoethyl)-4-(2-thiazolyl))thieno[3,2-d]pyrimidine-2-amine (0.040 g, 0.14 mmol) in anhydrous DMF (2 mL) was treated with ethyl isocyanate (0.015 g, 0.22 mmol), shaken at 35° C. for 1 h, treated with tris-(2-aminoethyl)amine polystyrene (0.19 g, 0.88 mmol), shaken at 35° C. for 4 h, filtered and concentrated in vacuo to give the title compound as a yellow solid.

Method J

7-Amino-N,N-dimethyl-4-(2-furyl)thieno[3,2-d]pyrimidine-2-amine (Example 51)

A solution of N,N-dimethyl-4-(2-furyl)-7-nitrothieno[3,2-d]pyrimidine (85 mg, 0.29 mmol) in MeOH (4 mL), under argon, was treated with a catalytic amount of Pd on carbon (10%), hydrogenated at room temperature for 1 h, filtered through celite, concentrated in vacuo and purified by chromatography (SiO$_2$:EtOAc:Heptane, 1:4) to give the title compound (62 mg, 82%) as a brown solid.

Method K 2-(4-(2-Furyl)thieno[3,2-d]pyrimidin-2-yl)ethanol (Example 54)

A solution of ethyl 4-(2-furyl)thieno[3,2-d]pyrimidine-2-acetate (0.10 g, 0.35 mmol) in dichloromethane (13 mL) at −75° C. was treated dropwise with di-iso-butylaluminium hydride (0.87 mL, 1.0-M), stirred for 17 h, warmed to ambient temperature and partitioned between Rochelle's salt and dichloromethane. The combined organic phase was dried (MgSO$_4$), concentrated in vacuo and purified by chromatography (SiO$_2$:EtOAc) to give the title compound (21 mg, 25%) as a white solid.

Method L 4-(2-Furyl)-2-vinylthieno[3,2-d]pyrimidine (Example 69)

A solution of 2-(4-(2-furyl)thieno[3,2-d]pyrimidin-2-yl) ethanol (0.15 g, 0.61 mmol) in THF (5 mL) at 0° C. was treated with diisopropylethylamine (0.095 g, 0.73 mmol) then methanesulfonyl chloride (0.72 g, 0.67 mmol), warmed to room temperature over 16 h, partitioned between ethyl acetate and water, the organic phase dried (MgSO$_4$) and concentrated in vacuo to give the intermediate mesylate (0.10 g, 50%) as a white solid. A sample of this compound (59 mg, 0.18 mmol) was dissolved in CH$_2$Cl$_2$, treated with DBU (0.042 g, 0.27 mmol), stirred at room temperature for 18 h, partitioned between ethyl acetate and water and the organic phase was dried (MgSO$_4$) and concentrated in vacuo to give the title compound (22 mg, 50%) as a white solid.

Method M 3-(4-(2-Furyl)thieno[3,2-d]pyrimidin-2-yl)propionic Acid (Example 49)

A solution of ethyl 3-(4-(2-furyl)thieno[3,2-d]pyrimidine-2-yl)propionate (0.07 g, 0.23 mmol) in THF (1.0 mL) and water (1.0 mL) was treated with lithium hydroxide (0.10 g, 2.32 mmol), stirred for 16 h, concentrated in vacuo, dissolved in water, acidified to pH 2 by the addition of HCl (0.1 mL, 6.0-M), cooled in ice and filtered to give the title compound (0.052 g, 81%) as a white solid.

Method N 4-(2-Furyl)-2-(3-oxo-3-(1-pyrrolidinyl)propyl)thieno[3,2-d]pyrimidine (Example 50)

A mixture of trimethylaluminium in toluene (1.3 mL, 2.0-M) and pyrrolidine (0.22 mL, 2.65 mmol) in toluene was heated at 80° C. for 0.5 h, treated with a solution of ethyl 3-(4-(2-furyl)thieno[3,2-d]pyrimidine-2-yl) (0.1 g, 0.33 mmol) in toluene (2.0 mL), stirred at 80° C. for 17 h, cooled to room temperature and partitioned between sat. aq. $NH_4Cl$ and ethyl acetate. The combined organic phase was dried ($MgSO_4$), concentrated in vacuo and purified by chromatography ($SiO_2$: EtOAc-methanol, 9:1) to give the title compound (27 mg, 25%).

Method O 4-(2-Furyl)thieno[3,2-d]pyrimidine-2-carboxamide (Example 155)

Ammonia gas was bubbled through a hot solution of ethyl 4-(2-furyl)thieno[3,2-d]pyrimidine-2-carboxylate (0.156 g, 0.57 mmol) in ethanol (20 mL) for 3 h then the mixture cooled and the resulting white solid filtered to give the title compound (94 mg, 67%) as a white solid.

Method P 4,7-Bis(2-furyl)-N,N-dimethylthieno[3,2-d]pyrimidine-2-amine (Example 31)

A mixture of $AsPh_3$ (73 mg, 0.24 mmol) in DMF (2 mL) was treated with Pd(OAc)$_4$ (13 mg, 0.06 mmol), stirred at room temperature for 10 min, treated with 7-bromo-N,N-dimethyl-4-(2-furyl)thieno[3,2-d]pyrimidine-2-amine (194 mg, 0.6 mmol) and 2-(tributylstannyl)-furan (340 μL, 1.1 mmol), heated to 100° C. for 16 h, cooled, poured into water, extracted with EtOAc, dried ($MgSO_4$), concentrated in vacuo and purified by chromatography ($SiO_2$:EtOAc:Heptane, 1:9) to give the title compound (27 mg, 15%) as a orange solid.

Method Q

2-Isopropylthieno[3,2-d]pyrimidine-4-ol

A mixture of 3-aminothiophene-2-carboxamide (2.0 g, 14.1 mmol) and triethylamine (1.71 g, 16.9 mmol) in toluene (20 mL) at room temperature was treated with 2-methylpropionic anhydride (2.45 g, 15.5 mmol), refluxed for 4 h, cooled, poured into saturated $NaHCO_3$ (100 mL) and extracted with ethyl acetate (4×50 mL). The combined organic phase was washed with brine(2×50 mL), dried ($Na_2SO_4$) and concentrated in vacuo to the intermediate N-acylated compound (2.90 g, 99%) as a pale yellow solid. A sample of this compound (2.85 g, 13.44 mmol) was dissolved in NaOH (34 mL, 1.0-M), refluxed for 1 h, cooled, acidified to pH 2 by addition of HCl (7.0 mL, 6.0-M), filtered and dried to give the title compound (2.30 g, 88%) as a white solid: IR $v_{max}$ (Nujol)/cm$^{-1}$ 2956, 2925, 1676, 1599, 1464, 780; NMR $\delta_H$ (400 MHz, DMSO) 1.20 (6H, d J 6.5 Hz), 2.90 (1H, heptet, J 6.5 Hz), 7.40 (1H, d J 5.0 Hz), 8.15 (1H, d, J 5.0 Hz) and 12.30 (1H, br).

Method R

2-Cyclopropylthieno[3,2-d]pyrimidine-4-ol

Dry HCl gas was bubbled through a solution of methyl 3-aminothiophene-2-carboxylate (1.64 g, 10.4 mmol) and cyclopropanecarbonitrile (27 mL) in dioxane (40 mL) for 1 h then the reaction mixture was diluted with cold water (2 volumes), basified with $NH_4OH$ (50 mL) and the resulting solid filtered and air dried to give the title compound (1.44 g, 72%) as a white solid: IR $v_{max}$ (Nujol)/cm$^{-1}$ 2925, 1664, 1597, 788; NMR $\delta_H$ (400 MHz, DMSO) 1.04 (4H, m), 2.00 (1H, m), 7.20 (1H, d J 5.0 Hz), 8.10 (1H, d, J 5.0 Hz) and 12.60 (1H,br).

Method S

4-Chloro-2-isopropylthieno[3,2-d]pyrimidine

A suspension of 2-isopropylthieno[3,2-d]pyrimidine-4-ol (1.66 g, 8.56 mmol) in $POCl_3$ (30 mL) was refluxed for 1 h, cooled, diluted with chloroform (100 mL) and poured into a mixture of ice and $NH_4OH$ (150 mL). The organic phase was separated, washed with saturated $NaHCO_3$ (20 mL), water and brine, dried ($MgSO_4$) and concentrated in vacuo to give the title compound (2.01 g, 99%) as a pale yellow solid: IR $v_{max}$ (Nujol)/cm$^{-1}$ 3065, 2960, 2926, 2855, 1561, 1513, 1457, 803; NMR $\delta_H$ (400 MHz, CDCl$_3$) 1.40 (6H, d J 6.5 Hz), 3.38 (1H, heptet, J 6.5 Hz), 7.60 (1H, d J 5.0 Hz), 8.05 (1H, d, J 5.0 Hz).

Method T

Ethyl 4-hydroxythieno[3,2-d]pyrimidine-2-carboxylate

A mixture of 3-aminothiophene-2-carboxamide (1.23 g, 8.65 mmol) and EtOH (25 mL) was treated with NaOEt (1.2 g, 17.3 mmol) and diethyloxalate (2.3 mL, 17.3 mmol), refluxed for 18 h, cooled, concentrated in vacuo, treated with water, acidified with HOAc and filtered to give the title compound (1.43 g, 74%) as a cream solid: IR $v_{max}$ Nujol/cm$^{-1}$ 3180, 3119, 3078, 3006, 2955, 2924, 2854, 1737, 1667, 1651, 1300 and 1176; NMR $\delta_H$ (400 MHz, DMSO) 1.37 (3H, t, J 7.0 Hz), 4.40 (2H, q, J 7.0 Hz), 7.58 (1H, d, J 5.0 Hz), 8.30 (1H, d, J 5.1 Hz), and 12.92 (1H, s).

TABLE 2

Analytical data
HPLC is carried out using the following conditions: Column.
Supelcosil ABZ$^+$ (170 × 4.6 mm),
particle size 5 μM, mobile phase MeOH: 10 mM aq
NH$_4$OAc (80:20), (70:30) or (60:40) (specified
in Table 2), flow rate 1.0 mL/min.,
detection wavelength λ = 230 nM
(unless otherwise stated), retention
times are provided in Table 2.

| Example | Yield(%) | Physical Data |
|---|---|---|
| 1 | 61 | Mp 135.6-135.8° C.; IR $v_{max}$(Nujol)/cm$^{-1}$ 3111, 3082, 3072, 1529, 1467, 1425, 1254, 1238 and 1205; NMR $\delta_H$(400MHz, CDCl$_3$) 7.28(1H, dd, J 5.0, 4.0Hz), 7.54(1H, d, J 5.5Hz), 7.69(1H, dd, J 5.0, 1.0Hz), |

TABLE 2-continued

Analytical data
HPLC is carried out using the following conditions: Column.
Supelcosil ABZ+ (170 × 4.6 mm),
particle size 5 μM, mobile phase MeOH: 10 mM aq
NH$_4$OAc (80:20), (70:30) or (60:40) (specified
in Table 2), flow rate 1.0 mL/min.,
detection wavelength λ = 230 nM
(unless otherwise stated), retention
times are provided in Table 2.

| Example | Yield(%) | Physical Data |
|---|---|---|
|  |  | 8.07(1H, d, J 5.5Hz), 8.08(1H, dd, J 4.0, 1.0Hz); Anal. Calcd for C$_{10}$H$_5$ClN$_2$S$_2$: C, 47.52; H, 1.99, N, 11.08. Found: C, 47.54; H, 2.00; N, 10.93; M/Z 253(M+H)+. |
| 2 | 98 | mp 139.2-140.0° C.; IR ν$_{max}$(Nujol)/cm$^{-1}$ 1551, 1517, 1466, 1393, 1361, 793 and 707; NMR δ$_H$(400MHz, CDCl$_3$) 3.30(6H, s), 7.22(1H, dd, J 5.0, 4.0Hz), 7.27(1H, d, J 5.5Hz), 7.54(1H, dd, J 5.5, 1.0Hz), 7.79(1H, d, J 5.5Hz), 7.95(1H, dd, J 3.5, 1.0Hz); Anal. Calcd for C$_{12}$H$_{11}$N$_3$S$_2$: C, 55.15; H, 4.24, N, 16.07. Found: C, 55.05; H, 4.12; N, 15.88. |
| 3 | 52 | mp 146.9-147.6° C.; IR ν$_{max}$(Nujol)/cm$^{-1}$ 3132, 3105, 3064, 1594, 1522, 1463 and 1264; NMR δ$_H$(400MHz, CDCl$_3$) 6.69-6.72(1H, m), 5.50(1H, d, J 5.5Hz), 7.60(1H, dd, J 3.5, 1.0Hz), 7.80(1H, d, J 1.0Hz), 8.10(1H, d, J 5.5Hz); Anal. Calcd for C$_{10}$H$_5$ClN$_2$OS+0.4 H$_2$O: C, 49.25; H, 2.40, N, 11.49. Found: C, 48.87; H, 2.04; N, 11.65. |
| 4 | 78 | mp 128.5-128.9° C.; IR ν$_{max}$(Nujol)/cm$^{-1}$ 3314, 3065, 1542, 1498, 1466 and 1363; NMR δ$_H$(400MHz, CDCl$_3$) 1.71-1.81(1H, m), 1.88-2.08 (2H, m), 2.13-2.23(1H, m), 3.68-3.79(3H, m), 3.82-3.98(2H, m), 4.40(1H, s), 7.21-7.27(2H, m), 7.56(1H, dd, J 5.0, 1.0Hz), 7.83(1H, d, J 5.5Hz), 7.98(1H, dd, J 4.0, 1.0Hz); Anal. Calcd for C$_{15}$H$_{15}$N$_3$OS$_2$: C, 56.76; H, 4.76, N, 13.23. Found: C, 56.72; H, 4.80; N, 13.14. |
| 5 | 77 | mp 129.3-130.4° C.; IR ν$_{max}$(Nujol)/cm$^{-1}$ 3125, 3095, 3066, 1601, 1554, 1462, 1403 and 792; NMR δ$_H$(400MHz, CDCl$_3$) 3.29(6H, s), 6.60-6.64(1H, m), 7.23(1H, d, J 5.5Hz), 7.38(1H, d, J 3.5Hz), 7.70-7.72 (1H, m), 7.80-7.84(1H, d, J 5.5Hz); Anal. Calcd for C$_{12}$H$_{11}$N$_3$OS: C, 58.76; H, 4.52, N, 17.12. Found: C, 58.89; H, 4.52; N, 16.89. |
| 6 | 75 | mp dec. >230° C.; IR ν$_{max}$(Nujol)/cm$^{-1}$ 3426, 3160, 3075, 1616, 1573, 1523 and 1447; NMR δ$_H$(400MHz, DMSO) 2.13-2.22(2H, m), 3.45 (2H, t, J 6.5Hz), 4.33(2H, t, J 7.0Hz), 4.49-4.87(1H, s), 7.36-7.39 (1H, m), 7.43-7.46(1H, m), 7.69-7.72(1H, m), 7.84-7.87(1H, m), 8.00(1H, d, J 4.5Hz), 8.04(1H, d, J 4.0Hz), 8.42(1H, d, J 5.5Hz), 9.23 (1H, s); Anal. Calcd for C$_{16}$H$_{15}$N$_5$S$_2$+2HCl+0.25 H$_2$O: C, 44.44, H, 4.43, N, 16.20. Found: C, 44.09; H, 4.34; N, 16.14. |
| 7 | 61 | mp 110.6-111.8° C.; IR ν$_{max}$(Nujol)/cm$^{-1}$ 3266, 1590, 1553, 1516, 1461 and 791; NMR δ$_H$(400MHz, CDCl$_3$) 3.67-3.73(2H, m), 3.89-3.93 (2H, m), 3.93-4.08(1H, s), 5.56(1H, t, J 5.0Hz), 7.21-7.25(2H, m), 7.56(1H, dd, J 5.0, 1.0Hz), 7.83(1H, d, J 5.5Hz), 7.97(1H, dd, J 3.5, 1.0Hz); Anal. Calcd for C$_{12}$H$_{11}$N$_3$OS$_2$: C, 51.97, H, 4.00, N, 15.14. Found: C, 51.75; H, 3.96; N, 15.11. |
| 8 | 95 | mp 114.6-115.1° C.; IR ν$_{max}$(Nujol)/cm$^{-1}$ 3412, 3059, 1549, 1481, 1464, 1341, 1327 and 725; NMR δ$_H$(400MHz, CDCl$_3$) 4.13(3H, s), 7.24-7.27(1H, m), 7.42(1H, d, J 5.5Hz), 7.62(1H, dd, J 5.0, 1.0Hz), 7.96(1H, d, J 5.5Hz), 8.04(1H, dd, J 3.5, 1.0Hz); Anal. Calcd for C$_{11}$H$_8$N$_2$OS$_2$: C, 53.21, H, 3.25, N, 11.28. Found: C, 53.21; H, 3.27; N, 11.24. |
| 9 | 36 | IR ν$_{max}$(Nujol)/cm$^{-1}$ 3065, 2925, 2855, 1539, 1464, 1352, 716; NMR δ$_H$ (400MHz, CDCl$_3$) 1.50(3H, t J 7.5Hz), 3.10(2H, q, J 7.5Hz), 7.26 (1H, m), 7.54(1H, d, J 5.5Hz), 7.61(1H, dd, J 1.0, 5.0Hz), 7.96(1H, d, J 5.5Hz), 8.04(1H, dd, J 1.0, 3.8Hz). |
| 10 | 57 | mp dec. >235° C.; IR ν$_{max}$(Nujol)/cm$^{-1}$ 3417, 3105, 2623, 1654, 1633, 1508 and 1466; NMR δ$_H$(400MHz, DMSO) 2.13-2.22(2H, m), 3.49 (2H, t, J 6.5Hz), 4.33(2H, t, J 7.0Hz), 4.02-4.66(2H, s), 6.88-6.90 (1H, m), 7.45(1H, s), 7.51(1H, s), 7.70(1H, t, J 1.7Hz), 7.85(1H, t, J 1.7Hz), 8.23(1H, s), 8.45(1H, d, J 5.0Hz), 9.22(1H, s), 14.59-14.87 (1H, s); Anal. Calcd for C$_{16}$H$_{15}$N$_5$OS+2HCl+1.5 H$_2$O: C, 45.18, H, 4.74, N, 16.47, Cl, 16.67. Found: C, 45.40; H, 4.39; N, 16.59, Cl, 16.42. |
| 11 | 82 | mp 147.6-148.8° C.; IR ν$_{max}$(Nujol)/cm$^{-1}$ 3141, 3112, 3074, 1594, 1536, 1524, 1487, 1471, 1239, 1192, 1167, 1131 and 810; NMR δ$_H$(400MHz, CDCl$_3$) 6.71-6.73(1H, m), 7.66(1H, dd, J 3.5, 1.0Hz), 7.69(1H, d, J 5.5Hz), 7.81-7.83(1H, m), 8.19(1H, d, J 5.5Hz); Anal. Calcd for C$_{11}$H$_5$F$_3$N$_2$OS: C, 48.89, H, 1.86, N, 10.36. Found: C, 48.67; H, 1.92; N, 10.25. |
| 12 | 78 | mp 164.4-164.9° C.; IR ν$_{max}$(Nujol)/cm$^{-1}$ 3153, 3121, 1596, 1498, 1466, 1272 and 804; NMR δ$_H$(400MHz, CDCl$_3$) 2.51(3H, s), 6.68-6.70 (1H, m), 7.57(1H, dd, J 3.5, 1.0Hz), 7.72(1H, dd, J 2.5, 1.0Hz), 7.78-7.79(1H, m); Anal. Calcd for C$_{11}$H$_7$ClN$_2$OS: C, 52.70, H, 2.82, N, 11.17. Found: C, 52.91; H, 2.82; N, 11.05. |

TABLE 2-continued

Analytical data
HPLC is carried out using the following conditions: Column.
Supelcosil ABZ⁺ (170 × 4.6 mm),
particle size 5 μM, mobile phase MeOH: 10 mM aq
NH$_4$OAc (80:20), (70:30) or (60:40) (specified
in Table 2), flow rate 1.0 mL/min.,
detection wavelength λ = 230 nM
(unless otherwise stated), retention
times are provided in Table 2.

| Example | Yield(%) | Physical Data |
|---|---|---|
| 13 | 34 | mp dec. 213.9° C.; IR ν$_{max}$(Nujol)/cm$^{-1}$ 3142, 3113, 3898, 3070, 1594, 1515, 1460, 1271 and 765; NMR δ$_H$(400MHz, DMSO) 6.90-6.93(1H, m), 7.68(1H, d, J 3.5Hz), 8.27(1H, s), 8.83(1H, s); Anal. Calcd for C$_{10}$H$_4$BrClN$_2$OS: C, 38.06, H, 1.28, N, 8.87. Found: C, 38.22; H, 1.38; N, 8.74. |
| 14 | 75 | mp 107.9-108.9° C.; IR ν$_{max}$(Nujol)/cm$^{-1}$ 3279, 1607, 1572, 1460, 1377, 1067 and 791; NMR δ$_H$(400MHz, CDCl$_3$) 3.66-3.72(2H, m), 3.88-3.93(2H, m), 4.33-4.60(1H, s), 5.56(1H, t, J 5.0Hz), 6.62-6.65 (1H, m), 7.21(1H, d, J 5.5Hz), 7.38(1H, d, J 3.5Hz), 7.73(1H, s), 7.88(1H, d, J 5.5Hz); Anal. Calcd for C$_{12}$H$_{11}$N$_3$O$_2$S: C, 55.16, H, 4.24, N, 16.07. Found: C, 55.16; H, 4.23; N, 15.97. |
| 15 | 38 | mp 173.4-174.4° C.; IR ν$_{max}$(Nujol)/cm$^{-1}$ 3394, 3260, 3110, 3083, 1600, 1555, 1463 and 1439; NMR δ$_H$(400MHz, CDCl$_3$) 3.70-3.72 (2H, m), 3.89-3.95(2H, m), 4.47-4.67(1H, s), 5.67-5.74(1H, m), 6.64-6.67(1H, m), 7.40(1H, d, J 3.5Hz), 7.74(1H, s), 7.87(1H, s); Anal. Calcd for C$_{12}$H$_{10}$BrN$_3$O$_2$S+0.25 H$_2$O: C, 41.27; H, 3.18, N, 12.03. Found: C, 41.28; H, 3.04; N, 12.04. |
| 16 | 75 | mp 149.9-150.6° C.; IR ν$_{max}$(Nujol)/cm$^{-1}$ 3404, 3219, 1602, 1550, 1507, 1464 and 1440; NMR δ$_H$(400MHz, CDCl$_3$) 2.38(3H, s), 3.67-3.73 (2H, m), 3.88-3.94(2H, m), 5.13(1H, s), 5.57(1H, t, J 5.0Hz), 6.62-6.64(1H, m), 7.37(1H, dd, J 3.5, 1.0Hz), 7.51(1H, d, J 1.0Hz), 7.72-7.73(1H, m); Anal. Calcd for C$_{13}$H$_{13}$N$_3$O$_2$S: C, 56.71; H, 4.76, N, 15.25. Found: C, 56.67; H, 4.79; N, 15.19. |
| 17 | 64 | mp 231.0-231.6° C.; IR ν$_{max}$(Nujol)/cm$^{-1}$ 3109, 3094, 1531, 1469, 1232 and 790; NMR δ$_H$(400MHz, DMSO) 7.48-7.58(2H, m), 7.72(1H, d, J 5.5Hz), 8.10-8.17(2H, m), 8.52(1H, s), 8.75(1H, d, J 5.5Hz); Anal. Calcd for C$_{14}$H$_7$ClN$_2$S$_2$: C, 55.33; H, 2.33, N, 9.25. Found: C, 55.22; H, 2.32; N, 9.41. |
| 18 | 56 | IR ν$_{max}$(Nujol)/cm$^{-1}$ 3096, 2924, 1595, 1528, 1488, 1463, 1303, 1016, 808 and 768; NMR δ$_H$(400MHz, DMSO) 1.36(3H, t, J 7.7Hz), 3.00 (2H, q, J 7.7Hz), 6.85(1H, dd, J 1.8, 3.5Hz), 7.54(1H, dd, J 0.8, 3.5Hz), 7.58(1H, d, J 5.5Hz), 8.17(1H, dd, J 0.8, 1.8Hz), 8.49(1H, d, J 5.5Hz). |
| 19 | 89 | mp 166.5-167.3° C.; IR ν$_{max}$(Nujol)/cm$^{-1}$ 3094, 3053, 1556, 1463, 1407, 1354 and 793; NMR δ$_H$(400MHz, CDCl$_3$) 3.33(6H, s), 7.29(1H, d, J 5.5Hz), 7.37-7.43(2H, m), 7.82(1H, d, J 5.5Hz), 7.87-7.92(2H, m), 8.16(1H, s); Anal. Calcd for C$_{16}$H$_{13}$N$_3$S$_2$: C, 61.71; H, 4.21, N, 13.49. Found: C, 61.82; H, 4.26; N, 13.52. |
| 20 | 64 | mp 173.4-174.4° C.; IR ν$_{max}$(Nujol)/cm$^{-1}$ 3409, 3260, 3126, 3094, 1587, 1545 and 1339; NMR δ$_H$(400MHz, CDCl$_3$) 3.70-3.77(2H, m), 3.90-3.97(2H, m), 5.60(1H, t, J 5.0Hz), 7.27(1H, d, J 5.5Hz), 7.39-7.46 (2H, m), 7.86-7.93(3H, m), 8.19(1H, s); Anal. Calcd for C$_{16}$H$_{13}$N$_3$OS$_2$+0.25 H$_2$O: C, 57.93; H, 4.10, N, 12.66. Found: C, 57.78; H, 3.96; N, 12.76. |
| 21 | 42 | mp 112.3-122.7° C.; NMR δ$_H$(400MHz, CDCl$_3$) 1.30(3H, t, J 7.3Hz), 3.54-3.62(2H, m), 5.06(1H, s), 7.26(1H, d, J 5.5Hz), 7.45-7.48(1H, m), 7.81(1H, d, J 5.5Hz), 7.90(1H, dd, J 5.0Hz), 8.20-8.23(1H, m); Anal. Calcd for C$_{12}$H$_{11}$N$_3$S$_2$: C, 55.15; H, 4.24, N, 16.07. Found: C, 55.13; H, 4.29; N, 15.90. |
| 22 | 63 | mp 118.7-119.5° C.; IR ν$_{max}$(Nujol)/cm$^{-1}$ 3094, 1602, 1552, 1464 and 1377; NMR δ$_H$(400MHz, CDCl$_3$) 3.33(6H, s), 6.61-6.64(1H, m), 7.40(1H, d, J 3.5Hz), 7.71-7.72(1H, m), 7.81(1H, s); Anal. Calcd for C$_{12}$H$_{10}$BrN$_3$OS: C, 44.46; H, 3.11, N, 12.96. Found: C, 44.24; H, 3.06; N, 13.01. |
| 23 | 90 | mp 113.1-113.7° C.; IR ν$_{max}$(Nujol)/cm$^{-1}$ 3115, 1602, 1560, 1548, 1508, 1466 and 1409; NMR δ$_H$(400MHz, CDCl$_3$) 2.38(3H, s), 3.31 (6H, s), 6.58-6.62(1H, m), 7.36(1H, d, J 3.5Hz), 7.44-7.45(1H, m), 7.69-7.70(1H, m); Anal. Calcd for C$_{16}$H$_{13}$N$_3$OS+0.15 H$_2$O: C, 59.59; H, 5.12, N, 16.04. Found: C, 59.83; H, 2.89; N, 15.70. |
| 24 | 31 | mp 209.2-209.5° C.; IR ν$_{max}$(Nujol)/cm$^{-1}$ 1531, 1523, 1463, 1377, 1247 and 781; NMR δ$_H$(400MHz, CDCl$_3$) 7.47(1H, m), 7.54(1H, d, J 6.0Hz), 7.95(1H, dt, J 8.0, 2.0Hz), 8.19(1H, d, J 5.5Hz), 8.73-8.77(1H, m), 8.84-8.87(1H, m); Anal. Calcd for C$_{11}$H$_6$ClN$_3$S+0.1 H$_2$O: C, 52.56; H, 2.45, N, 16.72. Found: C, 52.69; H, 2.41; N, 16.64. |

TABLE 2-continued

Analytical data
HPLC is carried out using the following conditions: Column.
Supelcosil ABZ+ (170 × 4.6 mm),
particle size 5 μM, mobile phase MeOH: 10 mM aq
NH$_4$OAc (80:20), (70:30) or (60:40) (specified
in Table 2), flow rate 1.0 mL/min.,
detection wavelength λ = 230 nM
(unless otherwise stated), retention
times are provided in Table 2.

| Example | Yield(%) | Physical Data |
|---|---|---|
| 25 | | IR ν$_{max}$(Nujol)/cm$^{-1}$ 2955, 2924, 2854, 1600, 1555, 1526, 1490, 1456, 1378 and 1270; NMR δ$_H$(400MHz, DMSO) 8.18(1H, m) 7.97(1H, s), 7.35(1H, m), 7.14(1H, m), 6.67(1H, m), 3.68-3.58(4H, m), 3.58-3.48 (4H, m). |
| 26 | | IR ν$_{max}$(Nujol)/cm$^{-1}$ 3261, 2924, 2854, 1604, 1573, 1547, 1513, 1455, 1443 and 1330; NMR δ$_H$(400MHz, CDCl$_3$) 7.86(1H, d, J 5.5Hz), 7.72 (1H, s), 7.48-7.23(7H, m), 6.62(1H, dd, J 4.0, 1.5Hz), 5.53(1H, br s), 4.76(2H, d, J 5.9Hz). |
| 27 | 13 | mp 186.6-188.0° C.; IR ν$_{max}$(Nujol)/cm$^{-1}$ 3053, 1556, 1466, 1359 and 786; NMR δ$_H$(400MHz, CDCl$_3$) 3.37(6H, s), 7.27-7.33(1H, m), 7.39-7.45 (1H, m), 7.86-7.95(2H, m), 8.66(1H, d, J 8.0Hz), 8.81-8.84 (1H, m). |
| 28 | 40 | mp 197.1-197.7° C.; IR ν$_{max}$(Nujol)/cm$^{-1}$ 3406, 3103, 3084, 1569, 1520 and 1464; NMR δ$_H$(400MHz, CDCl$_3$) 6.49-6.50(1H, m), 7.14(1H, dt, J 3.0, 1.0Hz), 7.20-7.23(1H, m), 7.48(1H, d, J 5.5Hz), 8.01(1H, d, J 5.5Hz), 9.88-10.01(1H, s); Anal. Calcd for C$_{10}$H$_6$ClN$_3$S: C, 50.96; H, 2.57, N, 17.82. Found: C, 50.87; H, 2.54; N, 17.64. |
| 29 | 31 | IR ν$_{max}$(Nujol)/cm$^{-1}$ 2924, 2854, 1739, 1727, 1598, 1532, 1467, 1369, 1348 and 1191; NMR δ$_H$(400MHz, CDCl$_3$) 8.05(1H, m), 7.78(1H, m), 7.60(1H, m), 7.49(1H, m), 6.42(1H, m), 4.20(2H, q, J 7.0Hz), 4.18 (2H, s) and 1.22(3H, t, J 7.0Hz); M/Z 289(M+H)$^+$. |
| 30 | 67 | mp 183.2-183.8° C.; IR ν$_{max}$(Nujol)/cm$^{-1}$ 3071, 1536, 1522, 1465 and 1252; NMR δ$_H$(400MHz, CDCl$_3$) 7.58(1H, d, J 5.5Hz), 8.23(1H, d, J 5.5Hz), 8.79-8.83(2H, m), 9.95(1H, d, J 1.5Hz); Anal. Calcd for C$_{10}$H$_5$ClN$_4$S: C, 48.30; H, 2.03, N, 22.52. Found: C, 48.28; H, 2.10; N, 22.40. |
| 31 | 15 | IR ν$_{max}$(Nujol)/cm$^{-1}$ 2726, 1561, 1509, 1461 and 1377; NMR δ$_H$(400MHz, CDCl$_3$) 3.35(6H, s), 6.54-6.55(1H, m), 6.62-6.64(1H, m), 7.41(1H, dd, J 3.5, 1.0Hz), 7.45(1H, d, J 3.5Hz), 7.48-7.49(1H, m), 7.72-7.73(1H, m), 8.05(1H, s); Anal. Calcd for C$_{16}$H$_{13}$N$_3$O$_2$S+0.3 H$_2$O: C, 60.67; H, 4.33, N, 13.27. Found: C, 60.49; H, 4.09; N, 13.33. |
| 32 | 94 | mp 247.4-248.6° C.; IR ν$_{max}$(Nujol)/cm$^{-1}$ 3080, 3072, 1568, 1544, 1462 and 1402; NMR δ$_H$(400MHz, CDCl$_3$) 3.29(6H, s), 6.41-6.44(1H, m), 7.04-7.06(1H, m), 7.09-7.12(1H, m), 7.23(1H, d, J 5.5Hz), 7.76 (1H, d, J 5.0Hz), 9.74-9.83(1H, s); Anal. Calcd for C$_{12}$H$_{12}$N$_4$S+0.2 H$_2$O: C, 58.14; H, 5.04, N, 22.60. Found: C, 58.16; H, 4.84; N, 22.64. |
| 33 | 100 | mp 173.9-174.3° C.; IR ν$_{max}$(Nujol)/cm$^{-1}$ 1586, 1558, 1531, 1462, 1352 and 793; NMR δ$_H$(400MHz, CDCl$_3$) 3.36(6H, s), 7.29(1H, d, J 5.5Hz), 7.92(1H, d, J 5.5Hz), 8.70(1H, d, J 2.5Hz), 8.76-8.78(1H, m), 8.76-8.78(1H, m), 9.87(1H, d, J 1.5Hz); Anal. Calcd for C$_{12}$H$_{11}$N$_5$S+0.1 H$_2$O: C, 55.62; H, 4.36, N, 27.03. Found: C, 55.46; H, 4.25; N, 26.83. |
| 34 | 55 | mp 191.5-192.4° C.; IR ν$_{max}$(Nujol)/cm$^{-1}$ 3298, 3082, 3060, 1589, 1567, 1533, 1465, 1344, 1062 and 797; NMR δ$_H$(400MHz, DMSO) 3.47-3.56(2H, m), 3.57-3.65(2H, m), 4.73(1H, s), 7.19(1H, s), 7.28 (1H, d, J 5.0Hz), 8.31(1H, d, J 5.5Hz), 8.86(1H, d, J 2.5Hz), 8.91 (1H, dd, J 2.5, 1.5Hz), 9.72(1H, s). |
| 35 | | IR ν$_{max}$(Nujol)/cm$^{-1}$ 3140, 3089, 2925, 2854, 1601, 1552, 1527, 1519, 1493, 1455 and 1265; NMR δ$_H$(400MHz, CDCl$_3$) 7.85(1H, d, J 5.5Hz), 7.72(1H, s), 7.38(1H, m), 7.22(1H, d, J 5.5Hz), 6.65(1H, m), 4.05-3.91(4H, m), 2.68-2.53(4H, m), 2.41(3H, s). |
| 36 | | IR ν$_{max}$(Nujol)/cm$^{-1}$ 3107, 3080, 2963, 2927, 2865, 1596, 1525, 1484, 1463, 1272 and 1236; NMR δ$_H$(400MHz, CDCl$_3$) 7.97(1H, d, J 5.5Hz), 7.77(1H, s), 7.48(1H, m), 7.39(1H, d, J 5.5Hz), 6.67(1H, m), 4.13(1H, sept, J 7.0Hz), 1.52(3H, d, J 7.0Hz). |
| 37 | 95 | mp 207-208° C.; IR ν$_{max}$(Nujol)/cm$^{-1}$ 3073, 2956, 1592, 1513, 1462 1263, 1012, 794 and 768; NMR δ$_H$(400MHz, CDCl$_3$) 1.47(3H, t, J 7.5Hz), 3.28(2H, q, J 7.5Hz), 6.66(1H, dd, J 3.5, 1.5Hz), 7.49(1H, d, J 5.5Hz), 7.74-7.79(1H, m) and 7.97(1H, d, J 5.5Hz) |
| 38 | 75 | mp 109-110° C.; IR ν$_{max}$(Nujol)/cm$^{-1}$ 3314, 2927, 1598, 1551, 1379, 1346, 1078, 795 and 744; NMR δ$_H$(400MHz, CDCl$_3$) 1.60-1.80(2H, m), 1.86-2.07(2H, m), 2.14-2.26(1H, m), 3.64-3.99(4H, m), 4.38 (1H, m), 6.61-6.66(2H, m), 7.22-7.28(1H, m), 7.41(1H, d, J 3.5Hz), 7.74(1H, d, J 2.5Hz) and 7.88(1H, d, J 5.5Hz) |
| 39 | 66 | IR ν$_{max}$(Nujol)/cm$^{-1}$ 3058, 22925, 1595, 1524, 1462, 1268 and 794; NMR δ$_H$(400MHz, CDCl$_3$) 2.69(3H, s), 6.66(1H, dd, J 4.0, 2.0Hz), 7.42(1H, d, J 5.5Hz), 7.51(1H, d, J 3.5Hz), 7.76(1H, d, J 2.5Hz) and 7.98(1H, d, J 5.5Hz) |

TABLE 2-continued

Analytical data
HPLC is carried out using the following conditions: Column.
Supelcosil ABZ⁺ (170 × 4.6 mm),
particle size 5 µM, mobile phase MeOH: 10 mM aq
NH₄OAc (80:20), (70:30) or (60:40) (specified
in Table 2), flow rate 1.0 mL/min.,
detection wavelength λ = 230 nM
(unless otherwise stated), retention
times are provided in Table 2.

| Example | Yield(%) | Physical Data |
|---|---|---|
| 40 | 73 | mp 101-102° C.; IR $v_{max}$(Nujol)/cm$^{-1}$ 3255, 2925, 1610, 1550, 1515, 1446, 1331, 907 and 793; NMR $\delta_H$(400MHz, CDCl₃) 4.16-4.23(2H, m), 5.16(1H, dq, J 10.0, 1.5Hz), 5.21-5.29(1H, m); 5.32(1H, dq, J 17.0, 1.5Hz), 5.97-6.09(1H, m), 6.63(1H, dd, J 3.5, 2.0Hz), 7.25(1H, d, J 5.5Hz), 7.39(1H, d, J 3.5Hz), 7.73(1H, dd, J 2.5, 1.0Hz) and 7.86 (1H, d, J 5.5Hz) |
| 41 | 56 | mp 220.5-221.0° C; IR $v_{max}$(Nujol)/cm$^{-1}$ 3135, 3082, 3080, 1594, 1544, 1519, 1505, 1463, 1341, 1265, 867, 782 and 750; NMR $\delta_H$(400MHz, DMSO) 6.94-6.96(1H, m), 7.75(1H, dd, J 3.5, 1.0Hz), 8.33 (1H, d, J 1.0Hz), 9.79(1H, s); Anal. Calcd for C₁₀H₄ClN₅O₃S₂O: C, 42.64; H, 1.43, N, 14.91. Found: C, 42.94; H, 1.81; N, 15.05. |
| 42 | | IR $v_{max}$(Nujol)/cm$^{-1}$ 3261, 2925, 2854, 1608, 1599, 1549, 1516, 1458, 1377 and 1329. NMR $\delta_H$(400MHz, CDCl₃) 7.86(1H, d, J 5.5Hz), 7.72 (1H, s), 7.38(1H, m), 7.25(1H, d, J 5.5Hz), 7.65(1H, m), 5.16(1H, br s), 5.59(2H, q, J 8.5Hz), 1.32(3H, t, J 8.5Hz). |
| 43 | | IR $v_{max}$(Nujol)/cm$^{-1}$ 2956, 2925, 2855, 1598, 1547, 1521, 1508, 1478, 1458 and 1349; NMR $\delta_H$(400MHz, CDCl₃) 7.80(1H, m), 7.72(1H, m), 7.39(1H, m), 7.22(1H, m), 6.62(1H, m), 3.68(4H, m) and 2.02(4H, m). |
| 44 | 21 | mp 182.8-183.8° C.; IR $v_{max}$(Nujol)/cm$^{-1}$ 3152, 3128, 3107, 1601, 1558, 1543, 1498, 1477, 1406, 1321, 765 and 756; NMR $\delta_H$(400MHz, CDCl₃) 3.35(6H, s), 6.65-6.67(1H, m), 7.45(1H, d, J 3.5Hz), 7.74 -7.75 (1H, m), 8.88(1H, s); Anal. Calcd for C₁₂H₁₀N₄O₃S: C, 49.65; H, 3.47, N, 19.29. Found: C, 49.27; H, 3.49; N, 19.04. |
| 45 | | IR $v_{max}$(Nujol)/cm$^{-1}$ 3250, 3084, 2924, 2854, 1608, 1580, 1548, 1515, 1485, 1443 and 1330; NMR $\delta_H$(400MHz, CDCl₃) 8.59(1H, m), 7.88 (1H, m), 7.72(1H, m), 7.66(1H, m), 7.41-7.38(1H, m), 7.25(1H, m), 7.18(1H, m), 6.63(1H, m), 6.21(1H, br s) and 4.89(2H, d, J 5.6Hz). |
| 46 | 44 | IR $v_{max}$(Nujol)/cm$^{-1}$ 3094, 2926, 2855, 1716, 1593, 1523, 1489, 1468, 1421, 1332 and 1190; NMR $\delta_H$(400MHz, CDCl₃) 8.00(1H, m), 7.78 (1H, m), 7.50(2H, m), 6.62(1H, m), 4.15(2H, m), 3.40(2H, m), 2.95 (2H, m) and 1.20(3H, t, J 7.0Hz); M/Z 303(M+H)⁺. |
| 47 | | IR $v_{max}$(Nujol)/cm$^{-1}$ 3417, 3103, 2974, 2944, 2859, 2820, 2776, 1599, 1556, 1538, 1488, 1462, 1337 and 1256. NMR $\delta_H$(400MHz, CDCl₃) 7.84(1H, d, J 5.5Hz), 7.73(1H, s), 7.38(1H, m), 7.22(1H, d, J 5.5Hz), 6.63(1H, m), 5.64(1H, br s), 3.60(2H, q, J 6.0Hz), 2.59(2H, t, J 6.0Hz), 2.28(6H, s). |
| 48 | 44 | NMR $\delta_H$(400MHz, CDCl₃) 8.01(1H, m), 7.79(1H, m), 7.50(2H, m), 6.80(1H, m), 4.10(1H, br m), 3.80(2H, m), 3.30(2H, m) and 2.18(2H, m); Retention time 2.42(80:20). |
| 49 | 81 | IR $v_{max}$(Nujol)/cm$^{-1}$ 3079, 2923, 1745, 1729, 1698, 1594, 1531, 1466, 1336, 809; NMR $\delta_H$(400MHz, DMSO) 2.84(2H, t, J 7.0Hz), 3.24(2H, t, J 7.0Hz), 6.86(1H, dd, J 1.8, 3.5Hz), 7.54(1H, dd, J 0.8, 3.5Hz), 7.58(1H, d, J 5.5Hz), 8.17(1H, dd, J 0.8, 1.8Hz), 8.51(1H, d, J 5.5Hz), 12.05(1H, br). |
| 50 | 25 | NMR $\delta_H$(400MHz, CDCl₃) 1.85(2H, m), 1.95(2H, m), 2.95(2H, t, J 7.8Hz), 3.50(6H, m), 6.65(1H, dd, J 1.7, 3.5Hz), 7.48(2H, m), 7.76 (1H, m), 7.99(1H, d, J 5.5Hz). |
| 51 | 82 | mp 145.8-146.5° C.; IR $v_{max}$(Nujol)/cm$^{-1}$ 3403, 3310, 3135, 1600, 1551, 1517, 1463 and 750; NMR $\delta_H$(400MHz, CDCl₃) 3.30(6H, s), 4.13(2H, s), 6.59-6.61(2H, m), 7.35(1H, dd, J 3.5, 1.0Hz), 7.68-7.71 (1H, m); Anal. Calcd for C₁₂H₁₂N₄OS+0.3 H₂O: C, 54.24; H, 4.78, N, 21.08. Found: C, 54.37; H, 4.51; N, 20.93. |
| 52 | 52 | IR $v_{max}$(Nujol)/cm$^{-1}$ 3070, 2924, 2854, 1541, 1464, 1352, 779, 650; NMR $\delta_H$(400MHz, CDCl₃) 1.50(3H, t, J 7.50Hz), 3.20(2H, q, J 7.50Hz), 7.45(1H, m), 7.53(1H, d, J 5.6Hz), 7.92(1H, m), 8.07(1H, d, J 5.6Hz), 8.79(1H, m), 8.85(1H, m). |
| 53 | | IR $v_{max}$(Nujol)/cm$^{-1}$ 2924, 2854, 1567, 1548, 1522, 1461, 1440, 1377 and 1353; NMR $\delta_H$(400MHz, CDCl₃) 7.80(1H, d, J 5.5Hz), 7.67(1H, d, J 4.0Hz), 7.26(1H, d, J 5.5Hz), 7.02(1H, d, J 4.0Hz), 3.28(6H, s). |
| 54 | 25 | NMR $\delta_H$(400MHz, CDCl₃) 3.35(2H, m), 4.12(2H, m), 4.41(1H, m), 6.65(1H, d, J 1.8, 3.5Hz), 7.46(2H, m), 7.78(1H, d, J 0.8, 1.8Hz), 8.05 (1H, d, J 5.5Hz). |
| 55 | 52 | mp 244.4-244.9° C.; IR $v_{max}$(Nujol)/cm$^{-1}$ 3309, 3139, 1663, 1652, 1602, 1557, 1510, 1490, 1470, 1465, 1446, 1377 and 743; NMR $\delta_H$(400MHz, CDCl₃) 3.23(6H, s), 6.61-6.63(1H, m), 6.75(1H, s), 7.17-7.22 (1H, m), 7.34-7.46(5H, m), 7.72(1H, s), 7.93(1H, s), 8.04(1H, s). |

TABLE 2-continued

Analytical data
HPLC is carried out using the following conditions: Column.
Supelcosil ABZ+ (170 × 4.6 mm),
particle size 5 μM, mobile phase MeOH: 10 mM aq
NH$_4$OAc (80:20), (70:30) or (60:40) (specified
in Table 2), flow rate 1.0 mL/min.,
detection wavelength λ = 230 nM
(unless otherwise stated), retention
times are provided in Table 2.

| Example | Yield(%) | Physical Data |
|---|---|---|
| 56 | 51 | mp 210.9-211.3° C.; IR ν$_{max}$(Nujol)/cm$^{-1}$ 3346, 3140, 1666, 1558, 1541, 1462 and 1377; NMR δ$_H$(400MHz, CDCl$_3$) 2.29(3H, s), 3.31 (6H, s), 6.61-6.64(1H, m), 7.39(1H, d, J 3.5Hz), 7.73(1H, d, J 1.0Hz), 8.25(1H, s), 8.30(1H, s); Anal. Calcd for C$_{14}$H$_{14}$N$_4$O$_2$S: C, 55.62; H, 4.67, N, 18.52. Found: C, 55.46; H, 4.57; N, 18.27. |
| 57 | 47 | mp 192.2-192.8° C.; IR ν$_{max}$(Nujol)/cm$^{-1}$ 3409, 3133, 3110, 1665, 1603, 1550, 1526, 1463, 1376 and 1261; NMR δ$_H$(400MHz, CDCl$_3$) 3.33(6H, s), 6.62-6.64(1H, m), 7.40(1H, dd, J 3.5, 1.0Hz), 7.51-7.62(3H, m), 7.73-7.74(1H, m), 7.96-8.01(2H, m), 8.45(1H, s), 9.10(1H, s); Anal. Calcd for C$_{19}$H$_{16}$N$_4$O$_2$S+0.75 H$_2$O: C, 60.38; H, 4.67, N, 14.82. Found: C, 60.47; H, 4.63; N, 14.72. |
| 58 | 65 | mp 183.8-184.3° C.; IR ν$_{max}$(Nujol)/cm$^{-1}$ 3269, 3134, 3069, 1613, 1583, 1551, 1520, 1449 and 794; NMR δ$_H$(400MHz, CDCl$_3$) 3.10(3H, d, J 5.0Hz), 5.09-5.10(1H, s), 6.62-6.64(1H, m), 7.26(1H, d, J 4.5Hz), 7.38(1H, dd, J 3.5, 1.0Hz), 7.71-7.73(1H, m), 7.85(1H, d, J 5.5Hz); Anal. Calcd for C$_{11}$H$_9$N$_3$OS+0.3 H$_2$O: C, 55.82; H, 4.09, N, 17.75. Found: C, 55.85; H, 3.94; N, 17.68. |
| 59 | 6 | mp 211.9° C.; NMR δ$_H$(400MHz, CDCl$_3$) 3.09(3H, s), 6.72-6.74(1H, m), 7.40(1H, s), 7.63(1H, d, J 3.5Hz), 7.83(1H, d, J 1.0Hz), 7.90(1H, s); M/Z 330(M+H)$^+$. |
| 60 | 32 | mp 108.3-108.6° C.; IR ν$_{max}$(Nujol)/cm$^{-1}$ 3104, 3073, 1702, 1667, 1598, 1545, 1467, 1373, 804 and 744; NMR δ$_H$(400MHz, CDCl$_3$) 2.31 (3H, s), 3.66(3H, s), 3.96(2H, s), 6.68-6.70(1H, m), 7.42(1H, d, J 5.5Hz), 7.47(1H, d, J 3.5Hz), 7.87(1H, d, J 1.0Hz), 8.07(1H, d, J 5.5Hz); Anal. Calcd for C$_{15}$H$_{13}$N$_3$O$_3$S+0.2 H$_2$O: C, 56.49; H, 4.23, N, 13.17. Found: C, 56.63; H, 4.14; N, 13.09; M/Z 316(M+H)$^+$. |
| 61 | 23 | NMR δ$_H$(400MHz, CDCl$_3$) 3.69(2H, q, J 5.5Hz), 3.90(2H, t, J 4.5Hz), 5.47-5.58(1H, m), 7.03(1H, d, J 4.0Hz), 7.24(1H, d, J 5.5Hz), 7.71(1H, d, J 4.0Hz) and 7.84(1H, d, J 5.5Hz); Retention time(80/20): 5.12 min |
| 62 | 82 | IR ν$_{max}$(Nujol)/cm$^{-1}$ 2925, 2855, 1541, 1406, 1362, 783; NMR δ$_H$(400MHz, CDCl$_3$) 2.93(3H, s), 7.45(1H, m), 7.51(1H, d, J 5.6Hz), 7.92 (1H, m), 8.07(1H, d, J 5.6Hz), 8.76(1H, m), 8.85(1H, m). |
| 63 | 83 | IR ν$_{max}$(Nujol)/cm$^{-1}$ 3048, 2926, 2855, 1541, 1468, 1335, 790; NMR δ$_H$ (400MHz, CDCl$_3$) 1.05(3H, t, J 7.5Hz), 2.00(2H, sextet, J 7.5Hz), 3.10(2H, m), 7.45(1H, m), 7.51(1H, d, J 5.6Hz), 7.92(1H, m), 8.07 (1H, d, J 5.6Hz), 8.76(1H, m), 8.85(1H, m). |
| 64 | 26 | IR ν$_{max}$(Nujol)/cm$^{-1}$ 3418, 3096, 2924, 1516, 1460, 1377, 1228, 827 and 795; NMR δ$_H$(400MHz, CDCl$_3$) 7.55(1H, d, J 6.0Hz), 7.69(1H, d, J 3.0Hz), 8.18(1H, d, J 3.0Hz) and 8.20(1H, d, J 5.5Hz) |
| 65 | 62 | mp 152-153° C.; IR ν$_{max}$(Nujol)/cm$^{-1}$ 3056, 2925, 1566, 1532, 1464, 1354, 1132 and 792; NMR δ$_H$(400MHz, CDCl$_3$) 3.32(6H, s), 7.26(1H, d, J 5.5Hz), 7.54(1H, d, J, 3.0Hz), 7.91(1H, d, J 5.5Hz) and 8.10(1H, d, J 3.0Hz) |
| 66 | 10 | IR ν$_{max}$(Nujol)/cm$^{-1}$ 3057, 2956, 2855, 1530, 1467, 1450; NMR δ$_H$(400MHz, CDCl$_3$) 7.45(1H, m), 7.51(1H, d, J 5.6Hz), 7.92(1H, m), 8.07 (1H, d, J 5.6Hz), 8.76(1H, m), 8.85(1H, m), 9.28(1H, s). |
| 67 | | IR ν$_{max}$(Nujol)/cm$^{-1}$ 3288, 2956, 2925, 2554, 1597, 1584, 1557, 1523, 1459, 1427 and 1333. NMR δ$_H$(400MHz, CDCl$_3$) 8.82(1H, d, J 5.0Hz), 8.57(1H, d, J 8.0Hz), 7.95(1H, d, J 5.0Hz), 7.92-7.82(1H, m), 7.44 (7.40(1H, m), 7.29-7.22(1H, m), 5.60(1H, br s), 4.10(1H, br s), 3.95 -3.92 (2H, m), 3.77-3.75(2H, m). |
| 68 | 87 | mp 140-142° C.; IR ν$_{max}$(Nujol)/cm$^{-1}$ 3435, 2924, 1572, 1528, 1462, 1320, 1086, 793, 702 and 600; NMR δ$_H$(400MHz, CDCl$_3$) 3.73(2H, m), 3.93(2H, t, J 5.0Hz), 5.53-5.66(1H, m), 7.24(1H, d, J 5.5Hz), 7.96 (1H, d, J 5.5Hz) and 8.12(1H, d, J 3.0Hz) |
| 69 | 50 | NMR δ$_H$(400MHz, CDCl$_3$) 5.78(1H, dd, J 1.8, 10.5Hz), 6.68(1H, dd, J 1.7, 3.5Hz), 6.75(1H, dd, J 1.8, 17.3Hz), 7.05(1H, dd, J 10.5, 17.3 HZ), 7.53(1H, d, J 5.5Hz), 7.55(1H, dd, J 3.5, 5.5Hz), 7.78(1H, dd, J 0.8, 1.7Hz), 8.01(1H, d, J 5.5Hz). |
| 70 | 16 | IR ν$_{max}$(Nujol)/cm$^{-1}$ 3072, 2923, 1696, 1540, 1464, 788; NMR δ$_H$(400 MHZ, CDCl$_3$) 1.50(6H, d, J 6.9Hz), 3.44(1H, heptet, J 6.9Hz), 7.44 (1H, ddd, J 1.3, 4.9, 7.5Hz), 7.54(1H, d, J 5.5Hz), 7.93(1H, dt, J 1.3, 7.5Hz), 8.06(1H, d, J 5.5Hz), 8.81(1H, m), 8.85(1H, m). |
| 71 | 13 | mp 65.0-65.4° C.; IR ν$_{max}$(Nujol)/cm$^{-1}$ 3326, 3090, 1598, 1558, 1488, 1466, 1330 and 1088; NMR δ$_H$(400MHz, CDCl$_3$) 3.41(3H, s), 3.63 (2H, t, J 5.5Hz), 3.79(2H, q, J 5.5Hz), 5.61(1H, t, J 5.0Hz), 6.63-6.65 |

TABLE 2-continued

Analytical data
HPLC is carried out using the following conditions: Column.
Supelcosil ABZ+ (170 × 4.6 mm),
particle size 5 μM, mobile phase MeOH: 10 mM aq
$NH_4OAc$ (80:20), (70:30) or (60:40) (specified
in Table 2), flow rate 1.0 mL/min.,
detection wavelength λ = 230 nM
(unless otherwise stated), retention
times are provided in Table 2.

| Example | Yield(%) | Physical Data |
|---|---|---|
| | | (1H, m), 7.38(1H, d, J 3.0Hz), 7.72-7.73(1H, m), 7.84(1H, s); Anal. Calcd for $C_{13}H_{12}N_3BrO_2S$: C, 44.08; H, 3.41, N, 11.86. Found: C, 43.89; H, 3.48; N, 11.77. |
| 72 | 42 | mp 75.4-76.3° C.; IR $v_{max}$(Nujol)/cm$^{-1}$ 3288, 3098, 1597, 1548, 1516, 1462, 1376, 1341 and 767; NMR $\delta_H$(400MHz, $CDCl_3$) 1.68-1.80(1H, m), 1.83-2.08(2H, m), 2.17-2.28(1H, m), 3.65-3.81(2H, m), 3.82-3.90 (1H, m), 3.97-4.07(1H, m), 4.34-4.43(1H, m), 6.63-6.65(1H, m), 7.42(1H, d, J 1.0Hz), 7.73-7.74(1H, m), 7.85(1H, s). |
| 73 | 68 | IR $v_{max}$(Nujol)/cm$^{-1}$ 3061, 2925, 2854, 1727, 1595, 1523, 1484, 1467, 1377 and 1230; NMR $\delta_H$(400MHz, $CDCl_3$) 8.15(1H, m), 7.82(1H, m), 7.74(1H, m), 7.70(1H, m), 6.70(1H, m), 4.60(2H, q, J 7.0Hz), and 1.50(3H, t, J 7.0Hz). |
| 74 | 47 | NMR $\delta_H$(400MHz, $CDCl_3$) 1.43(9H, s), 3.42(2H, q, J 5.5Hz), 3.65 (2H, q, J 5.5Hz), 5.34(1H, t, J 5.5Hz), 6.63(1H, dd, J 2.0, 3.5Hz), 7.20 (1H, d, J 5.5Hz), 7.39(1H, d, J 3.5Hz), 7.72(1H, dd, J 1.0, 1.5Hz) and 7.85(1H, d, J 5.5Hz); Retention time 3.26 min(8:2) |
| 75 | 67 | NMR $\delta_H$(400MHz, $CDCl_3$) 1.40(2H, br s), 2.99(2H, t, J 6.0Hz), 3.60 (2H, q, J 6.0Hz), 5.40(1H, t, J 5.5Hz), 6.63(1H, dd, J 2.0, 3.5Hz), 7.22 (1H, d, J 5.5Hz), 7.37(1H, d, J 3.5Hz), 7.72(1H, dd, J 1.0, 2.0Hz) and 7.84(1H, d, J 5.5Hz); Retention time 2.65 min (7:3) |
| 76 | 49 | mp 112-113° C.; IR $v_{max}$(Nujol)/cm$^{-1}$ 3089, 2925, 1561, 1352, 1136 and 794; NMR $\delta_H$(400MHz, $CDCl_3$) 2.60(3H, s), 3.31(6H, s), 7.09(1H, s), 7.24(1H, d, J 5.5Hz) and 7.90(1H, d, J 5.5Hz) |
| 77 | 5 | NMR $\delta_H$(400MHz, $CDCl_3$) 3.61(2H, q, J 6.0Hz), 3.75(2H, q, J 6.0Hz), 5.56(1H, t, J 6.0Hz), 6.65(1H, dd, J 1.5, 3.5Hz), 7.21(1H, d, J 5.5Hz,) 7.39(1H, d, J 3.5Hz) 7.75(1H, dd, J 1.0, 2.0Hz), 7.92(1H, d, J 5.5Hz) and 9.31(1H, br s); Retention time 2.89 min(80:20) |
| 78 | 51 | mp 155-156° C.; NMR $\delta_H$(400MHz, $CDCl_3$) 3.86(3H, s), 3.87(3H, s), 4.68(2H, d, J 5.5Hz), 5.40(1H, t, J 5.5Hz), 6.62-6.64(1H, m), 6.82 (1H, d, J 8.0Hz), 6.94-6.99(2H, m), 7.24(1H, d, J 5.5Hz), 7.37(1H, dd, J 3.5, 1.0Hz), 7.72-7.73(1H, m), 7.86(1H, d, J 5.5Hz); Anal. Calcd for $C_{19}H_{17}N_3O_3S$: C, 62.11; H, 4.66, N, 11.43. Found: C, 62.19; H, 4.67; N, 11.44. |
| 79 | 92 | mp 169.6-169.9° C.; NMR $\delta_H$(400MHz, $CDCl_3$) 5.02(2H, s), 6.63-6.66 (1H, m), 7.22(1H, d, J 5.5Hz), 7.39(1H, dd, J 3.5, 1.0Hz), 7.22-7.74 (1H, m), 7.89(1H, d, J 5.5Hz); Anal. Calcd for $C_{10}H_7N_3OS$+0.2 $H_2O$: C, 54.38; H, 3.38, N, 19.03. Found: C, 54.69; H, 3.35; N, 18.74. |
| 80 | 45 | IR $v_{max}$(Nujol)/cm$^{-1}$ 2925, 2855, 1545, 1464, 1356; NMR $\delta_H$(400MHz, $CDCl_3$) 1.45(3H, t, J 7.5Hz), 2.61(3H, s), 3.15(2H, q, J 7.5Hz), 7.15 (1H, s), 7.50(1H, d, J 5.5Hz), 8.02(1H, d, J 5.5Hz). |
| 81 | 20 | NMR $\delta_H$(400MHz, $CDCl_3$) 8.08(1H, m), 7.80(1H, m), 7.55(2H, m), 6.70(1H, m), 4.90(2H, s) and 3.80(1H, br m); Retention time 3.06 (80:20). |
| 82 | 37 | IR $v_{max}$(Nujol)/cm$^{-1}$ 3050, 2925, 2855, 1543, 1526, 1460, 1356; NMR $\delta_H$ (400MHz, $CDCl_3$) 1.45(3H, t, J 7.5Hz), 3.18(2H, q, J 7.5Hz), 7.54 (1H, d, J 7.5Hz), 7.61(1H, d, J 3.1Hz), 8.09(1H, d, J 7.5Hz), 8.15 (1H, d, J 3.1Hz). |
| 83 | | IR $v_{max}$(Nujol)/cm$^{-1}$ 3287, 3089, 2924, 2854, 1633, 1603, 1548, 1516, 1486, 1462, 1377 and 1331; NMR $\delta_H$(400MHz, $CDCl_3$) 1.93(3H, s), 3.54(2H, q, J 5.5Hz), 3.69(2H, q, J 5.5Hz), 5.43(1H, t, J 6.0Hz), 6.65 (1H, dd, J 1.5, 3.5Hz), 6.76(1H, br s), 7.22(1H, d, J 5.5Hz), 7.39(1H, dd, J 1.0, 3.5Hz), 7.73(1H, dd, J 1.0, 1.5Hz) and 7.89(1H, d, J 5.5Hz); Retention time 3.08 min (70:30). |
| 84 | | IR $v_{max}$(Nujol)/cm$^{-1}$ 3317, 3265, 2924, 2854, 1635, 1613, 1580, 1558, 1514, 1463, 1377 and 1335; NMR $\delta_H$(400MHz, $CDCl_3$), 0.90(6H, d, J 5.5Hz), 2.01(2H, m), 2.07(1H, m), 3.56(2H, q, J 5.5Hz), 3.68(2H, q, J 5.5Hz), 5.49(1H, t, J 6.0Hz), 6.65(1H, dd, J 1.5, 3.5Hz), 7.21(1H, d, J 5.5Hz), 7.39(1H, dd, J 1.0, 3.5Hz), 7.73(1H, dd, J 1.0, 1.5Hz) and 7.89(1H, d, J 5.5Hz); Retention time 4.43 min (70:30). |
| 85 | | IR $v_{max}$(Nujol)/cm$^{-1}$ 3318, 3083, 2974, 2871, 1644, 1600 1549, 1488, 1461 and 1337; NMR $\delta_H$(400MHz, $CDCl_3$) 3.75(2H, q, J 5.5Hz), 3.83 (2H, q, J 5.5Hz), 5.68(1H, t, J 5.0Hz), 6.62(1H, dd, J 1.5, 3.5Hz), 7.21 (1H, d, J 5.5Hz), 7.29(2H, m), 7.38(1H, m), 7.71(3H, m), 7.87(1H, m) and 7.90(1H, d, J 5.5Hz); Retention time 5.05 min (70:30). |
| 86 | | IR $v_{max}$(Nujol)/cm$^{-1}$ 3267, 3108, 2925, 2854, 1641, 1611, 1548, 1517, 1485, 1464, 1422 and 1334; NMR $\delta_H$(400MHz, $CDCl_3$) 3.71(2H, q, J 5.5Hz), 3.81(2H, q, J 5.5Hz), 5.65(1H, t, J 6.0Hz), 6.63(1H, dd, J 1.5, |

TABLE 2-continued

Analytical data
HPLC is carried out using the following conditions: Column.
Supelcosil ABZ⁺ (170 × 4.6 mm),
particle size 5 μM, mobile phase MeOH: 10 mM aq
NH₄OAc (80:20), (70:30) or (60:40) (specified
in Table 2), flow rate 1.0 mL/min.,
detection wavelength λ = 230 nM
(unless otherwise stated), retention
times are provided in Table 2.

| Example | Yield(%) | Physical Data |
|---|---|---|
| | | 3.5Hz), 6.92(1H, m), 7.24(1H, d, J 5.5Hz), 7.37(3H, m), 7.56(1H, br s), 7.72(1H, dd, J 1.0, 1.5Hz) and 7.89(1H, d, J 5.5Hz); Retention time 4.79 min. (70:30). |
| 87 | | NMR $\delta_H$(400MHz, CDCl₃) 3.52(2H, m), 3.64(3H, s), 3.79(2H, m), 5.53(1H, br s), 6.73(1H, dd, J 1.5, 3.5Hz), 7.34(1H, d, J 5.5Hz), 7.65 (1H, m), 7.83(1H, m) and 8.02(1H, d, J 5.5Hz); Retention time 3.46 min. (70:30). |
| 88 | | NMR $\delta_H$(400MHz, CDCl₃) 0.87(6H, d, J 6.4Hz), 1.83(2H, m), 3.52 (2M, q, J 5.5Hz), 3.73(2H, m), 3.85(2H, m), 5.50(1H, br s) 6.71(1H, dd, J 1.5, 3.5Hz), 7.32(1H, d, J 5.5Hz), 7.61(1H, m), 7.81(1H, m) and 7.96(1H, d, J 5.5Hz); Retention time 5.69 min. (70:30). |
| 89 | 99 | NMR $\delta_H$(400MHz, CDCl₃) 3.55(2H, q, J 5.8Hz), 3.78(2H, q, J 5.8Hz,) 5.07(2H, s), 5.55(1H, m), 6.73(1H, dd, J 1.5, 3.5Hz), 7.29(5H, m), 7.40(1H, d, J 5.5Hz), 7.76(1H, m), 7.85(1H, m), 8.11(1H, d, J 5.5Hz) and 10.05(1H, br s); Retention time 6.16 min (70:30) |
| 90 | | NMR $\delta_H$(400MHz, CDCl₃) 3.01(1H, t, J 5.8Hz), 3.60(2H, q, J 5.5Hz), 4.04(2H, d, J 5.8Hz), 4.11(2H, q, J 5.5Hz), 5.46(1H, m), 6.61 (1H, dd, J 1.5, 3.5Hz), 7.31(1H, d, J 5.5Hz), 7.33-7.45(4H, m), 7.71-7.79 (4H, m) and 7.82(1H, d, J 5.5Hz); Retention time 17.2 min (70:30). |
| 91 | | NMR $\delta_H$(400MHz, DMSO) 3.27(2H, m), 3.42(2H, m), 3.63(2H, m), 5.01(1H, m), 5.08(1H, m), 5.77(1H, m), 6.10(1H, br s), 6.85(1H, dd, J 1.5, 3.5Hz), 7.29(1H, d, J 5.5Hz), 7.48(2H, m), 8.17(1H, m) and 8.35 (1H, d, J 5.5Hz); Retention time 3.39 min. (70:30). |
| 92 | 99 | NMR $\delta_H$(400MHz, DMSO) 3.30(2H, t, J 6.0Hz), 3.45(2H, t, J 6.0Hz), 4.23(2H, s), 6.46(1H, br s), 6.85(1H, dd, J 2.0, 3.5Hz), 7.18-7.33 (7H, m), 7.49(2H, m), 8.17(1H, m) and 8.36(1H, d, J 5.5Hz); Retention time 4.61 min (7:3) |
| 93 | | NMR $\delta_H$(400MHz, DMSO) 1.02-1.25(5H, m), 1.51-1.78(5H, m), 3.26(2H, m), 3.34(1H, m), 3.43(2H, m), 5.75(1H, br s), 6.78(1H, br s), 6.87(1H, dd, J 1.5, 3.5Hz), 7.34(1H, d, J 5.5Hz), 7.49(1H, m), 7.96 (1H, br s), 8.15(1H, m) and 8.36(1H, d, J 5.5Hz); Retention time 5.30 min, (70:30). |
| 94 | | NMR $\delta_H$(400MHz, DMSO) 3.35(2H, m), 3.44(2H, m), 6.30(1H, t, J 6.0Hz), 6.79(1H, dd, J 1.5, 3.5Hz), 7.17-7.31(5H, m), 7.36-7.47 (3H, m), 8.10(1H, m), 5.27(1H, d, J 5.5Hz) and 8.52(1H, m); Retention time 5.46 min, (70:30). |
| 95 | | NMR $\delta_H$(400MHz, DMSO) 3.35(2H, q, J 5.8Hz), 3.46(2H, q, J 5.8Hz), 6.35(1H, t, J 6.0Hz), 6.80(1H, dd, J 1.5, 3.5Hz), 7.19(1H, m), 7.25(3H, m), 7.41(3H, m), 8.10(1H, dd, J 1.0, 1.5Hz), 8.28(1H, d, J 5.5Hz) and 8.70(1H, m); Retention time 9.61 min. (70:30). |
| 96 | | NMR $\delta_H$(400MHz, CDCl₃) 3.56(2H, q, J 5.8Hz), 3.78(2H, m), 5.07 (2H, s), 5.55(1H, br s), 6.73(1H, dd, J 1.5, 3.5Hz), 7.29-7.36(5H, m), 7.39(1H, d, J 5.5Hz), 7.76(1H, m), 7.85(1H, m) 8.11(1H, d, J 5.5Hz) and 10.07(1H, br s); Retention time 6.16 min (70:30). |
| 97 | | NMR $\delta_H$(400MHz, DMSO) 3.58(2H, m), 3.76(2H, m), 6.80(1H, dd, J 1.5, 3.5Hz), 7.22(1H, d, J 5.5Hz), 7.35(4H, m), 7.42(3H, m), 7.96 (1H, m) 8.11(1H, m), 8.27(1H, d, J 5.5Hz) and 9.68(1H, br s); Retention time 8.41 min, (70:30). |
| 98 | | NMR $\delta_H$(400MHz, DMSO) 2.93(3H, s), 3.21(2H, m), 3.64(2H, m), 6.86(1H, dd, J 1.5, 3.5Hz), 7.18(1H, m), 7.32(1H, m), 7.52(1H, m), 7.86(1H, m), 8.17(1H, m) and 8.37(1H, m); Retention time 2.93 min (70:30). |
| 99 | | NMR $\delta_H$(400MHz, CDCl₃) 1.21(9H, s), 3.28(2H, q, J 5.8Hz), 3.61 (2H, q, J 5.9Hz), 5.41(1H, t, J 6.0Hz), 6.58(1H, t, J 6.0Hz) 6.65(1H, dd, J 1.5, 3.5Hz), 7.23(1H, d, J 5.5Hz), 7.40(3H, m), 7.69(2H, d, J 6.4Hz), 7.74(1H, m) and 7.87(1H, d, J 5.5Hz); Retention time 10.30 min |
| 100 | 35 | NMR $\delta_H$(400MHz, CDCl₃) 8.88(1H, m), 8.70(1H, m), 8.08(1H, m), 7.88(1H, m), 7.82(1H, m), 7.78(1H, m), 7.64(2H, m) and 6.30(1H, m); Retention time 3.52 (80:20). |
| 101 | 80 | mp 193.9-195.0° C.; IR $\nu_{max}$(Nujol)/cm⁻¹ 3246, 3149, 3080, 3064, 1683, 1664, 1599, 1547, 1497, 1315 and 1298; NMR $\delta_H$(400MHz, DMSO) 2.26(3H, s), 6.86-6.88(1H, m), 7.51(1H, d, J 3.0Hz), 7.48 (1H, d, J 5.5Hz), 8.20(1H, s), 8.51(1H, d, J 5.5Hz), 10.58(1H, s); Anal. Calcd for C₁₂H₉N₃O₂S+0.5 H₂O: C, 53.72; H, 3.76, N, 15.66. Found: C, 53.81; H, 3.44; N, 15.41. |

TABLE 2-continued

Analytical data
HPLC is carried out using the following conditions: Column.
Supelcosil ABZ+ (170 × 4.6 mm),
particle size 5 μM, mobile phase MeOH: 10 mM aq
NH$_4$OAc (80:20), (70:30) or (60:40) (specified
in Table 2), flow rate 1.0 mL/min.,
detection wavelength λ = 230 nM
(unless otherwise stated), retention
times are provided in Table 2.

| Example | Yield(%) | Physical Data |
|---|---|---|
| 102 |  | Mp 243-244° C., IR $\nu_{max}$(Nujol)/cm$^{-1}$ 2955, 2924, 2854, 1543, 1526, 1574, 1468, 1435, 1358 and 1236. NMR $\delta_H$(400MHz, CDCl$_3$) 8.18(1H, d, J 5.5Hz), 7.82(1H, s), 7.53(1H, d, J 5.5Hz), 2.63(3H, s). |
| 103 |  | Mp 240-241° C., IR $\nu_{max}$(Nujol)/cm$^{-1}$ 2955, 2925, 2854, 1537, 1516, 1481, 1460, 1359 and 1230. NMR $\delta_H$(400MHz, CDCl$_3$) 8.15(1H, d, J 5.5Hz), 7.51(1H, d, J 5.5Hz), 2.50(6H, s). |
| 104 | 71 | mp 208-211° C.; IR $\nu_{max}$(Nujol)/cm$^{-1}$ 2855, 1567, 1520, 1358, 1101, 817 and 794; NMR $\delta_H$(400MHz, CDCl$_3$) 2.57(3H, d, J 1.0Hz), 3.30(6H, s), 7.24(1H, d, J 5.5Hz), 7.74(1H, d, J 1.5Hz) and 7.89(1H, d, J 5.5Hz) |
| 105 | 99 | Mp 148-149° C.; IR $\nu_{max}$(Nujol)/cm$^{-1}$ 2854, 1564, 1356, 1236 and 7932; NMR $\delta_H$(400MHz, CDCl$_3$) 2.45(3H, s), 2.47(3H, s), 3.30(6H, s), 7.23 (1H, d, J 5.5Hz) and 7.87(1H, d, J 5.5Hz) |
| 106 |  | Mp 170-170.5° C.; IR $\nu_{max}$(Nujol)/cm$^{-1}$ 3061, 2955, 2925, 2854, 1545, 1519, 1480, 1465, and 1377. NMR $\delta_H$(400MHz, CDCl$_3$) 8.09(1H, d, J 5.5Hz), 7.88(2H, d, J 7.0Hz), 7.71(1H, s), 7.57(1H, d, J 5.5Hz), 7.50 (2H, t, J 7.5Hz), 7.42(1H, t, J 7.5Hz), 3.25(2H, q, J 7.5Hz), 1.53(3H, t, J 7.5Hz). |
| 107 |  | Mp 258-258.5° C.; IR $\nu_{max}$(Nujol)/cm$^{-1}$ 3136, 3073, 2955, 2924, 2854, 1573, 1559, 1514, 1475, 1408, 1335 and 1251. NMR $\delta_H$(400MHz, CDCl$_3$) 10.43(1H, br s), 7.91(1H, d, J 5.5Hz), 7.43(1H, s), 7.25-7.21 (2H, m), 3.30(6H, s) |
| 108 | 80 | Mp 178.7-179.5° C.; IR $\nu_{max}$(Nujol)/cm$^{-1}$ 3245, 2924, 2845, 1600, 1554, 1530, 1515, 1467, 1344, 1321, 1251 and 1232, NMR $\delta_H$(400MHz, CDCl$_3$) 8.11(1H, d, J 3.2Hz), 7.97(1H, m), 7.55(1H, d, J 3.2Hz), 7.25(1H, s), 7.00(1H, s), 6.98(1H, m), 6.84(1H, m), 5.46(1H, t, J 5.6Hz), 4.70(2H, d, J 6.0Hz), 3.87(3H, s) and 3.87(3H, s); Anal Calcd. for C$_{18}$H$_{16}$N$_4$O$_2$S$_2$: C, 56.23; H, 4.19; N, 14.57. Found: C, 56.23; H, 4.11; N 14.41. |
| 109 |  | Mp 221-222° C.; IR $\nu_{max}$(Nujol)/cm$^{-1}$ 3083, 2925, 2854, 1528, 1519, 1461, 1377, 1303, 1241 and 1161. NMR $\delta_H$(400MHz, CDCl$_3$) 8.68 (1H, s), 8.63(1H, d, J 8.0Hz), 8.17(1H, d, J 5.5Hz), 7.74(1H, d, J 8.0Hz), 7.52(1H, d, J 5.5Hz), 2.48(3H, s). |
| 110 | 63 | mp 190.1-190.7° C.; IR $\nu_{max}$(Nujol)/cm$^{-1}$ 3464, 3296, 3165, 3122, 3038, 1635, 1555, 1541, 1481 and 1360; NMR $\delta_H$(400MHz, CDCl$_3$) 5.10(2H, s), 7.24(1H, d, J 5.5Hz), 7.58(1H, d, J 3.0Hz), 7.98(1H, d, J 5.5Hz), 8.12(1H, d, J 3.0Hz); Anal. Calcd for C$_9$H$_6$N$_4$S$_2$: C, 46.14; H, 2.58, N, 23.90. Found: C, 46.14; H, 2.67; N, 23.02. |
| 111 | 85 | mp 139.3-139.7° C.; IR $\nu_{max}$(Nujol)/cm$^{-1}$ 3326, 3118, 3078, 3062, 1557, 1537, 1506, 1356 and 795; NMR $\delta_H$(400MHz, CDCl$_3$) 1.75-7.84 (1H, m), 1.91-2.10(2H, m), 2.15-2.26(1H, m), 3.70-3.82(2H, m), 3.84-3.98(2H, m), 4.38-4.56(1H, s), 7.24(1H, d, J 5.5Hz), 7.56 (1H, d, J 3.5Hz), 7.95(1H, d, J 5.5Hz), 8.12(1H, d, J 3.5Hz); Anal. Calcd for C$_{14}$H$_{14}$N$_4$OS$_2$: C, 52.81; H, 4.43, N, 17.59. Found: C, 53.08; H, 4.53; N, 17.22. |
| 112 | 62 | mp 128-129° C.; IR $\nu_{max}$(Nujol)/cm$^{-1}$ 3251, 3102, 3076, 3019, 1596, 1552, 1528, 1448, 1336 and 794; NMR $\delta_H$(400MHz, CDCl$_3$) 4.19-4.24 (2H, m), 5.14-5.37(3H, m), 5.99-6.10(1H, m), 7.24(1H, d, J 5.5Hz), 7.56(1H, d, J 3.0Hz), 7.95(1H, d, J 5.5Hz), 8.11(1H, d, J 3.0Hz). |
| 113 | 84 | mp 90.6-90.7° C.; IR $\nu_{max}$(Nujol)/cm$^{-1}$ 3056, 2961, 2855, 1546, 1529, 1480, 806; NMR $\delta_H$(400MHz, CDCl$_3$) 1.48(6H, d, J 6.9Hz), 3.40(1H, heptet, J 6.9Hz), 7.55(1H, d, J 5.5Hz), 7.59(1H, d, J 3.1Hz), 8.08(1H, d, J 5.5Hz), 8.14(1H, d, J 3.1Hz). |
| 114 | 7 | IR $\nu_{max}$(Nujol)/cm$^{-1}$ 2925, 2854, 1615, 1545, 1498, 1459, 1377, 1265 and 1174; NMR $\delta_H$(400MHz, CDCl$_3$) 8.05(1H, m), 7.80(1H, m), 7.60 (2H, m), 7.00(1H, m), 3.83(3H, s), 3.25(2H, q, J 7.0Hz) and 1.50(3H, t, J 7.0Hz). |
| 115 | 93 | mp 133-133.5° C.; IR $\nu_{max}$(Nujol)/cm$^{-1}$ 2925, 1553, 1467, 1404, 1356, 1241 and 796; NMR $\delta_H$(400MHz, CDCl$_3$) 2.44(3H, s), 3.35(6H, s), 7.25(1H, d, J 5.5Hz), 7.67(1H, dd, J 7.5, 2.5Hz), 7.89(1H, d, J 5.5Hz), 8.54(1H, d, J 8.5Hz) and 8.64(1H, d J 2.0Hz) |
| 116 | 37 | mp 242.6-243.9° C.; IR $\nu_{max}$(Nujol)/cm$^{-1}$ 3251, 3079, 3060, 1687, 1672, 1560, 1496 and 1320; NMR $\delta_H$(400MHz, DMSO) 2.29(3H, s), 7.54(1H, d, J 5.5Hz), 8.15(1H, d, J 3.5Hz), 8.27(1H, d, J 3.0Hz), 8.56 (1H, d, J 5.5Hz), 10.68(1H, s). |

TABLE 2-continued

Analytical data
HPLC is carried out using the following conditions: Column.
Supelcosil ABZ+ (170 × 4.6 mm),
particle size 5 μM, mobile phase MeOH: 10 mM aq
NH$_4$OAc (80:20), (70:30) or (60:40) (specified
in Table 2), flow rate 1.0 mL/min.,
detection wavelength λ = 230 nM
(unless otherwise stated), retention
times are provided in Table 2.

| Example | Yield(%) | Physical Data |
|---|---|---|
| 117 | 67 | Mp 149° C.; IR $\nu_{max}$(Nujol)/cm$^{-1}$ 2955, 2925, 2854, 1595, 1523, 1485, 1468 and 1333; NMR $\delta_H$(400MHz, CDCl$_3$) 8.00(1H, m), 7.76(1H, m), 7.60(1H, m), 7.56(1H, m), 7.36(1H, m), 7.05(1H, m), 6.92(1H, m), 6.63(1H, m) and 4.59(2H, s). |
| 118 | | IR $\nu_{max}$(Nujol)/cm$^{-1}$ 3036, 2925, 2854, 1535, 1481, 1468, 1351, 1129 and 1098; NMR $\delta_H$(400MHz, CDCl$_3$) 9.01(1H, m), 8.78(1H, s), 8.01(1H, d, J 5.6Hz), 7.57(1H, d, J 5.2Hz), 3.13(2H, q, J 7.6Hz) and 1.47(3H, t, J 7.6Hz). |
| 119 | 3 | Mp 179° C.; IR $\nu_{max}$(Nujol)/cm$^{-1}$ 3057, 2924, 2854, 1525, 1465, 1438, 1378 and 1296; NMR $\delta_H$(400MHz, CDCl$_3$) 8.12(2H, m), 7.58(2H, m), 3.30(4H, q, J 7.0Hz) and 1.60(6H, t, J 7.0Hz); M/Z 327(M+H)$^+$. |
| 120 | | IR $\nu_{max}$(Nujol)/cm$^{-1}$ 3388, 3060, 2924, 2855, 1662, 1561, 1541, 1461, 1376, 1356, 1309, 1266 and 1096. NMR $\delta_H$(400MHz, CDCl$_3$) 8.32(1H, br s), 8.13(1H, d, J 5.5Hz), 7.58(1H, J 5.5Hz), 7.26(1H, s), 3.19(2H, q, J 7.5Hz), 1.48(3H, t, 7.5Hz). |
| 121 | 39 | mp 178.6-179.6° C.; IR $\nu_{max}$(Nujol)/cm$^{-1}$ 3080, 2925, 1569, 1525, 1468, 1092, 854, 815 and 750; NMR $\delta_H$(400MHz, CDCl$_3$) 1.47(3H, t, J 7.5Hz), 3.11(2H, q, J 7.5Hz), 7.29(1H, s), 7.47(1H, s), 7.51(1H, d, J, 5.5Hz), 8.07(1H, d, J 5.5Hz) and 10.65(1H, br s) |
| 122 | 13 | Mp 131° C.; IR $\nu_{max}$(Nujol)/cm$^{-1}$ 2960, 1547, 1529, 1377, 1314, 1301 and 1096; NMR $\delta_H$(400MHz, CDCl$_3$) 8.24(1H, m), 8.12(1H, m), 8.02 (1H, m), 7.48-7.60(3H, m), 3.20(2H, q, J 7.0Hz) and 1.50(3H, t, J 7.0Hz). |
| 123 | 73 | IR $\nu_{max}$(Nujol)/cm$^{-1}$ 3392, 3254, 1681, 1586, 1552, 1515, 1342, 1318, 1274, 1252, 1165 and 1150; NMR $\delta_H$(400MHz, CDCl$_3$) 1.43(9H, s), 3.46(2H, q, J 5.5Hz), 3.70(2H, q, J 5.5Hz), 5.12(1H, br s), 5.42(1H, t, J 5.5Hz), 7.23(1H, d, J 5.5Hz), 7.55(1H, d, J 3.5Hz), 7.95(1H, d, J 5.5Hz) and 8.11(1H, d, J 3.0Hz); Retention time 5.17 min (70:30) |
| 124 | 60 | IR $\nu_{max}$(Nujol)/cm$^{-1}$ 3352, 3241, 3045, 1558, 1349, 1315, 1280 and 1116; NMR $\delta_H$(400MHz, CDCl$_3$) 1.27(2H, br s), 3.02(2H, t, J 6.0Hz), 3.63(2H, q, J 6.0Hz), 5.46(1H, m), 7.23(1H, d, J 5.5Hz), 7.55(1H, d, J 3.5Hz), 7.94(1H, d, J 5.5Hz) and 8.11(1H, d, J 3.5Hz); Retention time 2.35 min (60:40) |
| 125 | 61 | NMR $\delta_H$(400MHz, DMSO) 1.81(3H, s), 3.30(2H, q, J 6.0Hz), 3.44 (2H, q, J 6.0Hz), 7.28(2H, m), 7.97(1H, m), 8.07(1H, d, J 3.0Hz), 8.21(1H, d, J 3.0Hz) and 8.32(1H, d, J 5.5Hz); Retention time 2.83 min (70:30) |
| 126 | | NMR $\delta_H$(400MHz, DMSO) 0.97(3H, t, J 7.2Hz), 3.00(2H, m), 3.26 (2H, q, J 6.0Hz), 3.40(2H, q, J 6.0Hz), 5.86(1H, t, J 5.5Hz), 5.96(1H, t, J 5.5Hz), 7.29(2H, m), 8.08(1H, d, J 3.2Hz), 8.22(1H, d, J 3.3Hz) and 8.32(1H, d, J 5.5Hz); Retention time 2.42 (80:20). |
| 127 | | NMR $\delta_H$(400MHz, DMSO) 3.30(2H, q, J 5.8Hz), 3.42(2H, q, J 5.8Hz), 3.63(2H, m), 5.00(1H, dd, J 1.6, 10.2Hz), 5.09(1H, dd, J 1.8, 17.2Hz), 5.79(1H, m), 6.05(2H, m), 7.29(2H, m) 8.08(1H, d, J 3.1Hz), 8.22(1H, d, J 3.1Hz) and 8.32(1H, d, J 5.5Hz); Retention time 2.50 min (80:20). |
| 128 | 81 | NMR $\delta_H$(400MHz, DMSO) 0.99-1.28(5H, m), 1.48-1.74(5H, m), 3.25(2H, q, J 6.0Hz), 3.33(1H, m), 3.39(2H, q, J 6.0Hz), 5.77(1H, d, J 8.0Hz), 5.86(1H, t, J 5.5Hz), 7.28(1H, m), 8.07(1H, d, J 3.0Hz), 8.21(1H, d, J 3.0Hz) and 8.31(1H, d, J 5.5Hz); Retention time 3.11 min (80:20) |
| 129 | 42 | NMR $\delta_H$(400MHz, DMSO) 0.84(6H, d, J 6.5Hz), 1.95(3H, m), 3.37 (2H, m), 3.43(2H, q, J 6.0Hz), 7.26(2H, m), 7.89(1H, m), 8.08(1H, d, J 3.0Hz), 8.21(1H, d, J 3.0Hz) and 8.32(1H, d, J 5.5Hz); Retention time 2.77 min (80:20) |
| 130 | 58 | NMR $\delta_H$(400MHz, DMSO) 3.25(2H, q, J 6.0Hz), 3.44(2H, q, J 6.0Hz), 3.52(3H, s), 7.21(1H, t, J 5.5Hz), 7.26(1H, d, J 5.5Hz), 7.30(1H, m), 8.07(1H, d, J 3.0Hz), 8.21(1H, d, J 3.0Hz) and 8.32(1H, d, J 5.5 Hz); Retention time 2.53 min (80:20) |
| 131 | 62 | NMR $\delta_H$(400MHz, DMSO) 0.84(6H, d, J 6.5Hz), 1.79(1H, m), 3.25 (2H, q, J 6.0Hz), 3.45(2H, q, J 6.0Hz), 3.71(2H, d, J 6.5Hz), 7.16 (1H, t, J 5.5Hz), 7.26(1H, d, J 5.5Hz), 7.30(1H, m), 8.07(1H, d, J 3.0Hz), 8.21(1H, d, J 3.0Hz) and 8.32(1H, d, J 5.5Hz); Retention time 3.23 min (80:20) |
| 132 | | NMR $\delta_H$(400MHz, DMSO) 1.21(9H, s), 3.24(2H, q, J 5.8Hz), 3.39 (2H, q, J 5.8Hz), 5.68(1H, s), 5.80(1H, t, J 6.0Hz), 7.28(2H, m), 8.07 (1H, d, J 3.1Hz), 8.22(1H, d, J 3.1Hz), and 8.32(1H, d, J 5.5Hz); Retention time 2.83 min, (80:20). |

TABLE 2-continued

Analytical data
HPLC is carried out using the following conditions: Column.
Supelcosil ABZ+ (170 × 4.6 mm),
particle size 5 μM, mobile phase MeOH: 10 mM aq
NH$_4$OAc (80:20), (70:30) or (60:40) (specified
in Table 2), flow rate 1.0 mL/min.,
detection wavelength λ = 230 nM
(unless otherwise stated), retention
times are provided in Table 2.

| Example | Yield(%) | Physical Data |
|---|---|---|
| 133 | 95 | NMR δ$_H$(400MHz, DMSO) 3.30(2H, q, J 6.0Hz), 3.42(2H, q, J 6.0Hz), 4.20(2H, d, J 5.6Hz), 6.10(1H, t, J 5.9Hz), 6.41(1H, t, J 6.0Hz), 7.16-7.33(7H, m), 8.07(1H, d, J 3.5Hz), 8.21(1H, d, J 3.0Hz) and 8.31(1H, d, J 5.5Hz); Retention time 2.87 min (80:20) |
| 134 |  | NMR δ$_H$(400MHz, DMSO) 3.38(2H, q, J 5.8Hz), 3.47(2H, q, J 5.8Hz), 6.29(1H, t, J 6.0Hz), 6.88(1H, t, J 6.0Hz), 7.21(1H, t, J 6.0Hz), 7.27(3H, m), 7.37(3H, m), 8.07(1H, d, J 3.1Hz), 8.22(1H, d, J 3.2Hz) and 8.32(1H, d, J 5.5Hz); Retention time 3.22 min (80:20). |
| 135 |  | NMR δ$_H$(400MHz, DMSO) 3.38(2H, q, J 5.8Hz), 3.48(2H, q, J 5.8Hz), 6.33(1H, t, J 6.0Hz), 7.27(3H, m), 7.40(3H, m), 8.06(1H, d, J 3.1Hz), 8.21(1H, d, J 3.1Hz), 8.32(1H, d, J 5.5Hz) and 8.67(1H, s); Retention time 4.32 min (80:20). |
| 136 |  | NMR δ$_H$(400MHz, DMSO) 1.08-1.32(6H, m), 1.51-1.85(4H, m), 3.53(2H, m), 3.62(3H, m), 7.29(2H, m), 7.36(1H, m), 8.08(1H, d, J 3.1Hz), 8.22(1H, d, J 3.1Hz) and 8.31(1H, d, J 5.5Hz); Retention time 3.58 min. (80:20). |
| 137 |  | NMR δ$_H$(400MHz, DMSO) 3.60(2H, m), 3.79(2H, m), 7.07(1H, t, J 6.0Hz), 7.26(3H, m), 7.36(2H, m), 7.42(1H, m), 7.83(1H, br s), 8.07 (1H, d, J 3.2Hz), 8.22(1H, d, J 3.2Hz), 8.32(1H, d, J 5.5Hz) and 9.58 (1H, br s); Retention time 2.98 min (80:20). |
| 138 | 99 | NMR δ$_H$(400MHz, DMSO) 3.59(2H, q, J 6.0Hz), 3.78(2H, m), 7.25 (1H, d, J 5.5Hz), 7.29(2H, d, J 9.1Hz), 7.41(1H, m), 7.42(2H, d, J 9.0Hz), 7.95(1H, m), 8.07(1H, d, J 3.5Hz), 8.21(1H, d, J 3.0Hz), 8.32 (1H, d, J 5.5Hz) and 9.63(1H, br s); Retention time 3.98 min (80:20) |
| 139 | 93 | IR ν$_{max}$(Nujol)/cm$^{-1}$ 3063, 2926, 2855, 1547, 1530, 1466; NMR δ$_H$(400MHz, CDCl$_3$) 1.55(9H, s), 7.56(1H, d, J 7.5Hz), 7.58(1H, d, J 3.1Hz), 8.60(1H, d, J 7.5Hz), 8.18(1H, d, J 3.1Hz). |
| 140 | 13 | IR ν$_{max}$(Nujol)/cm$^{-1}$ 3061, 2924, 1550, 1531, 1480; NMR δ$_H$(400MHz, CDCl$_3$) 1.10(2H, m), 1.24(2H, m), 2.39(1H, m), 7.42(1H, d, J 7.5Hz), 7.58(1H, d, J 3.1Hz), 8.00(1H, d, J 7.5Hz), 8.10(1H, d, J 3.1Hz). |
| 141 | 65 | mp 74.7-74.9° C.; IR ν$_{max}$(Nujol)/cm$^{-1}$ 2925, 1531, 1455, 1350, 1078, and 799; NMR δ$_H$(400MHz, CDCl$_3$) 1.52(3H, t, J 7.5Hz), 2.74(3H, s), 3.19(2H, q, J 7.5Hz), 7.29(1H, d, J 7.5Hz), 7.52(1H, d, J 6.0Hz), 7.80 (1H, t, J 8.0Hz), 8.06(1H, d, J 5.5Hz) and 8.58(1H, d, J 8.0Hz) |
| 142 |  | NMR δ$_H$(400MHz, DMSO) 8.32(1H, m), 8.22(1H, m), 8.08(1H, m), 7.79(1H, m), 7.34-7.26(2H, m), 3.45-3.29(4H, m), 2.19(1H, m) and 1.81-1.15(10H, m); Retention time 3.26 min, (80:20). |
| 143 |  | NMR δ$_H$(400MHz, DMSO) 8.59(1H, br s), 8.33(1H, m), 8.22(1H, m), 8.08(1H, m), 7.94(1H, m), 7.85(2H, m), 7.63(1H, m), 7.52-7.43(1H, m), 7.28(1H, m) and 3.60-3.37(4H, br m); Retention time 3.03 min, (80:20). |
| 144 |  | NMR δ$_H$(400MHz, DMSO) 8.66(1H, br s), 8.33(1H, m), 8.22(1H, m), 8.08(1H, m), 7.88(2H, m), 7.52(2H, m), 7.45(1H, br s), 7.27(1H, m), 3.59-3.54(2H, br m) and 3.30-3.20(2H, m); Retention time 3.95 min, (80:20). |
| 145 | 70 | NMR δ$_H$(400MHz, DMSO) 3.36(2H, q, J 6.0Hz), 3.46(2H, q, J 6.0Hz), 7.12(1H, dd, J 4.0, 5.0Hz), 7.26(1H, d, J 5.5Hz), 7.72(1H, m), 7.88(1H, d, J 5.0Hz), 8.07(1H, d, J 3.0Hz), 8.21(1H, d, J 3.5Hz), 8.32 (1H, d, J 5.5Hz) and 8.60(1H, m); Retention time 2.98 min (80:20) |
| 146 | 45 | NMR δ$_H$(400MHz, DMSO) 3.34(2H, q, J 6.0Hz), 3.53(2H, q, J 6.0Hz), 7.22-7.40(8H, m), 8.08(1H, d, J 3.0Hz), 8.22(1H, d, J 3.0Hz) and 8.33(1H, d, J 5.5Hz); Retention time 3.08 min (80:20) |
| 147 | 62 | NMR δ$_H$(400MHz, DMSO) 3.28(2H, q, J 6.0Hz), 3.46(2H, q, J 6.0Hz), 5.01(2H, s), 7.22-7.38(8H, m), 8.07(1H, d, J 3.0Hz), 8.21(1H, d, J 3.5Hz) and 8.32(1H, d, J 5.5Hz); Retention time 3.39 min (80:20) |
| 148 | 29 | NMR δ$_H$(400MHz, DMSO) 2.92(3H, s), 3.22(2H, q, J 6.0Hz), 3.51 (2H, q, J 6.0Hz), 7.14(1H, t, J 5.9Hz), 7.31(1H, d, J 5.5Hz), 7.35(1H, m), 8.08(1H, d, J 3.5Hz), 8.22(1H, d, J 3.5Hz) and 8.34(1H, d, J 5.5Hz); Retention time 2.36 min (80:20) |
| 149 | 70 | NMR δ$_H$(400MHz, DMSO) 0.83(3H, t, J 7.5Hz), 1.32(2H, m), 1.60 (2H, m), 2.99(2H, m), 3.20(2H, q, J 6.0Hz), 3.49(2H, q, J 6.0Hz), 7.15(1H, t, J 5.9Hz), 7.26(1H, d, J 5.6Hz), 7.32(1H, m), 8.08(1H, d, J 3.0Hz), 8.22(1H, d, J 3.0Hz) and 8.33(1H, d, J 5.5Hz); Retention time 2.82 min (80:20) |

TABLE 2-continued

Analytical data
HPLC is carried out using the following conditions: Column.
Supelcosil ABZ+ (170 × 4.6 mm),
particle size 5 μM, mobile phase MeOH: 10 mM aq
NH₄OAc (80:20), (70:30) or (60:40) (specified
in Table 2), flow rate 1.0 mL/min.,
detection wavelength λ = 230 nM
(unless otherwise stated), retention
times are provided in Table 2.

| Example | Yield(%) | Physical Data |
|---|---|---|
| 150 | 22 | NMR $\delta_H$(400MHz, CDCl₃) 1.34(3H, d, J 6.5Hz), 3.71(1H, dd, J 6.7, 10.7Hz), 3.85(1H, dd, J 3.0, 11.0Hz), 4.29(1H, m), 5.20(1H, d, J 6.5Hz), 7.22(1H, d, J 5.5Hz), 7.56(1H, d, J 3.5Hz), 7.95(1H, d, J 5.5Hz) and 8.11(1H, d, J 3.0Hz); Retention time 2.67 min (80:20) |
| 151 | 33 | NMR $\delta_H$(400MHz, CDCl₃) 2.21(2H, quintet, J 6.7Hz), 3.59(2H, q, J 6.5Hz), 4.12(2H, t, J 7.0Hz), 5.20(1H, t, J 6.0Hz), 6.98(1H, m), 7.09 (1H, m), 7.24(1H, d, J 5.5Hz), 7.55(1H, m), 7.56(1H, d, J 3.0Hz), 7.97(1H, d, J 5.5Hz) and 8.12(1H, d, J 3.0Hz); Retention time 2.65 min (80:20) |
| 152 | 64 | NMR $\delta_H$(400MHz, CDCl₃) 1.80(1H, m), 1.97(1H, m), 2.03(1H, m), 2.20(1H, m), 3.71-3.80(2H, m), 3.85-3.97(2H, m), 4.41(1H, m), 7.23(1H, d, J 5.5Hz), 7.57(1H, d, J 3.0Hz), 7.94(1H, d, J 5.5Hz) and 8.12(1H, d, J 3.0Hz); Retention time 3.63 min (80:20) |
| 153 | 23 | Mp 221.9° C.; IR $\nu_{max}$(Nujol)/cm⁻¹ 3069, 2923, 2854, 1539, 1523, 1465, 1377, 1366 and 1319; NMR $\delta_H$(400MHz, CDCl₃) 8.16(2H, m), 8.10 (1H, m), 7.64(1H, m), 7.58(1H, m), 7.50(1H, m) and 7.20(1H, m). |
| 154 | 50 | IR $\nu_{max}$(Nujol)/cm⁻¹ 3074, 2924, 1546, 1529, 1473 and 1350; NMR $\delta_H$ (400MHz, CDCl₃) 3.60(2H, m), 4.15(2H, m), 7.42(1H, d, J 7.5Hz), 7.58(1H, d, J 3.1Hz), 8.1(1H, d, J 7.5Hz), 8.15(1H, d, J 3.1Hz). |
| 155 | 67 | mp 300° C. dec; IR $\nu_{max}$(Nujol)/cm⁻¹ 3472, 3051, 2925, 2853, 1707, 1598, 1525, 1466, 791, 742, 506; NMR $\delta_H$(400MHz, DMSO) 6.91(1H, dd J 1.7, 3.6Hz), 7.75(1H, d, J 5.5Hz), 7.82(1H, br), 7.89(1H, dd, J 0.8, 3.6Hz), 8.23(1H, dd, J 0.8, 1.7Hz), 8.40(1H, br), 8.64(1H, d, J 5.5Hz). |
| 156 | | Mp 117.7-118.2° C.; IR $\nu_{max}$(Nujol)/cm⁻¹ 3062, 2924, 2854, 1545, 1528, 1517, 1465, 1378, 1239 and 1134; NMR $\delta_H$(400MHz, CDCl₃) 8.39(1H, m), 8.08(1H, d, J 5.5Hz), 7.98(1H, dd, J 5.1, 1.1Hz), 7.55(1H, d, J 5.5Hz) and 7.52(1H, dd, J 5.1, 2.8Hz); Anal Calcd for C₁₀H₅ClN₂S₂0.5 H₂O: C45.89; H, 2.31; N, 10.70. Found C, 45.48; H, 2.18; N, 10.53. |
| 157 | 84 | Mp 119.0-119.4° C.; IR $\nu_{max}$(Nujol)/cm⁻¹ 2924, 2854, 1557, 1524, 1468, 1388, 1334, 1279, 1234 and 1092; NMR $\delta_H$(400MHz, CDCl₃) 8.23(1H, dd, J 2.9, 1.3Hz), 7.95(1H, dd, J 5.0, 1.0Hz), 7.45(1H, dd, J 5.1, 3.0Hz), 7.27(1H, m) and 3.31(6H, s). Anal Calcd for C₁₂H₁₁N₃S₂: C, 55.15; H, 4.24; N, 16.07. Found: C55.36; H, 4.22; N, 16.05 |
| 158 | 28 | Mp 146.5-147.2° C.; IR $\nu_{max}$(Nujol)/cm⁻¹ 3054, 2925, 2854, 1537, 1516, 1495, 1467, 1365, 1244 and 1138; NMR $\delta_H$(400MHz, CDCl₃) 8.20(2H, m), 8.11(1H, d, J 5.6Hz), and 7.62-7.57(4H, m); Anal Calcd for C₁₂H₇ClN₂S 0.25 H₂O; C, 57.37; H, 3.01; N, 11.15. Found: C, 57.25; H, 2.84; N, 11.40. |
| 159 | 97 | Mp 112.9-114.1° C.; IR $\nu_{max}$(Nujol)/cm⁻¹ 2924, 2854, 1585, 1556, 1523, 1468, 1409, 1355 and 1241, NMR $\delta_H$(400MHz, CDCl₃) 8.18(2H, m), 7.80(1H, d, J 5.5Hz), 7.56-7.51(3H, m), 7.29(1H, d, J 5.5Hz) and 3.33(6H, s). Anal. Calcd for C₁₄H₁₃N₃S 0.1 H₂O: C, 65.39; H, 5.13; N, 16.45; Found: C, 65.18; H, 5.14; N, 16.16. |
| 160 | 33 | Mp 129.3-129.9° C.; IR $\nu_{max}$(Nujol)/cm⁻¹ 3117, 2955, 2924, 2854, 1576, 1542, 1527, 1512, 1472, 1382, 1264, 1243, 1226, 1184 and 1155, NMR $\delta_H$(400MHz, CDCl₃) 8.40(1H, s), 8.05(1H, d, J 5.5Hz), 7.62 (1H, m), 7.54(1H, d, J 5.5Hz), and 7.22(1H, m); Anal. Calcd for C₁₀H₅ClN₂OS: C, 50.75; H, 2.13; N, 11.83. Found: C, 50.71; H, 2.13; N, 11.72. |
| 161 | 50 | Mp 98.4-99.0° C.; IR $\nu_{max}$(Nujol)/cm⁻¹ 2924, 2854, 1562, 1540, 1527, 1463, 1404, 1381, 1348 and 1229, NMR $\delta_H$(400MHz, CDCl₃) 8.27(1H, d, J 1.2Hz), 7.76(1H, d, J 5.4Hz), 7.55(1H, m), 7.26(1H, m), 7.17 (1H, d, J 1.2Hz), and 3.28(6H, s); Anal Calcd. for C₁₂H₁₁N₃OS 0.1 H₂O: C, 58.33; H, 4.57; N, 17.01. Found: C, 58.59; H, 4.56; N, 16.69. |
| 162 | 31 | Mp 204.0-204.9° C.; IR $\nu_{max}$(Nujol)/cm⁻¹ 2926, 2854, 1590, 1526, 1494, 1465, 1377, 1335 and 1268, NMR $\delta_H$(400MHz, DMSO) 8.71 (1H, s), 8.33(1H, d, J 1.2Hz), 7.76(1H, d, J 4.1Hz), and 6.95(1H, dd, J 3.8, 1.8Hz): Anal Calcd for C₁₀H₄ClN₃O₃S 0.1 H₂O: C, 42.37; H, 1.49; N, 14.82. Found: C, 42.01; H, 1.42; N, 14.75. |
| 163 | 69 | IR $\nu_{max}$(Nujol)/cm⁻¹ 2924, 2854, 1585, 1547, 1529, 1463, 1377 and 1154; NMR $\delta_H$(400MHz, CDCl₃) 8.39(1H, m), 7.95(1H, m), 7.62(1H, m), 7.53(1H, m), 7.24(1H, m), 3.10(2H, d, J 7.0Hz) and 1.42(3H, t, J 7.0Hz); M/Z 231(M+H)+. |
| 164 | 41 | IR $\nu_{max}$(Nujol)/cm⁻¹ 2925, 2854, 1615, 1546, 1526, 1482, 1463, 1420 and 1376; NMR $\delta_H$(400MHz, CDCl₃) 8.00(1H, m), 7.58(1H, m), 3.18 (2H, m), 2.50(3H, s), 2.39(3H, s) and 1.43(3H, m); M/Z 260(M+H)+. |

TABLE 2-continued

Analytical data
HPLC is carried out using the following conditions: Column. Supelcosil ABZ+ (170 × 4.6 mm), particle size 5 μM, mobile phase MeOH: 10 mM aq NH$_4$OAc (80:20), (70:30) or (60:40) (specified in Table 2), flow rate 1.0 mL/min., detection wavelength λ = 230 nM (unless otherwise stated), retention times are provided in Table 2.

| Example | Yield(%) | Physical Data |
|---|---|---|
| 165 | | IR ν$_{max}$(Nujol)/cm$^{-1}$ 3093, 2955, 2924, 2854, 1589, 1572, 1538, 1522, 1467 and 1253. NMR δ$_H$(400MHz, CDCl$_3$) 9.45(1H, d, J 2.0Hz), 8.85 (1H, m), 8.54-8.51(1H, m), 8.18(1H, d, J 5.5Hz), 7.62(1H, d, J 5.5Hz), 7.56-7.53(1H, m). |
| 166 | | IR ν$_{max}$(Nujol)/cm$^{-1}$ 3056, 2925, 2854, 1580, 1557, 1524, 1467, 1361 and 1249. NMR δ$_H$(400MHz, CDCl$_3$) 9.43(1H, d, J 1.8Hz), 8.76(1H, dd, J 4.7, 1.5Hz), 8.48-8.45(1H, m), 7.83(1H, d, J 5.5Hz), 7.53-7.46 (1H, m), 7.32(1H, d, J 5.5Hz), 3.32(6H, s). |
| 167 | | NMR δ$_H$(400MHz, CDCl$_3$) 8.12(1H, d, J 5.5Hz), 7.49(1H, d, J 5.5Hz), 7.38(1H, s), 7.16(1H, s), 7.30(3H, s). |
| 168 | | NMR δ$_H$(400MHz, CDCl$_3$) 7.86(1H, d, J 5.5Hz), 7.31(1H, s), 7.24 (1H, d, J 5.5Hz), 7.06(1H, s), 4.28(3H, s), 3.29(6H, s). |
| 169 | | IR ν$_{max}$(Nujol)/cm$^{-1}$ 3332, 3072, 2924, 2854, 1606, 1547, 1516, 1489, 1464, 1409, 1387 and 1261; NMR δ$_H$(400MHz, CDCl$_3$) 7.87 1H, d, J 5.5Hz), 7.64 (1H, d, J 1.5Hz), 7.23(1H, d, J 5.5Hz), 6.57(1H, d, J 1.5Hz), 5.79(1H, t, J 7.0Hz), 4.83(2H, d, J 7.0Hz), 3.28(6H, s). |
| 170 | | IR ν$_{max}$(Nujol)/cm$^{-1}$ 3443, 3218, 3122, 2954, 2925, 2854, 1560, 1532, 1513, 1484, 1457, 1389 and 1318; NMR δ$_H$(400MHz, CDCl$_3$) 7.90(1H, dd, J 5.5, 1.8Hz), 7.30(1H, s), 7.20(1H, dd, J 5.5, 1.8Hz), 7.06(1H, s), 5.46(1H, br s), 4.22(3H, s), 3.91-3.90(2H, m), 3.72-3.68(3H, m). |
| 171 | | IR ν$_{max}$(Nujol)/cm$^{-1}$ 3267, 3124, 2924, 2854, 1609, 1547, 1514, 1487, 1459, 1378; NMR δ$_H$(400MHz, CDCl$_3$) 7.91(1H, d, J 5.5Hz), 7.65 (1H, s), 7.21(1H, d, J 5.5Hz), 6.56(1H, s), 6.20(1H, br s), 5.50(1H, br s), 4.79(2H, s), 3.90-3.88(2H, m), 3.70-3.66(2H, m), 1.61(1H, br s). |
| 172 | | IR ν$_{max}$(Nujol)/cm$^{-1}$ 2925, 2854, 1546, 1528, 1517, 1465, 1377 and 1222; NMR δ$_H$(400MHz, CDCl$_3$) 8.12(1H, d, J 5.5Hz), 7.50(1H, d, J 5.5Hz), 7.38(1H, s), 7.20(1H, s), 4.80(2H, q, J 7.0Hz), 1.55(3H, t, J 7.0Hz). |
| 173 | | IR ν$_{max}$(Nujol)/cm$^{-1}$ 3041, 2926, 2855, 1563, 1528, 1511, 1478, 1460, 1392 and 1377; NMR δ$_H$(400MHz, CDCl$_3$) 7.86(1H, d, J 5.5Hz), 7.32 (1H, s), 7.23(1H, d, J 5.5Hz), 7.11(1H, s), 4.83(1H, q, J 7.0Hz), 3.28 (6H, s), 1.52(3H, t, J 7.0Hz), |
| 174 | | IR ν$_{max}$(Nujol)/cm$^{-1}$ 3458, 3334, 2925, 2855, 1560, 1516, 1480, 1466, 1427 and 1334; NMR δ$_H$(400MHz, CDCl$_3$) 7.90(1H, d, J 5.5Hz), 7.32 (1H, s), 7.19(1H, d, J 5.5Hz), 7.11(1H, s), 5.45(1H, br t, J 5.5Hz), 4.74(2H, q, J 7.0Hz), 3.91-3.89(2H, m), 3.71-3.67(2H, m), 1.52 (3H, t, J 7.0Hz). |
| 175 | | IR ν$_{max}$(Nujol)/cm$^{-1}$ 3069, 2954, 2925, 2854, 1548, 1531, 1517, 1467, 1408, 1249 and 1225; NMR δ$_H$(400MHz, CDCl$_3$) 8.19(1H, d, J 5.5Hz), 7.54(1H, d, J 5.5Hz), 7.47-7.41(2H, m), 6.22(2H, s), 3.76(2H, t, J 8.5Hz), 1.02(2H, t, J 8.5Hz). |
| 176 | | Mp 131-132° C.; IR ν$_{max}$(Nujol)/cm$^{-1}$ 2924, 2854, 1560, 1533, 1512, 1480, 1465, 1419, 1389, 1250 and 1089; NMR δ$_H$(400MHz, CDCl$_3$) 7.95(1H, d, J 5.5Hz), 7.43(1H, d, J 1.5Hz), 7.38(1H, d, J 1.5Hz), 7.30 (1H, d, J 5.5Hz), 6.28(2H, s), 3.66(2H, t, 8.0Hz), 3.36(6H, s), 0.97 (3H, t, J 8.0Hz). |
| 177 | | Mp 209-210° C.; IR ν$_{max}$(Nujol)/cm$^{-1}$ 2925, 2854, 1749, 1559, 1530, 1508, 1476, 1388, 1376, 1241 and 1214; NMR δ$_H$(400MHz, CDCl$_3$) 7.88(1H, d, J 5.5Hz), 7.37(1H, d, J 1.0Hz), 7.21(1H, d, J 5.5Hz), 7.08 (1H, d, J 1.5Hz), 5.61(2H, s), 4.18(2H, q, J 7.5Hz), 3.24(6H, s), 1.18 (3H, t, J 7.0Hz). |
| 178 | | Mp 162.2-164.9° C.; IR ν$_{max}$(Nujol)/cm$^{-1}$ 3365, 2924, 2854, 1559, 1528, 1512, 1465, 1389, 1378, 1336, and 1236; NMR δ$_H$(400MHz, CDCl$_3$) 7.89(1H, d, J 5.5Hz), 7.34(1H, d, J 1.0Hz), 7.22(1H, d, J 5.5Hz), 7.19(1H, d, J 1.0Hz), 4.94(2H, t, J 5.0Hz), 4.09(2H, br q, J 5.0Hz), 3.26(6H, s), 2.50(1H, br t, J 5.0Hz). |
| 179 | | Mp 69-70° C.; IR ν$_{max}$(Nujol)/cm$^{-1}$ 3090, 2925, 2854, 1542, 1514, 1477, 1376, 1336, 1221 and 1109; NMR δ$_H$(400MHz, CDCl$_3$) 8.04(1H, d, J 5.5Hz), 7.50(1H, d, J 5.5Hz), 7.40(1H, d, J 1.0Hz), 7.34(1H, d, J 1.0Hz), 6.29(2H, s), 3.40(3H, s), 3.15(2H, q, 7.5Hz), 1.49(3H, t, J 7.5Hz). |
| 180 | | Mp <100° C.; IR ν$_{max}$(Nujol)/cm$^{-1}$ 2953, 2925, 2854, 1547, 1514, 1495, 1458, 1378, 1316, 1248 and 1095; NMR δ$_H$(400MHz, CDCl$_3$) 8.17(1H, s), 8.10(1H, d, J 5.5Hz), 7.56(1H, d, J 5.5Hz), 6.41(2H, s), 3.73(2H, t, J 8.0Hz), 3.20(2H, q, J 7.5Hz), 1.50(3H, t, J 8.0Hz), 0.90(2H, t, J 8.0Hz), 0.09(9H, s). |
| 181 | | Mp 108-109° C.; IR ν$_{max}$(Nujol)/cm$^{-1}$ 3076, 2954, 2923, 2854, 1571, 1537, 1519, 1443, 1400, 1249, 1129 and 1116; NMR δ$_H$(400MHz, |

TABLE 2-continued

Analytical data
HPLC is carried out using the following conditions: Column.
Supelcosil ABZ+ (170 × 4.6 mm),
particle size 5 μM, mobile phase MeOH: 10 mM aq
NH₄OAc (80:20), (70:30) or (60:40) (specified
in Table 2), flow rate 1.0 mL/min.,
detection wavelength λ = 230 nM
(unless otherwise stated), retention
times are provided in Table 2.

| Example | Yield(%) | Physical Data |
|---|---|---|
| | | CDCl₃) 8.49(1H, s), 8.38(1H, s), 8.05(1H, d, J 5.5Hz), 7.54(1H, d, J 5.5Hz), 5.55(2H, s), 3.66(2H, t, J 8.0Hz), 0.96(2H, t, J 8.5Hz), 0.00 (9H, s). |
| 182 | | Mp 141-142° C.; IR $\nu_{max}$(Nujol)/cm$^{-1}$ 2925, 2854, 1545, 1522, 1462, 1378 and 1225; NMR $\delta_H$(400MHz, CDCl₃) 8.10(1H, d, J 5.5Hz), 7.65 (1H, d, J 2.0Hz) 7.57(1H, d, J 5.5Hz), 7.11(1H, d, J 2.0Hz), 4.37(3H, s). |
| 183 | | Mp 60-61° C.; IR $\nu_{max}$(Nujol)/cm$^{-1}$ 2924, 2854, 1579, 1556, 1458, 1404, 1377, 1278, 1247 and 1100; NMR $\delta_H$(400MHz, CDCl₃) 8.36(1H, s), 8.32(1H, s), 7.77(1H, d, J 5.5Hz), 7.27(1H, d, J 5.5Hz), 5.53(2H, s), 3.66 2H, t, J 8.5Hz) 3.30(6H, s), 0.96(3H, t, J 8.0Hz), 0.00(9H, s). |
| 184 | | Mp 126.5-127° C.; IR $\nu_{max}$(Nujol)/cm$^{-1}$ 3052, 2954, 2924, 2854, 1553, 1515, 1465, 1412, 1386, 1353 and 1232; NMR $\delta_H$(400MHz, CDCl₃) 7.80(1H, d, J 5.5Hz), 7.60(1H, d, J 2.0Hz), 7.27(1H, d, J 5.5Hz), 7.01 (1H, d, J 2.0Hz), 4.34(3H, s), 3.29(6H, s). |
| 185 | | Mp 210-211° C.; IR $\nu_{max}$(Nujol)/cm$^{-1}$ 3146, 3090, 3058, 2924, 2854, 1582, 1556, 1465, 1404, 1377, 1277 and 1236; NMR $\delta_H$(400MHz, CDCl₃) 10.47(1H, br s), 8.39(2H, s), 7.77(1H, d, J 5.5Hz), 7.33-7.23 (1H, d, J 5.5Hz), 3.30(6H, s). |
| 186 | | Mp 175.4-175.9° C.; IR $\nu_{max}$(Nujol)/cm$^{-1}$ 2925, 2854, 1548, 1458, 1407, 1383, 1279 and 1228; NMR $\delta_H$(400MHz, CDCl₃) 8.25(1H, s), 8.15(1H, s), 7.75(1H, d, J 5.5Hz), 7.25(1H, d, J 5.5Hz), 4.02(3H, s), 3.29(6H, s), |
| 187 | | Mp 110.2-111.4° C.; NMR $\delta_H$(400MHz, CDCl₃) 8.10(1H, d, J 5.5Hz), 7.56(1H, d, J 5.5Hz), 7.26(1H, s), 4.58(3H, s), 3.20(2H, q, J 7.5Hz), 1.50(3H, t, J 7.5Hz). |
| 188 | | Mp 104.7-104.8° C.; IR $\nu_{max}$(Nujol)/cm$^{-1}$ 3095; 2926, 2854, 1595, 1552, 1532, 1505, 1483, 1458, 1434, 1377, 1349 and 1302; p NMR $\delta_H$ (400MHz, CDCl₃) 7.45(1H, d, J 3.5Hz), 7.26(1H, s), 7.15(1H, d, J 1.5Hz), 6.64(1H, dd, J 3.5Hz, 2.0Hz), 3.08(2H, q, J 7.5Hz), 2.69(3H, s), 1.45(3H, t, J 7.5Hz). |

Adenosine Receptor Binding

Binding Affinities at hA$_{2A}$ Receptors

The compounds were examined in an assay measuring in vitro binding to human adenosine A$_{2A}$ receptors by determining the displacement of the adenosine A$_{2A}$ receptor selective radioligand [³H]-CGS 21680 using standard techniques. The results are summarised in Table 3

TABLE 3

| Example | K$_i$ (nM) |
|---|---|
| Example 15 | 11 |
| Example 40 | 19 |
| Example 65 | 2 |
| Example 70 | 4 |
| Example 71 | 8 |
| Example 76 | 1 |
| Example 79 | 14 |
| Example 80 | 1 |
| Example 82 | 2 |
| Example 89 | 20 |
| Example 104 | 5 |
| Example 105 | 6 |
| Example 110 | 35 |
| Example 111 | 2 |
| Example 113 | 1 |
| Example 139 | 3 |
| Example 140 | 2 |
| Example 141 | 9 |

TABLE 3-continued

| Example | K$_i$ (nM) |
|---|---|
| Example 152 | 3 |
| Example 154 | 6 |

Evaluation of Potential Anti-Parkinsonian Activity In Vivo

Haloperidol-induced Hypolocomotion Model

It has previously been demonstrated that adenosine antagonists, such as theophylline, can reverse the behavioural depressant effects of dopamine antagonists, such as haloperidol, in rodents (Mandhane S. N. et al., Adenosine A$_2$ receptors modulate haloperidol-induced catalepsy in rats. Eur. J. Pharmacol. 1997, 328, 135-141). This approach is also considered a valid method for screening drugs with potential antiparkinsonian effects. Thus, the ability of novel adenosine antagonists to block haloperidol-induced deficits in locomotor activity in mice can be used to assess both in vivo and potential antiparkinsonian efficacy.

Method

Female TO mice (25-30 g) obtained from TUCK, UK, are used for all experiments. Animals are housed in groups of 8 [cage size—40 (width)×40 (length)×20 (height)cm] under 12 hr light/dark cycle (lights on 08:00 hr), in a temperature (20±2° C.) and humidity (55±15%) controlled environment. Animals have free access to food and water, and are allowed at least 7 days to acclimatize after delivery before experimental use.

Drugs

Liquid injectable haloperidol (1 ml Serenance ampoules from Baker Norton, Harlow, Essex, each containing haloperidol BP 5 mg, batch # P424) are diluted to a final concentration of 0.02 mg/ml using saline. Test compounds are typically prepared as aqueous suspensions in 8% Tween. All compounds are administered intraperitoneally in a volume of 10 ml/kg.

Procedure 1.5 hours before testing, mice are administered 0.2 mg/kg haloperidol, a dose that reduces baseline locomotor activity by at least 50%. Test substances are typically administered 5-60 minutes prior to testing. The animals are then placed individually into clean, clear polycarbonate cages [20 (width)×40 (length)×20 (height) cm, with a flat perforated, Perspex lid]. Horizontal locomotor activity is determined by placing the cages within a frame containing a 3×6 array of photocells linked to a computer, which tabulates beam breaks. Mice are left undisturbed to explore for 1 hour, and the number of beams breaks made during this period serves as a record of locomotor activity which is compared with data for control animals for statistically significant differences.

6-OHDA Model

Parkinson's disease is a progressive neurodegenerative disorder characterised by symptoms of muscle rigidity, tremor, paucity of movement (hypokinesia), and postural instability. It has been established for some time that the primary deficit in PD is a loss of dopaminergic neurones in the substantia nigra which project to the striatum, and indeed a substantial proportion of striatal dopamine is lost (ca 80-85%) before symptoms are observed. The loss of striatal dopamine results in abnormal activity of the basal ganglia, a series of nuclei which regulate smooth and well co-ordinated movement (Blandini F. et al., Glutamate and Parkinson's Disease. *Mol. Neurobiol.* 1996, 12, 73-94). The neurochemical deficits seen in Parkinson's disease can be reproduced by local injection of the dopaminergic neurotoxin 6-hydroxydopamine into brain regions containing either the cell bodies or axonal fibres of the nigrostriatal neurones.

By unilaterally lesioning the nigrostriatal pathway on only one-side of the brain, a behavioural asymmetry in movement inhibition is observed. Although unilaterally-lesioned animals are still mobile and capable of self maintenance, the remaining dopamine-sensitive neurones on the lesioned side become supersenstive to stimulation. This is demonstrated by the observation that following systemic administration of dopamine agonists, such as apomorphine, animals show a pronounced rotation in a direction contralateral to the side of lesioning. The ability of compounds to induce contralateral rotations in 6-OHDA lesioned rats has proven to be a sensitive model to predict drug efficacy in the treatment of Parkinson's Disease.

Animals

Male Sprague-Dawley rats, obtained from Charles River, are used for all experiments. Animals are housed in groups of 5 under 12 hr light/dark cycle (lights on 08:00 hr), in a temperature (20±2° C.) and humidity (55±15%) controlled environment. Animals have free access to food and water, and are allowed at least 7 days to acclimatize after delivery before experimental use.

Drugs

Ascorbic acid, desipramine, 6-OHDA and apomorphine (Sigma-Aldrich, Poole, UK). 6-OHDA is freshly prepared as a solution in 0.2% ascorbate at a concentration of 4 mg/mL prior to surgery. Desipramine is dissolved in warm saline, and administered in a volume of 1 ml/kg. Apomorphine is dissolved in 0.02% ascorbate and administered in a volume of 2 mL/kg. Test compounds are suspended in 8% Tween and injected in a volume of 2 mL/kg.

Surgery 15 minutes prior to surgery, animals are given an intraperitoneal injection of the noradrenergic uptake inhibitor desipramine (25 mg/kg) to prevent damage to non-dopamine neurones. Animals are then placed in an anaesthetic chamber and anaesthetised using a mixture of oxygen and isoflurane. Once unconscious, the animals are transferred to a stereotaxic frame, where anaesthesia is maintained through a mask. The top of the animal's head is shaved and sterilised using an iodine solution. Once dry, a 2 cm long incision is made along the midline of the scalp and the skin retracted and clipped back to expose the skull. A small hole is then drilled through the skill above the injection site. In order to lesion the nigrostriatal pathway, the injection cannula is slowly lowered to position above the right medial forebrain bundle at −3.2 mm anterior posterior, −1.5 mm medial lateral from bregma, and to a depth of 7.2 mm below the duramater. 2 minutes after lowing the cannula, 2 μL of 6-OHDA is infused at a rate of 0.5 μL/min over 4 minutes, yeilding a final dose of 8 μg. The cannula is then left in place for a further 5 minutes to facilitate diffusion before being slowly withdrawn. The skin is then sutured shut using Ethicon W501 Mersilk, and the animal removed from the strereotaxic frame and returned to its homecage. The rats are allowed 2 weeks to recover from surgery before behavioural testing.

Apparatus

Rotational behaviour is measured using an eight station rotameter system provided by Med Associates, San Diego, USA. Each station is comprised of a stainless steel bowl (45 cm diameter×15 cm high) enclosed in a transparent Plexiglas cover running around the edge of the bowl, and extending to a height of 29 cm. To assess rotation, rats are placed in cloth jacket attached to a spring tether connected to optical rotameter positioned above the bowl, which assesses movement to the left or right either as partial (45°) or full (360°) rotations. All eight stations are interfaced to a computer that tabulated data.

Procedure

To reduce stress during drug testing, rats are initially habituated to the apparatus for 15 minutes on four consecutive days. On the test day, rats are given an intraperitoneal injection of test compound 30 minutes prior to testing. Immediately prior to testing, animals are given a subcutaneous injection of a subthreshold dose of apomorphine, then placed in the harness and the number of rotations recorded for one hour. The total number of full contralatral rotations during the hour test period serves as an index of antiparkinsonian drug efficacy.

The invention claimed is:

1. A pharmaceutical composition, comprising a compound of formula (I)

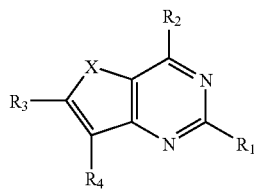

wherein

X is S or O;

$R_1$ is selected from the group consisting of H, alkyl, aryl, hydroxy, alkoxy, aryloxy, thioalkyl, thioaryl, halogen, CN, $COR_5$, $CO_2R_5$, $CONR_6R_7$, $CONR_5NR_6R_7$, $NR_6R_7$, $NR_5CONR_6R_7$, $NR_5COR_6$, $NR_5CO_2R_8$, and $NR_5SO_2R_8$;

$R_2$ is selected from aryl attached via an unsaturated ring carbon of said aryl group;

$R_3$ is selected from the group consisting of H, alkyl, hydroxy, alkoxy, halogen, CN and $NO_2$;

$R_4$ is selected from the group consisting of H, alkyl, aryl, hydroxy, alkoxy, aryloxy, thioalkyl, thioaryl, halogen, CN, $NO_2$, $COR_5$, $CO_2R_5$, $CONR_6R_7$, $CONR_5NR_6R_7$, $NR_6R_7$, $NR_5CONR_6R_7$, $NR_5COR_6$, $NR_5CO_2R_8$ and $NR_5SO_2R_8$;

$R_5$, $R_6$ and $R_7$ are independently selected from the group consisting of H, alkyl and aryl, or where $R_6$ and $R_7$ are in an ($NR_6R_7$) group, $R_6$ and $R_7$ may be linked to form a heterocyclic group, or where $R_5$, $R_6$ and $R_7$ are in a ($CONR_5NR_6R_7$) group, $R_5$ and $R_6$ may be linked to form a heterocyclic group; and $R_8$ is selected from alkyl and aryl, or a pharmaceutically acceptable salt thereof, in combination with a pharmaceutically acceptable carrier or excipient, wherein $R_1$ is not selected from the group consisting of phenyl, phenyl substituted by halogen, and phenyl substituted by halo-substituted lower alkyl.

2. The composition of claim 1 wherein X is S.

3. The composition of claim 1, wherein $R_1$ is selected from the group consisting of alkyl, alkoxy, thioalkyl, $NR_6R_7$ and $NR_5COR_6$.

4. The composition of claim 1, wherein $R_1$ is selected from alkyl and $NR_6R_7$.

5. The composition of claim 1, Wherein $R_1$ is selected from haloalkyl and arylalkyl.

6. The composition of claim 1, wherein $R_2$ is a 5- or 6- membered monocyclic aryl group.

7. The composition of claim 1, wherein $R_2$ is a heteroaryl group.

8. The composition of claim 7, wherein $R_2$ is a heteroaryl group which is attached to the pyrimidine ring of formula (I) such that a heteroatom is adjacent to the unsaturated carbon atom attached to said pyrimidine ring.

9. The composition of claim 7, wherein $R_2$ is an N, O or S-containing heteroaryl group.

10. The composition of claim 1, wherein $R_2$ is not ortho,ortho-disubstituted.

11. The composition of claim 1, wherein $R_2$ is not ortho-substituted.

12. The composition of claim 1, wherein $R_2$ is selected from the group consisting of furyl, thienyl, pyridyl and thiazolyl.

13. The composition of claim 1, wherein $R_2$ is selected from the group consisting of 2-furyl, 2-thienyl, 2-thiazolyl and 2-pyridyl.

14. The composition of claim 1, wherein $R_3$ is selected from the group consisting of H, $CF_3$, hydroxy, alkoxy, halogen, CN and $NO_2$.

15. The composition of claim 1, wherein $R_3$ is H.

16. The composition of claim 1, wherein $R_3$ is selected from alkyl or alkoxy and said alkyl group or the alkyl group of said alkoxy is selected from $C_{1-6}$ alkyl.

17. The composition of claim 1, wherein $R_4$ is selected from the group consisting of H, alkyl, halogen, $COR_5$, $CO_2R_5$, $CONR_6R_7$ and $CONR_5NR_6R_7$.

18. The composition of claim 1, wherein $R_4$ is selected from the group consisting of H, alkyl and halogen.

19. The composition of claim 18, wherein $R_4$ is selected from $C_{1-6}$ alkyl.

20. The composition of claim 18, wherein $R_4$ is selected from haloalkyl and arylalkyl.

21. The composition of claim 1, wherein $R_4$ is H.

22. The composition of claim 1, wherein $R_6$ and $R_7$ are linked to form a saturated heterocyclic ring.

23. The composition of claim 1, wherein $R_6$ and $R_7$ are linked to form a 5 or 6-membered heterocyclic ring.

24. The composition of claim 1, wherein $R_5$ to $R_8$ are independently selected from $C_{1-6}$ alkyl.

25. The composition of claim 1, wherein $R_5$ to $R_7$ are independently selected from H.

26. The composition of claim 1 which is selected from the group consisting of:

7-bromo-4-(2-furyl)-N-(2-hydroxyethyl)thieno[3,2-d]pyrimidine-2-amine;
N-allyl-4-(2-furyl)thieno[3,2-d]pyrimidine-2-amine;
2-ethyl-4-(2-pyridyl)thieno[3,2-d]pyrimidine;
2-methyl-4-(2-pyridyl)thieno[3,2-d]pyrimidine;
2-n-propyl-4-(2-pyridyl)thieno[3,2-d]pyrimidine;
N-(2-hydroxyethyl)-4-(2-thiazolyl)thieno[3,2-d]pyrimidine-2-amine;
2-isopropyl-4-(2-pyridyl)thieno[3,2-d]pyrimidine;
N-(2-methoxyethyl)-4-(2-furyl)thieno[3,2-d]pyrimidine-2-amine;
N,N-dimethyl-4-(4-methyl-2-thiazolyl)thieno[3,2-d]pyrimidine-2-amine;
4-(2-furyl)thieno[3,2-d]pyrimidine-2-amine;
2-ethyl-4-(4-methyl-2-thiazolyl)thieno[3,2-d]pyrimidine;
2-ethyl-4-(2-thiazolyl)thieno[3,2-d]pyrimidine;
N,N-dimethyl-4-(5-methyl-2-thiazolyl)thieno[3,2-d]pyrimidine-2-amine;
N,N-dimethyl-4-(4,5-dimethyl-2-thiazolyl)thieno[3,2-d]pyrimidine-2-amine;
4-(2-thiazolyl)thieno[3,2-d]pyrimidine-2-amine;
(2R)-2-(2-hydroxymethylpyrrolidin-1-yl)-4-(2-thiazolyl)thieno[3,2-d]pyrimidine;
N-allyl-4-(2-thiazolyl)thieno[3,2-d]pyrimidine-2-amine;
2-isopropyl-4-(2-thiazolyl)thieno[3,2-d]pyrimidine;
N,N-dimethyl-4-(5-methyl-2-pyridyl)thieno[3,2-d]pyrimidine-2-amine;
2-tert-butyl-4-(2-thiazolyl)thieno[3,2-d]pyrimidine;
2-cyclopropyl-4-(2-thiazolyl)thieno[3,2-d]pyrimidine;
2-ethyl-4-(6-methyl-2-pyridyl)thieno[3,2-d]pyrimidine;
(2S)-2-(2-hydroxymethylpyrrolidin-1-yl)-4-(2-thiazolyl)thieno[3,2-d]pyrimidine; and
2-(2-chloroethyl)-4-(2-thiazolyl)thieno[3,2-d]pyrimidine.

27. A method of treating a disorder in which the blocking of adenosine $A_{2A}$ receptors is beneficial, said disorder selected from: depression and acute and chronic pain, said method comprising administering to a subject in need of such treatment an effective dose of a compound of formula (I):

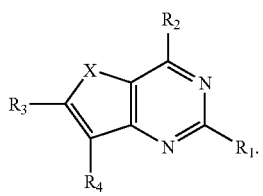

(1)

wherein
X is S or O;
$R_1$ is selected from the group consisting of H, alkyl, aryl, hydroxy, alkoxy, aryloxy, thioalkyl, thioaryl, halogen, CN, $COR_5$, $CO_2R_5$, $CONR_6R_7$, $CONR_5NR_6R_7$, $NR_6R_7$, $NR_5CONR_6R_7$, $NR_5COR_6$, $NR_5CO_2R_8$, and $NR_5SO_2R_8$;
$R_2$ is selected from aryl attached via an unsaturated ring carbon of said aryl group;
$R_3$ is selected from the group consisting of H, alkyl, hydroxy, alkoxy, halogen, CN and $NO_2$;
$R_4$ is selected from the group consisting of H, alkyl, aryl, hydroxy, alkoxy, aryloxy, thioalkyl, thioaryl, halogen, CN, $NO_2$, $COR_5$, $CO_2R_5$, $CONR_6R_7$, $CONR_5NR_6R_7$, $NR_6R_7$, $NR_5CONR_6R_7$, $NR_5COR_6$, $NR_5CO_2R_8$ and $NR_5SO_2R_8$;
$R_5$, $R_6$ and $R_7$ are independently selected from the group consisting of H, alkyl and aryl, or where $R_6$ and $R_7$ are in an ($NR_6R_7$) group, $R_6$ and $R_7$ may be linked to form a heterocyclic group, or where $R_5$, $R_6$ and $R_7$ are in a ($CONR_5NR_6R_7$) group, $R_5$ and $R_6$ may be linked to form a heterocyclic group; and
$R_8$ is selected from alkyl and aryl,
or a pharmaceutically acceptable salt thereof.

28. The method according to claim 27, wherein the disorder is caused by the hyperfunctioning of said receptors.

29. A compound of formula (I):

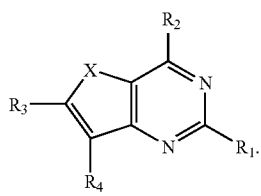

(1)

wherein
X is S or O;
$R_1$ is selected from the group consisting of H, alkyl, aryl, hydroxy, alkoxy, aryloxy, thioalkyl, thioaryl, halogen, CN, $COR_5$, $CO_2R_5$, $CONR_6R_7$, $CONR_5NR_6R_7$, $NR_6R_7$, $NR_5CONR_6R_7$, $NR_5COR_6$, $NR_5CO_2R_8$, and $NR_5SO_2R_8$;
$R_2$ is selected from aryl attached via an unsaturated ring carbon of said aryl group;
$R_3$ is selected from the group consisting of H, alkyl, hydroxy, alkoxy, halogen, CN and $NO_2$;
$R_4$ is selected from the group consisting of H, alkyl, aryl, hydroxy, alkoxy, aryloxy, thioalkyl, thioaryl, halogen, CN, $NO_2$, $COR_5$, $CO_2R_5$, $CONR_6R_7$, $CONR_5NR_6R_7$, $NR_6R_7$, $NR_5CONR_6R_7$, $NR_5COR_6$, $NR_5CO_2R_8$, and $NR_5SO_2R_8$;
$R_5$, $R_6$ and $R_7$ are independently selected from the group consisting of H, alkyl and aryl, or where $R_6$ and $R_7$ are in an ($NR_6R_7$) group, $R_6$ and $R_7$ may be linked to form a heterocyclic group, or where $R_5$, $R_6$ and $R_7$ are in a ($CONR_5NR_6R_7$) group, $R_5$ and $R_6$ may be linked to form a heterocyclic group; and
$R_8$ is selected from alkyl and aryl,
or a pharmaceutically acceptable salt thereof, wherein $R_1$ is not selected from the group consisting of phenyl, phenyl substituted by halogen, and phenyl substituted by halo-substituted lower alkyl.

30. The method according to claim 27, wherein the subject is human.

* * * * *